(12) United States Patent
Capacci et al.

(10) Patent No.: US 11,465,963 B2
(45) Date of Patent: Oct. 11, 2022

(54) TETRAHYDRONAPHTHALENE DERIVATIVES USEFUL AS NRF2 ACTIVATORS

(71) Applicant: BIOGEN MA INC., Cambridge, MA (US)

(72) Inventors: Andrew George Capacci, Cambridge, MA (US); Edward Yin Shiang Lin, Ashland, MA (US); Brian Stuart Lucas, Arlington, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/765,614

(22) PCT Filed: Nov. 20, 2018

(86) PCT No.: PCT/US2018/061998
§ 371 (c)(1),
(2) Date: May 20, 2020

(87) PCT Pub. No.: WO2019/104030
PCT Pub. Date: May 31, 2019

(65) Prior Publication Data
US 2020/0299230 A1    Sep. 24, 2020

Related U.S. Application Data

(60) Provisional application No. 62/589,259, filed on Nov. 21, 2017.

(51) Int. Cl.
*C07C 255/47* (2006.01)
*C07D 317/72* (2006.01)

(52) U.S. Cl.
CPC .......... *C07C 255/47* (2013.01); *C07D 317/72* (2013.01)

(58) Field of Classification Search
None
See application file for complete search history.

(56) References Cited

U.S. PATENT DOCUMENTS

2012/0196880 A1*  8/2012  Anderson ............ C07D 403/04
514/267

FOREIGN PATENT DOCUMENTS

| WO | 2010/011782 A1 | 1/2010 |
| WO | 2012/083306 A2 | 6/2012 |
| WO | 2016/065264 A1 | 4/2016 |

OTHER PUBLICATIONS

Caron et al. "Versatile Strategy to Access Tricycles Related to Quassinoids and Triterpenes" Organic Letters, 2010, vol. 12, No. 3, pp. 508-511.*
International Search Report and Written Opinion for Application No. PCT/US2018/061998, dated Feb. 5, 2019, 10 pages.

* cited by examiner

*Primary Examiner* — Joseph R Kosack
(74) *Attorney, Agent, or Firm* — McCarter & English, LLP; Steven G. Davis; Xin Zhang

(57) ABSTRACT

Provided are compounds of Formula I, or pharmaceutically acceptable salts thereof, and methods for their use as Nrf2 activators and for their production.

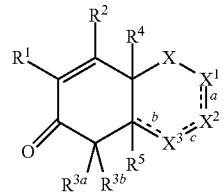

(I)

16 Claims, 4 Drawing Sheets

TETRAHYDRONAPHTHALENE DERIVATIVES USEFUL AS NRF2 ACTIVATORS

RELATED APPLICATION INFORMATION

This application is a 35 U.S.C. § 371 national stage filing of International Application No. PCT/US2018/061998, filed on Nov. 20, 2018, which in turn claims priority to U.S. Provisional Application No. 62/589,259, filed Nov. 21, 2017, the contents of each of which are incorporated herein in their entirety.

Nuclear factor erythroid 2 (NF-E2)-related factor 2 (Nrf2) belongs to the Cap 'N' Collar (CNC) family of transcription factors and contains a conserved basic leucine zipper (bZIP) structure. The main function of Nrf2 is to activate the cellular antioxidant response by inducing the production of proteins that are able to combat the harmful effects of oxidative stress.

Activation of the Nrf2 pathway to treat diseases caused by oxidative stress, such as a neurodegenerative disease, inflammation and/or an inflammatory disease, an autoimmune disease, an ischemic fibrotic disease, a cancer, premature aging, a cardiovascular disease, a liver disease, a hemoglobinopathy and a metabolic disorder, is being studied.

Moreover, Nrf2 activation has been shown to upregulate fetal hemoglobin which can ameliorates symptoms of hemoglobinopathy such as sickle cell disease and thalassemia (e.g. beta-thalassemia).

Therefore, a need exists for Nrf2 activators to treat these diseases.

SUMMARY

Disclosed herein are potent activators of Nrf2 (see Example 62). These compounds can be used in the treatment of diseases treatable by activating Nrf2. A first embodiment of the invention is a compound of Formula I:

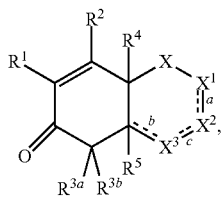

(I)

or a pharmaceutically acceptable salt thereof, wherein $R^1$ is —CN, —C(O)$R^{1a}$ or $C_{1-8}$alkyl substituted with one or more fluorine atoms;

$R^{1a}$ is H, $C_{1-12}$alkyl, $C_{2-12}$alkenyl, $C_{2-12}$alkynyl, a 3 to 12-membered carbocyclyl, a 3 to 12-membered heterocyclyl, —OR$^{10a}$, —SR$^{10a}$, —N(R$^{10a}$)$_2$, —NR$^{10a}$OR$^{10a}$, —NR$^{10a}$S(O)$_2$R$^{10a}$, —NR$^{10a}$C(O)R$^{10a}$, —N(R$^{10a}$)N(R$^{10a}$)$_2$, —N(R$^{10a}$)C(O)OR$^{10a}$ or —N(R$^{10a}$)C(O)N(R$^{10a}$)$_2$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more R$^{15}$;

$R^2$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{2a}$, —C(S)R$^{2a}$, —C(O)OR$^{2a}$, —C(S)SR$^{2a}$, —C(O)SR$^{2a}$, —C(S)OR$^{2a}$, —SC(O)R$^{2a}$, —OC(S)R$^{2a}$, —SC(S)R$^{2a}$, —C(O)N(R$^{2a}$)$_2$, —OR$^{2a}$, —SR$^{2a}$, —N(R$^{2a}$)$_2$, —N(R$^{2a}$)OR$^{2a}$, —N(R$^{2a}$)S(O)$_2$R$^{2a}$, —N(R$^{2a}$)C(O)R$^{2a}$, —N(R$^{2a}$)N(R$^{2a}$)$_2$, —N(R$^{2a}$)C(O)OR$^{2a}$, —N(R$^{2a}$)C(O)N(R$^{2a}$)$_2$, —S(O)$_2$R$^{2a}$, —S(O)R$^{2a}$, —S(O)N(R$^{2a}$)$_2$, —S(O)$_2$N(R$^{2a}$)$_2$, —N+(R$^{2a}$)$_3$, —S+(R$^{2a}$)$_2$ or —Si(R$^{2a}$)$_3$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more R$^{25}$;

$R^{3a}$ is H, $C_{1-12}$ alkyl, $C_{2-12}$ alkenyl, $C_{2-12}$ alkynyl, a 3 to 12-membered carbocyclyl, a 3 to 12-membered heterocyclyl, —C(O)R$^{30a}$, —C(O)OR$^{30a}$, —C(O)N(R$^{30a}$)$_2$, —OR$^{30a}$, —N(R$^{30a}$)$_2$, —N(R$^{30a}$)OR$^{30a}$, —N(R$^{30a}$)S(O)$_2$R$^{30a}$, —N(R$^{30a}$)C(O)R$^{30a}$, —N(R$^{30a}$)N(R$^{30a}$)$_2$, —N(R$^{30a}$)C(O)OR$^{30a}$, —N(R$^{30a}$)C(O)N(R$^{30a}$)$_2$, —S(O)R$^{30a}$, —S(O)N(R$^{30a}$)$_2$ or —S(O)$_2$N(R$^{30a}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{35}$ and $R^{3b}$ is $C_{1-12}$alkyl, $C_{2-12}$alkenyl, $C_{2-12}$alkynyl, a 3 to 12-membered carbocyclyl, a 3 to 12-membered heterocyclyl, —C(O)R$^{30b}$, —C(O)OR$^{30b}$, —C(O)N(R$^{30b}$)$_2$, —OR$^{30b}$, —N(R$^{30b}$)$_2$, —N(R$^{30b}$)OR$^{30b}$, —N(R$^{30b}$)S(O)$_2$R$^{30b}$, —N(R$^{30b}$)C(O)R$^{30b}$, —N(R$^{30b}$)N(R$^{30b}$)$_2$, —N(R$^{30b}$)C(O)OR$^{30b}$, —N(R$^{30b}$)C(O)N(R$^{30b}$)$_2$, —S(O)R$^{30b}$, —S(O)N(R$^{30b}$)$_2$ or —S(O)$_2$N(R$^{30b}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{35}$; or $R^{3a}$ and $R^{3b}$, taken together, are $C_{2-12}$ alkylene, $C_{2-12}$ alkenylene or $C_{2-12}$ alkynylene, wherein the $C_{2-12}$ alkylene, $C_{2-12}$ alkenylene and $C_{2-12}$ alkynylene are each optionally substituted with one or more R$^{35}$;

$R^4$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{4a}$, —C(S)R$^{4a}$, —C(O)OR$^{4a}$, —C(S)SR$^{4a}$, —C(O)SR$^{4a}$, —C(S)OR$^{4a}$, —SC(O)R$^{4a}$, —OC(S)R$^{4a}$, —SC(S)R$^{4a}$, —C(O)N(R$^{4a}$)$_2$, —OR$^{4a}$, —SR$^{4a}$, —N(R$^{4a}$)$_2$, —N(R$^{4a}$)OR$^{4a}$, —N(R$^{4a}$)S(O)$_2$R$^{4a}$, —N(R$^{4a}$)C(O)R$^{4a}$, —N(R$^{4a}$)N(R$^{4a}$)$_2$, —N(R$^{4a}$)C(O)OR$^{4a}$, —N(R$^{4a}$)C(O)N(R$^{4a}$)$_2$, —S(O)$_2$R$^{4a}$, —S(O)R$^{4a}$, —S(O)N(R$^{4a}$)$_2$, —S(O)$_2$N(R$^{4a}$)$_2$, —N+(R$^{4a}$)$_3$, —S+(R$^{4a}$)$_2$ or —Si(R$^{4a}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more R$^{45}$;

bonds "a", "b" and "c" depicted as ══════ are each independently either a single bond or a double bond, and (i) bonds "a", "b" and "c" are each a single bond, and $X^1$ is $C(R^6)_2$, $X^2$ is $C(R^7)_2$ and $X^3$ is $C(R^8)_2$; (ii) bond "a" is a double bond and bonds "b" and "c" are each a single bond, and $X^1$ is CR$^6$, $X^2$ is CR$^7$ and $X^3$ is $C(R^8)_2$; (iii) bond "b" is a double bond and bonds "a" and "c" are each a single bond, and $R^5$ is absent, $X^1$ is $C(R^6)_2$, $X^2$ is $C(R^7)_2$, and $X^3$ is CR$^8$; or (iv) bond "c" is a double bond and bonds "a" and "b" are each a single bond, wherein $X^1$ is $C(R^6)_2$, $X^2$ is CR$^7$, and $X^3$ is CR$^8$;

$R^5$ is H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{5a}$, —C(S)R$^{5a}$, —C(O)OR$^{5a}$, —C(S)SR$^{5a}$, —C(O)SR$^{5a}$, —C(S)OR$^{5a}$, —SC(O)R$^{5a}$, —OC(S)R$^{5a}$, —SC(S)R$^{5a}$, —C(O)N(R$^{5a}$)$_2$, —OR$^{5a}$, —SR$^{5a}$, —N(R$^{5a}$)$_2$, —N(R$^{5a}$)OR$^a$, —N(R$^{5a}$)S(O)$_2$R$^{5a}$, —N(R$^{5a}$)C(O)R$^a$, —N(R$^{5a}$)N(R$^{5a}$)$_2$, —N(R$^{5a}$)C(O)OR$^{5a}$, —N(R$^{5a}$)C(O)N(R$^{5a}$)$_2$, —S(O)$_2$R$^{5a}$, —S(O)R$^{5a}$, —S(O)N(R$^{5a}$)$_2$, —S(O)$_2$N(R$^{5a}$)$_2$, —N+(R$^{5a}$)$_3$, —S+(R$^{5a}$)$_2$ or —Si(R$^{5a}$)$_3$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more $R^{55}$;

$R^6$, in each occurrence, is independently H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{6a}$, —C(S)R$^{6a}$, —C(O)OR$^{6a}$, —C(S)SR$^{6a}$, —C(O)SR$^{6a}$, —C(S)OR$^{6a}$, —SC(O)R$^{6a}$, —OC(S)R$^{6a}$, —SC(S)R$^{6a}$, —C(O)N(R$^{6a}$)$_2$, —OR$^{6a}$, —SR$^{6a}$, —N(R$^{6a}$)$_2$, —N(R$^{6a}$)OR$^{6a}$, —N(R$^{6a}$)S(O)$_2$R$^{6a}$, —N(R$^{6a}$)C(O)R$^{6a}$, —N(R$^{6a}$)N(R$^{6a}$)$_2$, —N(R$^{6a}$)C(O)OR$^{6a}$, —N(R$^{6a}$)C(O)N(R$^{6a}$)$_2$, —S(O)$_2$R$^{6a}$, —S(O)R$^{6a}$, —S(O)N(R$^{6a}$)$_2$, —S(O)$_2$N(R$^{6a}$)$_2$, —N+(R$^{6a}$)$_3$, —S+(R$^{6a}$)$_2$ or —Si(R$^{6a}$)$_3$; or the two R$^6$ groups, taken together, are oxo, $C_{1-12}$ alkylidene, =NR$^{6a}$ or

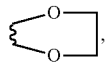

wherein the $C_{1-12}$alkyl, $C_{2-12}$alkenyl, $C_{2-12}$alkynyl, 3 to 12-membered carbocyclyl, 3 to 12-membered heterocyclyl, $C_{1-12}$alkylidene, and

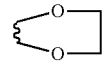

are each optionally substituted with one or more $R^{65}$;

$R^7$, in each occurrence, is independently H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{7a}$, —C(S)R$^{7a}$, —C(O)OR$^{7a}$, —C(S)SR$^{7a}$, —C(O)SR$^{7a}$, —C(S)OR$^{7a}$, —SC(O)R$^{7a}$, —OC(S)R$^{7a}$, —SC(S)R$^{7a}$, —C(O)N(R$^{7a}$)$_2$, —OR$^{7a}$, —SR$^{7a}$, —N(R$^{7a}$)$_2$, —N(R$^{7a}$)OR$^{7a}$, N(R$^{7a}$)S(O)$_2$R$^{7a}$, —N(R$^{7a}$)C(O)R$^{7a}$, —N(R$^{7a}$)N(R$^{7a}$)$_2$, —N(R$^{7a}$)C(O)OR$^{7a}$, —N(R$^{7a}$)C(O)N(R$^{7a}$)$_2$, —S(O)$_2$R$^{7a}$, —S(O)R$^{7a}$, —S(O)N(R$^{7a}$)$_2$, —S(O)$_2$N(R$^{7a}$)$_2$, —N+(R$^{7a}$)$_3$, —S+(R$^{7a}$)$_2$ or —Si(R$^{7a}$)$_3$; or the two R$^7$ groups, taken together, are oxo, $C_{1-12}$ alkylidene or =NR$^{7a}$, wherein the $C_{1-12}$alkyl, $C_{2-12}$alkenyl, $C_{2-12}$alkynyl, 3 to 12-membered carbocyclyl, 3 to 12-membered heterocyclyl, and $C_{1-12}$alkylidene are each optionally substituted with one or more $R^{75}$;

$R^8$, in each occurrence, is independently H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{8a}$, —C(S)R$^{8a}$, —C(O)OR$^{8a}$, —C(S)SR$^{8a}$, —C(O)SR$^{8a}$, —C(S)OR$^{8a}$, —SC(O)R$^{8a}$, —OC(S)R$^{8a}$, —SC(S)R$^{8a}$, —C(O)N(R$^{8a}$)$_2$, —OR$^{8a}$, —SR$^{8a}$, —N(R$^{8a}$)$_2$, —N(R$^{5a}$)OR$^{8a}$, N(R$^{8a}$)S(O)$_2$R$^{8a}$, —N(R$^{8a}$)C(O)R$^{8a}$, —N(R$^{8a}$)N(R$^{8a}$)$_2$, —N(R$^{8a}$)C(O)OR$^{8a}$, N(R$^{8a}$)C(O)N(R$^{8a}$)$_2$, —S(O)$_2$R$^{5a}$, —S(O)R$^{8a}$, —S(O)N(R$^{8a}$)$_2$, —S(O)$_2$N(R$^{8a}$)$_2$, —N+(R$^{8a}$)$_3$, —S+(R$^{8a}$)$_2$ or —Si(R$^{8a}$)$_3$; or the two R$^8$ groups, taken together, are oxo, $C_{1-12}$ alkylidene or =NR$^{8a}$, wherein the $C_{1-12}$alkyl, $C_{2-12}$alkenyl, $C_{2-12}$alkynyl, 3 to 12-membered carbocyclyl, 3 to 12-membered heterocyclyl, and $C_{1-12}$alkylidene are each optionally substituted with one or more $R^{85}$;

X is —C(R$^9$)$_2$—, —C(O)— or

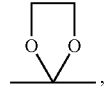

$R^9$, in each occurrence, is independently H, halo, —NO$_2$, —CN, —N$_3$, $C_{1-12}$alkyl, $C_{2-12}$alkenyl, $C_{2-12}$alkynyl, a 3 to 12-membered carbocyclyl, a 3 to 12-membered heterocyclyl, —C(O)R$^{9a}$, —C(S)R$^{9a}$, —C(O)OR$^{9a}$, —C(S)SR$^{9a}$, —C(O)SR$^{9a}$, —C(S)OR$^{9a}$, —SC(O)R$^{9a}$, —OC(S)R$^{9a}$, —SC(S)R$^{9a}$, —C(O)N(R$^{9a}$)$_2$, —OR$^{9a}$, —SR$^{9a}$, —N(R$^{9a}$)$_2$, —N(R$^{9a}$)OR$^{9a}$, —N(R$^{9a}$)S(O)$_2$R$^{9a}$, —N(R$^{9a}$)C(O)R$^{9a}$, —N(R$^{9a}$)N(R$^{9a}$)$_2$, —N(R$^{9a}$)C(O)OR$^{9a}$, —N(R$^{9a}$)C(O)N(R$^{9a}$)$_2$, —S(O)$_2$R$^{9a}$, —S(O)R$^{9a}$, —S(O)N(R$^{9a}$)$_2$, —S(O)$_2$N(R$^{9a}$)$_2$, —N+(R$^{9a}$)$_3$, —S+(R$^{9a}$)$_2$ or —Si(R$^{9a}$)$_3$; or the two R$^9$ groups, taken together, are oxo, $C_{1-12}$ alkylidene or =NR$^{9a}$, wherein the $C_{1-12}$alkyl, $C_{2-12}$alkenyl, $C_{2-12}$alkynyl, 3 to 12-membered carbocyclyl, 3 to 12-membered heterocyclyl, and $C_{1-12}$alkylidene are each optionally substituted with one or more $R^{95}$;

$R^{10a}$, $R^{2a}$, $R^{30a}$, $R^{30b}$, $R^{4a}$, $R^{5a}$, $R^{6a}$, $R^{7a}$, $R^{8a}$, and $R^{9a}$, in each occurrence, are independently H, $C_{1-12}$alkyl, $C_{2-12}$alkenyl, $C_{2-12}$alkynyl, $C_{1-12}$alkoxy, $C_{1-12}$acyl, —Si(R$^{16}$)$_3$, a 3 to 12-membered carbocyclyl or a 3 to 12-membered heterocyclyl, wherein the $C_{1-12}$alkyl, $C_{2-12}$alkenyl, $C_{2-12}$alkynyl, $C_{1-12}$alkoxy, $C_{1-12}$acyl, 3 to 12-membered carbocyclyl, and 3 to 12-membered heterocyclyl are each optionally substituted with one or more $R^{17}$;

$R^{16}$, in each occurrence, is independently H, $C_{1-12}$alkyl, $C_{2-12}$alkenyl, $C_{2-12}$alkynyl, a 3 to 12-membered carbocyclyl or a 3 to 12-membered heterocyclyl, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more $R^8$;

$R^{15}$, $R^{25}$, $R^{35}$, $R^{45}$, $R^{55}$, $R^{65}$, $R^{75}$, $R^{85}$, and $R^{95}$, in each occurrence, are independently halo, —OH, —CN, $C_{1-12}$alkyl, $C_{2-12}$alkenyl, $C_{2-12}$alkynyl, $C_{1-12}$alkoxy, a 3 to 12-membered carbocyclyl or a 3 to 12-membered heterocyclyl, wherein the $C_{1-12}$alkyl, $C_{2-12}$alkenyl, $C_{2-12}$alkynyl, $C_{1-12}$alkoxy, 3 to 12-membered carbocyclyl, and 3 to 12-membered heterocyclyl are each optionally substituted with one or more $R^{19}$; and $R^{17}$, $R^{18}$, and $R^{19}$, in each occurrence, are independently halo, —OH, —CN, $C_{1-12}$alkyl, $C_{2-12}$alkenyl, $C_{2-12}$alkynyl, $C_{1-12}$alkoxy, a 3 to 12-membered carbocyclyl or a 3 to 12-membered heterocyclyl, wherein the $C_{1-12}$alkyl, $C_{2-12}$alkenyl, $C_{2-12}$alkynyl, $C_{1-12}$alkoxy, 3 to 12-membered carbocyclyl and 3 to 12-membered heterocyclyl are each optionally substituted with one or more groups independently selected from halo, —OH, and $C_{1-4}$alkoxy;

provided that,
when R$^1$ is —C(O)R$^{1a}$, then R$^2$ is not —OR$^{2a}$;
when R$^1$ is —C(O)R$^{1a}$, R$^2$ is H, R$^4$ is H or methyl, X is —CH$_2$— or —CH(CH$_3$)—, bonds "a" and "b" are each a single bond, R$^5$ is H or —OH, X$^1$ is —CH$_2$— or —CH[OC(O)CH$_3$]—, X$^2$ is —CH$_2$—, and X$^3$ is —CH$_2$—, then CR$^{3a}$R$^{3b}$ is not CH(OR$^{30a}$) or C(C$_{1-12}$alkyl)(OR$^{30a}$); and
when R$^1$ is —C(O)R$^{1a}$, R$^2$ is H, one of R$^{3a}$ and R$^{3b}$ is H, R$^4$ is methyl, X is —CH$_2$—, bonds "a" and "b" are each a single bond, R$^5$ is H, X$^1$ is C(R$^6$)$_2$, X$^2$ is —CH(C$_{1-12}$ alkyl)-, wherein the C$_{1-12}$alkyl in X$^2$ is optionally substituted with —OH, and X$^3$ is —CH$_2$—, then at least one R$^6$ group is not H or C$_{1-12}$alkyl; and provided that,
the compound is not methyl 3-hydroxy-5-oxo-4a,5,6,7,8,8a-hexahydronaphthalene-2-carboxylate with the following structure:

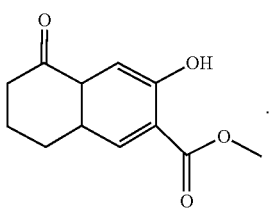 [SMILES: COC(=O)C1=CC2CCCC(=O)C2C=C1O]

Also provided is a pharmaceutical composition comprising at least one compound described herein, or a pharmaceutically acceptable salt thereof, and at least one pharmaceutically acceptable excipient.

Also provided is a compound, or a pharmaceutically acceptable salt thereof, described herein for use in medicine.

Also provided is a method for activating Nrf2 in a subject in need thereof, the method comprising administering to the subject a therapeutically effective amount of a compound described herein, or a pharmaceutically acceptable salt thereof, thereby activating Nrf2 in the subject.

Also provided is a compound, or a pharmaceutically acceptable salt thereof, described herein for use in the activation of Nrf2 in a subject in need thereof.

Also provided is use of a compound, or a pharmaceutically acceptable salt thereof, described herein in manufacture of a medicament for activating Nrf2 in a subject in need thereof.

Also provided is a method for treating a disease caused by oxidative stress in a subject, the method comprising administering to the subject a therapeutically effective amount of a compound described herein, or a pharmaceutically acceptable salt thereof.

Also provided is a compound, or a pharmaceutically acceptable salt thereof, described herein for use in the treatment of a disease caused by oxidative stress in a subject.

Also provided is use of a compound, or a pharmaceutically acceptable salt thereof, described herein in manufacture of a medicament for treating a disease caused by oxidative stress in a subject.

Also provided is a method for treating a disorder in a subject, wherein the disorder is selected from the group consisting of a neurodegenerative disease, inflammation/an inflammatory disease, an autoimmune disease, an ischemic fibrotic disease, a cancer, premature aging, a cardiovascular disease, a liver disease, a hemoglobinopathy, thalassemia (e.g., beta-thalassemia), and a metabolic disorder, the method comprising administering to the subject a therapeutically effective amount of a compound described herein, or a pharmaceutically acceptable salt thereof.

Also provided is a compound, or a pharmaceutically acceptable salt thereof, described herein for use in the treatment of a disorder in a subject, wherein the disorder is selected from the group consisting of a neurodegenerative disease, inflammation/an inflammatory disease, an autoimmune disease, an ischemic fibrotic disease, a cancer, premature aging, a cardiovascular disease, a liver disease, a hemoglobinopathy, thalassemia (e.g., beta-thalassemia), and a metabolic disorder.

Also provided is use of a compound, or a pharmaceutically acceptable salt thereof, described herein in manufacture of a medicament for treating a disorder in a subject, wherein the disorder is selected from the group consisting of a neurodegenerative disease, inflammation/an inflammatory disease, an autoimmune disease, an ischemic fibrotic disease, a cancer, premature aging, a cardiovascular disease, a liver disease, a hemoglobinopathy, thalassemia (e.g., beta-thalassemia), and a metabolic disorder.

Other features or advantages will be apparent from the following detailed description of several embodiments, and also from the appended claims.

DETAILED DESCRIPTION

Figure 1A:
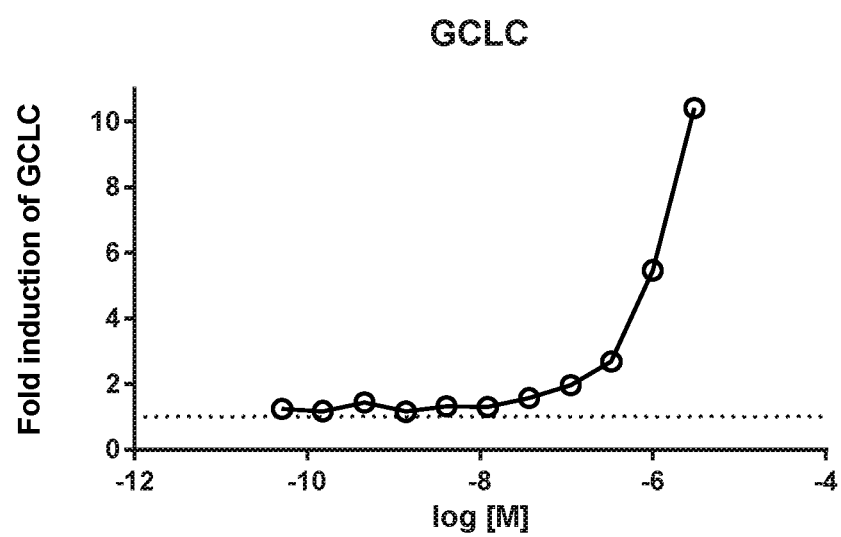
FIG. 1A shows transcription of GCLC in human astrocytes treated with increasing concentrations of Compound 24 for 20 hours.
Figure 1B:
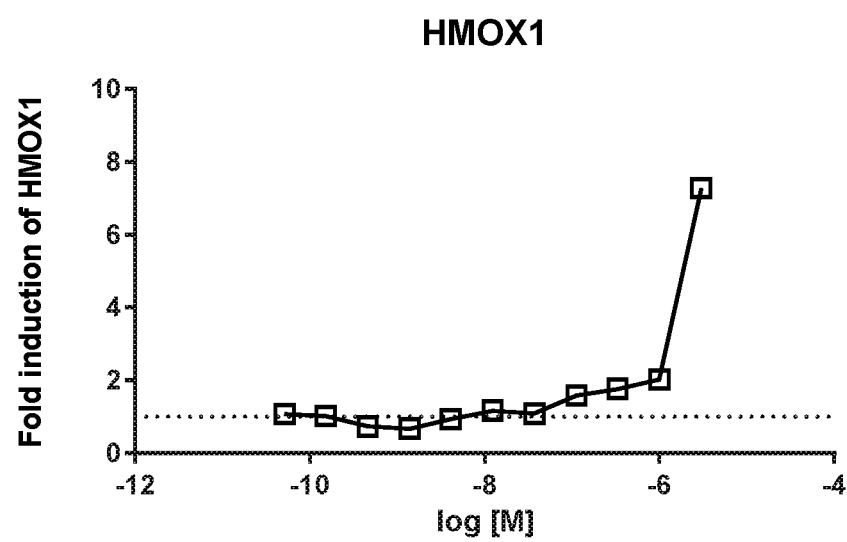
FIG. 1B shows transcription of HMOX1 in human astrocytes treated with increasing concentrations of Compound 24 for 20 hours.
Figure 1C:
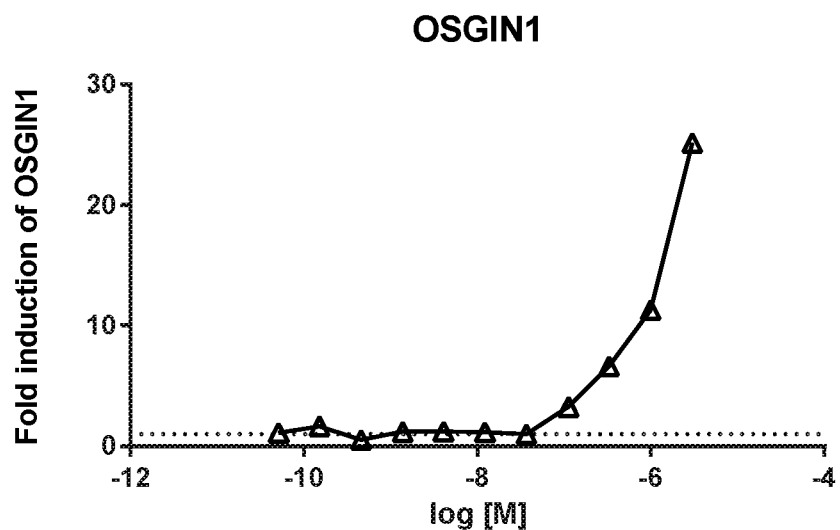
FIG. 1C shows transcription of OSGIN1 in human astrocytes treated with increasing concentrations of Compound 24 for 20 hours.
Figure 1D:
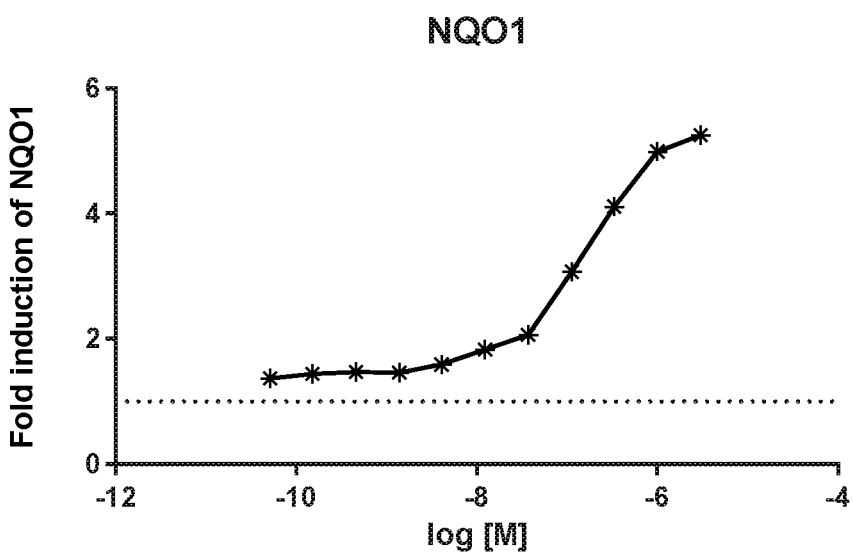
FIG. 1D shows transcription of NQO1 in human astrocytes treated with increasing concentrations of Compound 24 for 20 hours. The x-axis represents log (molar concentrations of compound 24).

The compounds or pharmaceutically acceptable salts thereof as described herein are Nrf2 activators.

In a second embodiment of the invention, the compound is represented by Formula II:

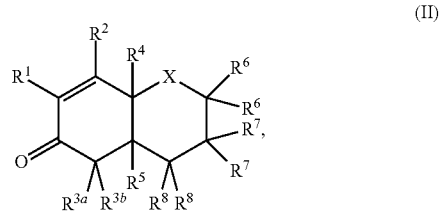

or a pharmaceutically acceptable salt thereof, wherein the values of the variables are as defined for the first embodiment.

In a third embodiment of the invention, the compound is represented by Formula IIA, IIB, IIC or IID:

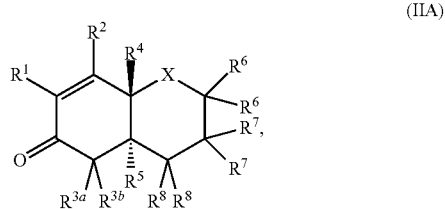

-continued

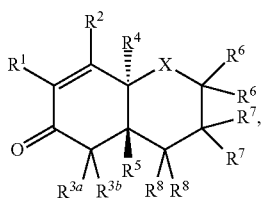
(IIB)

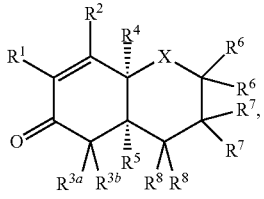
(IIC)

or

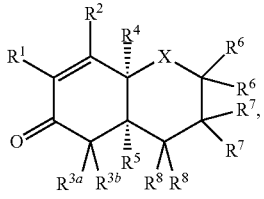
(IID)

or a pharmaceutically acceptable salt thereof, wherein the values of the variables are as defined for the first embodiment.

In a fourth embodiment of the invention, the compound is represented by Formula I, II, IIA, IIB, IIC or IID, or a pharmaceutically acceptable salt thereof, wherein $R^8$, in each occurrence, is independently H, halo, —CN, —OR$^{5a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{85}$; $R^{8a}$, in each occurrence, is independently H, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to six $R^{17}$; $R^{85}$, in each occurrence, is independently halo, —OH, —CN, $C_{1-12}$alkyl, $C_{2-12}$alkenyl, $C_{2-12}$alkynyl or $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{8a}$, is independently halo, —CN, —OH, $C_{1-6}$alkyl or $C_{1-6}$alkoxy, wherein the $C_{1-6}$alkyl and $C_{1-6}$alkoxy are each optionally substituted with one to six halo; and wherein the values of the other variables are as defined for the first embodiment.

In a fifth embodiment of the invention, the compound is represented by Formula I, II, IIA, IIB, IIC or IID, or a pharmaceutically acceptable salt thereof, wherein $R^8$, in each occurrence, is independently H or $C_{1-4}$alkyl; and wherein the values of the other variables are as defined for the first embodiment.

In a sixth embodiment of the invention, the compound is represented by Formula I, II, IIA, IIB, IIC or IID, or a pharmaceutically acceptable salt thereof, wherein $R^8$, in each occurrence, is H; and wherein the values of the other variables are as defined for the first embodiment.

In a seventh embodiment of the invention, the compound is represented by Formula

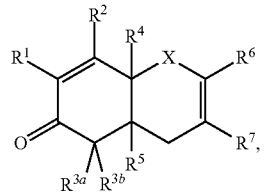
(III)

or a pharmaceutically acceptable salt thereof, wherein the values of the variables are as defined for the first, fourth, fifth and/or sixth embodiments.

In an eighth embodiment of the invention, the compound is represented by Formula IIIA, IIIB, IIIC or IIID:

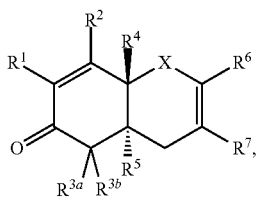
(IIA)

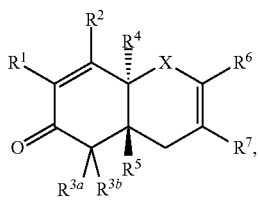
(IIB)

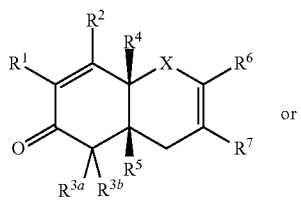
(IIC)

or

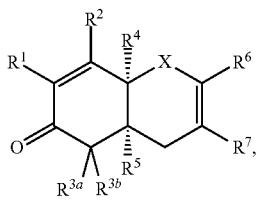
(IID)

or a pharmaceutically acceptable salt thereof, wherein the values of the variables are as defined for the first, fourth, fifth and/or sixth embodiments.

In a ninth embodiment of the invention, the compound is represented by Formula IV:

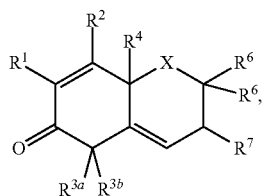
(IV)

or a pharmaceutically acceptable salt thereof, wherein the values of the variables are as defined for the first, fourth, fifth and/or sixth embodiments.

In a tenth embodiment of the invention, the compound is represented by Formula IVA or IVB:

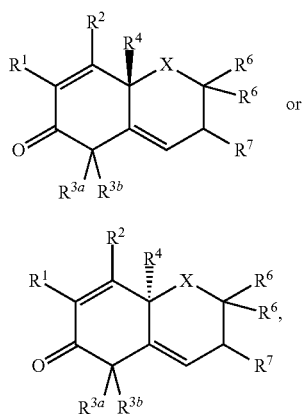

or a pharmaceutically acceptable salt thereof, wherein the values of the variables are as defined for the first, fourth, fifth and/or sixth embodiments.

In an eleventh embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein X is —C($R^9$)$_2$—; and wherein the values of the other variables are as defined for the first, fourth, fifth and/or sixth embodiments.

In a twelfth embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein $R^9$, in each occurrence, is independently H, halo, —CN, —OR$^{9a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{95}$; $R^{9a}$ is H, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to six $R^{17}$; $R^{95}$, in each occurrence, is independently halo, —OH, —CN, $C_{1-12}$alkyl, $C_{2-12}$alkenyl, $C_{2-12}$alkynyl or $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{9a}$, is independently halo, —CN, —OH, $C_{1-6}$alkyl or $C_{1-6}$alkoxy, wherein the $C_{1-6}$alkyl and $C_{1-6}$alkoxy are optionally substituted with one to six halo; and wherein the values of the other variables are as defined for the first, fourth, fifth, sixth and/or eleventh embodiments.

In a thirteenth embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein $R^9$, in each occurrence, is independently H or $C_{1-4}$alkyl; and wherein the values of the other variables are as defined for the first, fourth, fifth, sixth and/or eleventh embodiments.

In a fourteenth embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein $R^9$, in each occurrence, is H; and wherein the values of the other variables are as defined for the first, fourth, fifth, sixth and/or eleventh embodiments.

In a fifteenth embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein X is —C(O)—, and wherein the values of the other variables are as defined for the first, fourth, fifth and/or sixth embodiments.

In a sixteenth embodiment of the invention, the compound is represented by Formula I, II, IIA, IIB, IIC, IID, III, IIIA, IIIB, IIIC, IIID, IV, IVA or IVB, or a pharmaceutically acceptable salt thereof, wherein X is

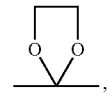

and wherein the values of the other variables are as defined for the first, fourth, fifth and/or sixth embodiments.

In a seventeenth embodiment of the invention, the compound is represented by one of Formula V, VI and VII:

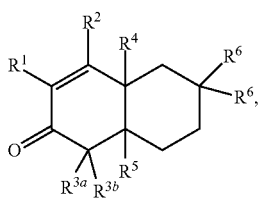
(V)

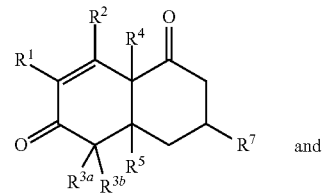
(VI)

and

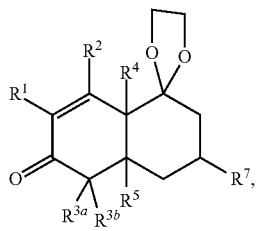
(VII)

or a pharmaceutically acceptable salt thereof, wherein the values of the variables are as defined for the first embodiment.

In an eighteenth embodiment of the invention, the compound is represented by one of Formula VA, VB, VC, VD, VIA, VIB, VIC, VID, VIIA, VIIB, VIIC and VIID:

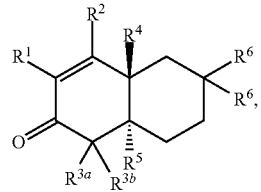
(VA)

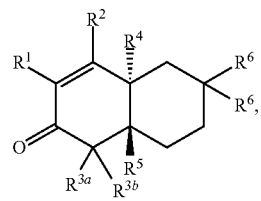
(VB)

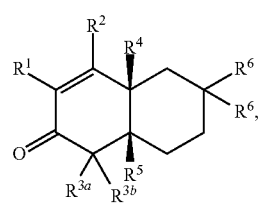
(VC)

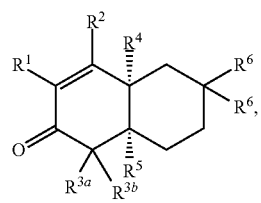
(VD)

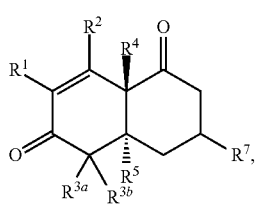
(VIA)

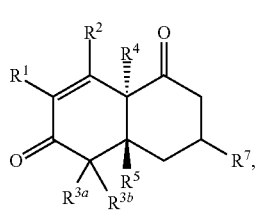
(VIB)

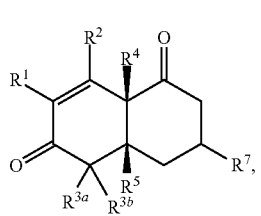
(VIC)

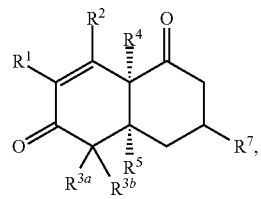
(VID)

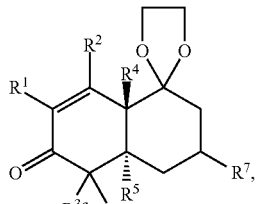
(VIIA)

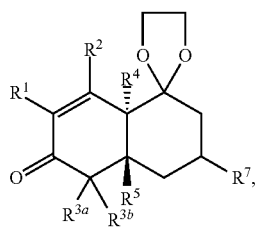
(VIIB)

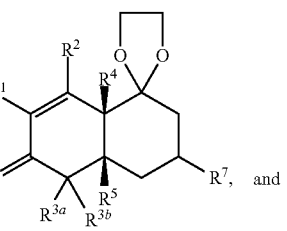
(VIIC)

and (VIID)

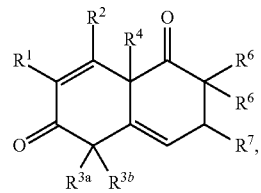

or a pharmaceutically acceptable salt thereof, wherein the values of the variables are as defined for the first embodiment.

In a nineteenth embodiment of the invention, the compound is represented by one of Formula VIII, XI and X:

(VIII)

-continued

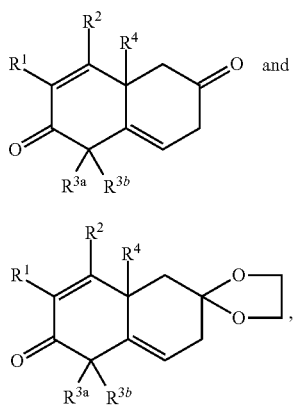
and

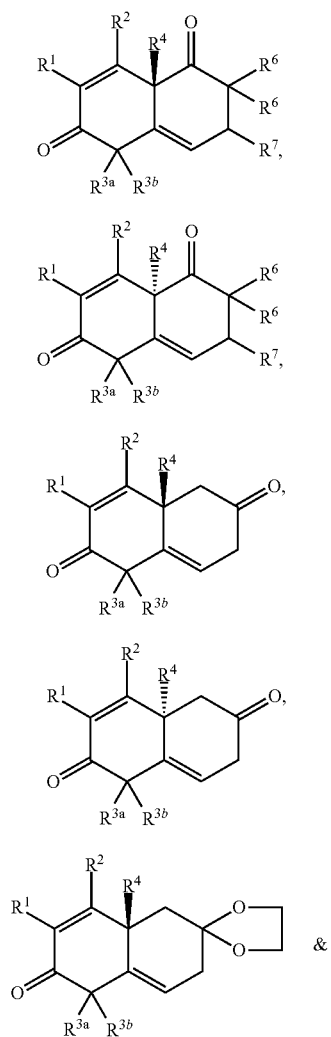

or a pharmaceutically acceptable salt thereof, wherein the values of the variables are as defined for the first embodiment.

In a twentieth embodiment of the invention, the compound is represented by one of Formula VIIIA, VIIIB, IXA, IXB, XA and XB:

(VIIIA)

(VIIIB)

(IXA)

(IXB)

(XA)

(IX)

(X)

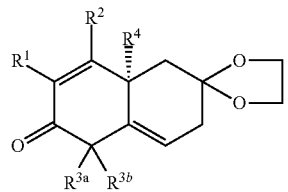

(XB)

or a pharmaceutically acceptable salt thereof, wherein the values of the variables are as defined for the first embodiment.

In a twenty-first embodiment of the invention, the compound is represented by Formula I, II, IIA, IIB, IIC, IID, III, IIIA, IIIB, IIIC, IIID, IV, IVA, IVB, V, VA, VB, VC, VD, VIII, VIIIA or VIIIB, or a pharmaceutically acceptable salt thereof, wherein $R^6$, in each occurrence, is independently H, halo, —CN, —$OR^{6a}$, —$N(R^{6a})_2$, —$N(R^{6a})S(O)_2R^{6a}$, —$N(R^{6a})C(O)R^{6a}$, $C_{1-12}$alkyl, $C_{2-12}$alkenyl, $C_{2-12}$alkynyl, a 3 to 12-membered carbocyclyl or a 3 to 12-membered heterocyclyl; or the two $R^6$ groups, taken together, are oxo, $C_{1-12}$ alkylidene or

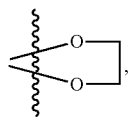

wherein the $C_{1-12}$alkyl, $C_{2-12}$alkenyl, $C_{2-12}$alkynyl, a 3 to 12-membered carbocyclyl, a 3 to 12-membered heterocyclyl, $C_{1-12}$ alkylidene, and

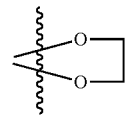

are each optionally substituted with one to eight $R^{65}$; $R^{6a}$, in each occurrence, is independently H, $C_{1-12}$alkyl, $C_{2-12}$alkenyl, $C_{2-12}$alkynyl or a 3 to 12-membered carbocyclyl, wherein the $C_{1-12}$alkyl, $C_{2-12}$alkenyl, $C_{2-12}$alkynyl, $C_{1-12}$acyl, and 3 to 12-membered carbocyclyl are each optionally substituted with one to six $R^{17}$; $R^7$, in each occurrence, is independently H, halo, —CN, —$OR^{7a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{75}$; $R^{7a}$, in each occurrence, is independently H, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to six $R^{17}$; $R^{65}$, in each occurrence, is independently halo, —OH, —CN, $C_{1-12}$alkyl, $C_{2-12}$alkenyl, $C_{2-12}$alkynyl, $C_{1-12}$alkoxy or a 3 to 12-membered carbocyclyl, wherein the $C_{1-12}$alkyl, $C_{2-12}$alkenyl, $C_{2-12}$alkynyl, $C_{1-12}$alkoxy, and 3 to 12-membered carbocyclyl are each optionally substituted with one to six groups independently selected from halo, —OH, and $C_{1-6}$alkoxy; $R^{75}$, in each occurrence, is independently halo, —OH, —CN, $C_{1-12}$alkyl, $C_{2-12}$alkenyl, $C_{2-12}$alkynyl or $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{6a}$ or $R^{7a}$, is independently halo, —CN, —OH, $C_{1-12}$alkyl, $C_{1-6}$alkoxy or a 3 to 12-membered carbocyclyl, wherein the $C_{1-6}$alkyl, $C_{1-6}$alkoxy, and 3 to 12-membered carbocyclyl are each optionally substituted with one to six halo; and wherein the values of the other variables are as defined for the first, fourth, fifth, sixth, eleventh, twelfth, thirteenth, fourteenth, fifteenth and/or sixteenth embodiments.

In a twenty-second embodiment of the invention, the compound is represented by Formula I, II, IIA, IIB, IIC, IID, III, IIIA, IIIB, IIIC, IIID, IV, IVA, IVB, V, VA, VB, VC, VD, VIII, VIIIA or VIIIB, or a pharmaceutically acceptable salt thereof, wherein $R^6$, in each occurrence, is independently H, halo, $C_{1-6}$alkyl, —$OR^{6a}$, —$N(R^{6a})_2$, —$N(R^{6a})S(O)_2R^{6a}$, —$N(R^{6a})C(O)R^{6a}$, a 3 to 8-membered carbocyclyl or a 5 to 10-membered heterocyclyl; or the two $R^6$ groups, taken together, are oxo, $C_{1-6}$ alkylidene or

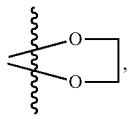

wherein the $C_{1-6}$alkyl, 3 to 8-membered carbocyclyl, 5 to 10-membered heterocyclyl, $C_{1-6}$ alkylidene, and

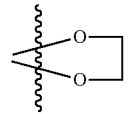

are each optionally substituted with one to six $R^{65}$; $R^{6a}$, in each occurrence, is independently H, $C_{1-6}$alkyl, $C_{1-6}$acyl or 3 to 10-membered carbocyclyl, wherein $C_{1-6}$alkyl and 3 to 10-membered carbocyclyl are each optionally substituted with one to four $R^{17}$; $R^7$, in each occurrence, is independently H or $C_{1-6}$alkyl, wherein $C_{1-6}$alkyl is optionally substituted with one to six groups independently selected from halo, —OH, $C_{1-6}$alkoxy, and —CN; $R^{65}$, in each occurrence, is independently 3 to 10-membered carbocyclyl or halo, wherein the 3 to 10-membered carbocyclyl is optionally substituted with one to four groups independently selected from halo, —OH, and $C_{1-6}$alkoxy; and $R^{17}$, in each occurrence, as an optional substituent of $R^{6a}$, is independently a 3 to 10-membered carbocyclyl, halo, —OH, $C_{1-4}$alkoxy or —CN; and wherein the values of the other variables are as defined for the first, fourth, fifth, sixth, eleventh, twelfth, thirteenth, fourteenth, fifteenth and/or sixteenth embodiments.

In a twenty-third embodiment of the invention, the compound is represented by Formula I, II, IIA, IIB, IIC, IID, III, IIIA, IIIB, IIIC, IIID, IV, IVA, IVB, V, VA, VB, VC, VD, VIII, VIIIA or VIIIB, or a pharmaceutically acceptable salt thereof, wherein $R^6$, in each occurrence, is independently H, halo, $C_{1-4}$alkyl, phenyl, 1,2,3,4-tetrahydroisoquinolinyl, pyrrolidinyl, morpholinyl, pyridyl, —$OR^{6a}$, —$N(R^{6a})_2$, —$N(R^{6a})S(O)_2R^{6a}$ or —$N(R^{6a})C(O)R^{6a}$; or the two $R^6$ groups, taken together, are oxo, $C_{1-4}$ alkylidene or

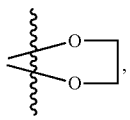

wherein the $C_{1-4}$alkyl, phenyl, 1,2,3,4-tetrahydroisoquinolinyl, pyrrolidinyl, morpholinyl, pyridyl, $C_{1-4}$ alkylidene, and

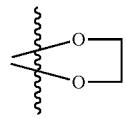

are each optionally substituted with one to four $R^{65}$; $R^{6a}$, in each occurrence, is independently H, $C_{1-4}$alkyl, 3 to 8-membered cycloalkyl or phenyl, wherein $C_{1-4}$alkyl, $C_{1-4}$acyl, and phenyl are each optionally substituted with one to three $R^{17}$; $R^7$, in each occurrence, is independently H or $C_{1-4}$alkyl; $R^{65}$, in each occurrence, is independently phenyl or halo; and $R^{17}$, in each occurrence, as an optional substituent of $R^{6a}$, is independently phenyl; and wherein the values of the other variables are as defined for the first, fourth, fifth, sixth, eleventh, twelfth, thirteenth, fourteenth, fifteenth and/or sixteenth embodiments.

In a twenty-fourth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^1$ is —CN; and wherein the values of the other variables are as defined for the first, fourth, fifth, sixth, eleventh, twelfth, thirteenth, fourteenth, fifteenth, sixteenth, twenty-first, twenty-second and/or twenty-third embodiments.

In a twenty-fifth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^1$ is —$CF_3$; and wherein the values of the other variables are as defined for the first, fourth, fifth, sixth, eleventh, twelfth, thirteenth, fourteenth, fifteenth, sixteenth, twenty-first, twenty-second and/or twenty-third embodiments.

In a twenty-sixth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^1$ is —$C(O)R^{1a}$; $R^{1a}$ is H, $C_{1-12}$alkyl, $C_{2-12}$alkenyl, $C_{2-12}$alkynyl, a 3 to 12-membered carbocyclyl or a 3 to 12-membered heterocyclyl, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one to six $R^{15}$; and $R^{15}$, in each occurrence, is independently selected from halo, —OH, $C_{1-12}$alkyl, and $C_{1-12}$alkoxy, wherein the $C_{1-12}$alkyl and $C_{1-12}$alkoxy are each optionally substituted with one to three groups independently selected from halo, —OH, and $C_{1-4}$alkoxy; and wherein the values of the other variables are as defined for the first, fourth, fifth, sixth, eleventh, twelfth, thirteenth, fourteenth, fifteenth, sixteenth, twenty-first, twenty-second and/or twenty-third embodiments.

In a twenty-seventh embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{1a}$ is H or $C_{1-6}$alkyl (which is optionally substituted with one to four halo groups); and wherein the values of the other variables are as defined for the first, fourth, fifth, sixth, eleventh, twelfth, thirteenth, fourteenth, fifteenth, sixteenth, twenty-first, twenty-second, twenty-third and/or twenty-sixth embodiments.

In a twenty-eighth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{1a}$ is H or $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third and/or twenty-sixth embodiments.

In a twenty-ninth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^2$ is H, halo, —CN, —$OR^{2a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{25}$; $R^{2a}$ is selected from H, $C_{1-12}$alkyl, $C_{2-12}$alkenyl, and $C_{2-12}$alkynyl, wherein the $C_{1-12}$alkyl, $C_{2-12}$alkenyl, and $C_{2-12}$alkynyl are each optionally substituted with one to six $R^{17}$; $R^{25}$, in each occurrence, is independently selected from halo, —OH, —CN, $C_{1-12}$alkyl, $C_{2-12}$alkenyl, $C_{2-12}$alkynyl, and $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{2a}$, is independently selected from halo, —CN, —OH, $C_{1-6}$alkyl, and $C_{1-6}$alkoxy, wherein the $C_{1-6}$alkyl and $C_{1-6}$alkoxy are each optionally substituted with one to six halo; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh and/or twenty-eighth embodiments.

In a thirtieth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^2$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, $C_{1-4}$alkyl, and $C_{1-4}$alkoxy; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh and/or twenty-eighth embodiments.

In a thirty-first embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^2$ is H or $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh and/or twenty-eighth embodiments.

In a thirty-second embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^2$ is H; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh and/or twenty-eighth embodiments.

In a thirty-third embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{3a}$ is H, halo, —CN, —$OR^{30a}$, $C_{1-12}$ alkyl, $C_{2-12}$ alkenyl or $C_{2-12}$ alkynyl, wherein the $C_{1-12}$alkyl, $C_{2-12}$alkenyl, and $C_{2-12}$alkynyl are each optionally substituted with one to eight $R^{35}$; $R^{3b}$ is halo, —CN, —$OR^{30b}$, $C_{1-12}$ alkyl, $C_{2-12}$ alkenyl or $C_{2-12}$ alkynyl, wherein the $C_{1-12}$alkyl, $C_{2-12}$alkenyl, and $C_{2-12}$alkynyl are each optionally substituted with one to eight $R^{35}$; $R^{30a}$ and $R^{30b}$ are each independently selected from H, $C_{1-12}$alkyl, $C_{2-12}$alkenyl, and $C_{2-12}$alkynyl, wherein the $C_{1-12}$alkyl, $C_{2-12}$alkenyl, and $C_{2-12}$alkynyl are each optionally substituted with one to six $R^{17}$; $R^{35}$, in each occurrence, is independently selected from halo, —OH, —CN, $C_{1-12}$alkyl, $C_{2-12}$alkenyl, $C_{2-12}$alkynyl, and $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{30a}$ or $R^{30b}$, is independently selected from halo, —CN, —OH, $C_{1-6}$alkyl, and $C_{1-6}$alkoxy, wherein the $C_{1-6}$alkyl and $C_{1-6}$alkoxy are each optionally substituted with one to six halo; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first and/or thirty-second embodiments.

In a thirty-fourth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{3a}$ and $R^{3b}$ are each independently halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first and/or thirty-second embodiments.

In a thirty-fifth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{3a}$ and $R^{3b}$ are each independently $C_{1-6}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first and/or thirty-second embodiments.

In a thirty-sixth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{3a}$ and $R^{3b}$ are each independently $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first and/or thirty-second embodiments.

In a thirty-seventh embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^{3a}$ and $R^{3b}$ are each methyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first and/or thirty-second embodiments.

In a thirty-eighth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^4$ is H, halo, —CN, —OR$^{4a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{45}$; $R^{4a}$ is selected from H, $C_{1-12}$alkyl, $C_{2-12}$alkenyl, and $C_{2-12}$alkynyl, wherein the $C_{1-12}$alkyl, $C_{2-12}$alkenyl, and $C_{2-12}$alkynyl are each optionally substituted with one to six $R^{17}$; $R^{45}$, in each occurrence, is independently selected from halo, —OH, —CN, $C_{1-12}$alkyl, $C_{2-12}$alkenyl, $C_{2-12}$alkynyl, and $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{4a}$, is independently selected from halo, —CN, —OH, $C_{1-6}$alkyl, and $C_{1-6}$alkoxy, wherein the $C_{1-6}$alkyl and $C_{1-6}$alkoxy are each optionally substituted with one to six halo; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth and/or thirty-seventh embodiments.

In a thirty-ninth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^4$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth and/or thirty-seventh embodiments.

In a fortieth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^4$ is H or $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth and/or thirty-seventh embodiments.

In a forty-first embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^4$ is $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth and/or thirty-seventh embodiments.

In a forty-second embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^5$ is H, halo, —CN, —OR$^{5a}$, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight $R^{55}$; $R^{5a}$ is selected from H, $C_{1-12}$alkyl, $C_{2-12}$alkenyl, and $C_{2-12}$alkynyl, wherein the $C_{1-12}$alkyl, $C_{2-12}$alkenyl, and $C_{2-12}$alkynyl are each optionally substituted with one to six $R^{17}$; $R^{55}$, in each occurrence, is independently selected from halo, —OH, —CN, $C_{1-12}$alkyl, $C_{2-12}$alkenyl, $C_{2-12}$alkynyl, and $C_{1-12}$alkoxy, wherein the $C_{1-12}$alkyl, $C_{2-12}$alkenyl, $C_{2-12}$alkynyl, and $C_{1-12}$alkoxy are each optionally substituted with one to eight groups independently selected from halo, —OH, and $C_{1-4}$alkoxy; and $R^{17}$, in each occurrence, as an optional substituent of $R^{5a}$, is independently selected from halo, —CN, —OH, $C_{1-6}$alkyl, and $C_{1-6}$alkoxy, wherein the $C_{1-6}$alkyl and $C_{1-6}$alkoxy are each optionally substituted with one to six halo; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first and/or embodiments.

In a forty-third embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^5$ is H, halo, —OH, —CN, $C_{1-6}$alkyl or $C_{1-6}$alkoxy, wherein the $C_{1-6}$alkyl and $C_{1-6}$alkoxy are each optionally substituted by one to six groups independently selected from halo, —CN, —OH, and $C_{1-4}$alkoxy; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first and/or embodiments.

In a forty-fourth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^5$ is H or $C_{1-4}$alkyl; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first and/or embodiments.

In a forty-fifth embodiment of the invention, the compound is represented by Formula I, II, IIA, IIB, IIC, IID, III, IIIA, IIIB, IIIC, IIID, IV, IVA, IVB, V, VA, VB, VC, VD, VI, VIA, VIB, VIC, VID, VII, VIIA, VIIB, VIIC, VIID, VIII, VIIIA, VIIIB, XI, XIA, XIB, X, XA or XB or a pharmaceutically acceptable salt thereof, wherein $R^5$ is H; and wherein the values of the other variables are as defined for the first, fourth, fifth, sixth, eleventh, twelfth, thirteenth, fourteenth, fifteenth, sixteenth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth, thirty-ninth, fortieth, forty-first and/or embodiments.

In a forty-sixth embodiment of the invention, the compound is represented by Formula I, II, IIA, IIB, IIC, IID, V, VA, VB, VC, VD, VI, VIA, VIB, VIC, VID, VII, VIIA, VIIB, VIIC or VIID or a pharmaceutically acceptable salt thereof, wherein $R^1$ is —CN or —$CF_3$; $R^2$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, $C_{1-4}$alkyl, and $C_{1-4}$alkoxy; $R^{3a}$ and $R^{3b}$ are each independently halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; $R^4$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; X is —C(O)—,

or —$C(R^9)_2$—, wherein $R^9$, in each occurrence, is independently H, halo, —CN, —OH, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight groups independently selected from halo, —OH, —CN, and $C_{1-4}$alkoxy; bonds "a" and "b" are each a single bond; $R^5$ is H, halo, —OH, —CN, $C_{1-6}$alkyl or $C_{1-6}$alkoxy, wherein the $C_{1-6}$alkyl and $C_{1-6}$alkoxy are each optionally substituted by one to six groups independently selected from halo, —CN, —OH, and $C_{1-4}$alkoxy; $X^1$ is $C(R^6)_2$, wherein $R^6$, in each occurrence, is independently H, halo, $C_{1-6}$alkyl, —$OR^{6a}$, —$N(R^{6a})_2$, —$N(R^{6a})S(O)_2R^{6a}$, —$N(R^{6a})C(O)R^{6a}$, a 3 to 8-membered carbocyclyl or a 5 to 10-membered heterocyclyl; or the two $R^6$ groups, taken together, are oxo, $C_{1-6}$ alkylidene or

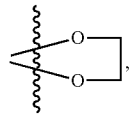

wherein the $C_{1-6}$alkyl, 3 to 8-membered carbocyclyl, 5 to 10-membered heterocyclyl, $C_{1-6}$ alkylidene, and

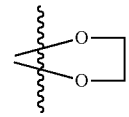

are each optionally substituted with one to six $R^{65}$; $R^{6a}$, in each occurrence, is independently H, $C_{1-6}$alkyl, $C_{1-6}$acyl, 3 to 10-membered carbocyclyl or 3 to 10-membered heterocyclyl, wherein $C_{1-6}$alkyl, 3 to 10-membered carbocyclyl and 3 to 10-membered heterocyclyl are each optionally substituted with one to four $R^{17}$; $R^{65}$, in each occurrence, is independently 3 to 10-membered carbocyclyl or halo, wherein the 3 to 10-membered carbocyclyl is optionally substituted with one to four groups independently selected from halo, —OH, and $C_{1-6}$alkoxy; and $R^{17}$, in each occurrence, is as an optional substituent of $R^{6a}$, independently a 3 to 10-membered carbocyclyl, halo, —OH, $C_{1-4}$alkoxy or —CN; $X^2$ is $C(R^7)_2$, wherein $R^7$, in each occurrence, is independently H or $C_{1-6}$alkyl, wherein $C_{1-6}$alkyl is optionally substituted with one to six groups independently selected from halo, —OH, $C_{1-6}$alkoxy, and —CN; and $X^3$ is $C(R^8)_2$, wherein $R^8$, in each occurrence, is independently H, halo, —CN, —OH, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight groups independently selected from halo, —OH, —CN, and $C_{1-4}$alkoxy.

In a forty-seventh embodiment of the invention, the compound is represented by Formula I, II, IIA, IIB, IIC, IID, V, VA, VB, VC, VD, VI, VIA, VIB, VIC, VID, VII, VIIA, VIIB, VIIC or VIID or a pharmaceutically acceptable salt thereof, wherein $R^1$ is —CN; $R^2$ is H or $C_{1-4}$alkyl; $R^{3a}$ and $R^{3b}$ are each independently $C_{1-6}$alkyl; $R^4$ is H or $C_{1-4}$alkyl; X is —C($R^9$)$_2$—, wherein $R^9$, in each occurrence, is independently H or $C_{1-4}$alkyl; bonds "a" and "b" are each a single bond; $R^5$ is H or $C_{1-4}$alkyl; $X^1$ is C($R^6$)$_2$, wherein $R^6$, in each occurrence, is independently H, halo, $C_{1-4}$alkyl, phenyl, 1,2,3,4-tetrahydroisoquinolinyl, pyrrolidinyl, morpholinyl, pyridyl, —O$R^{6a}$, —N($R^{6a}$)$_2$, —N($R^{6a}$)S(O)$_2R^{6a}$ or —N($R^{6a}$)C(O)$R^{6a}$; or the two $R^6$ groups, taken together, are oxo, $C_{1-4}$ alkylidene or

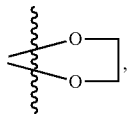

wherein the $C_{1-4}$alkyl, phenyl, 1,2,3,4-tetrahydroisoquinolinyl, pyrrolidinyl, morpholinyl, pyridyl, $C_{1-4}$ alkylidene, and

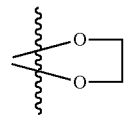

are each optionally substituted with one to four $R^{65}$; $R^{6a}$, in each occurrence, is independently H, $C_{1-4}$alkyl, 3 to 8-membered cycloalkyl or phenyl, wherein $C_{1-4}$alkyl, $C_{1-4}$acyl, and phenyl are each optionally substituted with one to three $R^{17}$; $R^{65}$, in each occurrence, is independently phenyl or halo; and $R^{17}$, in each occurrence, as an optional substituent of $R^{6a}$, is independently phenyl; $X^2$ is C($R^7$)$_2$, wherein $R^7$, in each occurrence, is independently H or $C_{1-4}$alkyl; and $X^3$ is C($R^8$)$_2$, wherein $R^8$, in each occurrence, is independently H or $C_{1-4}$alkyl.

In a forty-eighth embodiment of the invention, the compound is represented by Formula I, II, IIA, IIB, IIC, IID, V, VA, VB, VC, VD, VI, VIA, VIB, VIC, VID, VII, VIIA, VIIB, VIIC or VIID or a pharmaceutically acceptable salt thereof, wherein $R^1$ is —CN; $R^2$ is H; $R^{3a}$ and $R^{3b}$ are each independently $C_{1-4}$alkyl; $R^4$ is $C_{1-4}$alkyl; X is —CH$_2$—; bonds "a" and "b" are each a single bond; $R^5$ is H; $X^1$ is C($R^6$)$_2$, wherein one $R^6$ group is H, $C_{1-4}$alkyl, benzyl, phenyl, halo, —OH, $C_{1-4}$alkoxy, —NH$_2$, —NHCH$_3$, —N(CH$_3$)$_2$, —NHCH$_2$Ph, —N(CH$_3$)CH$_2$Ph, —NHS(O)$_2$Ph, —NHC(O)$R^{6a}$,

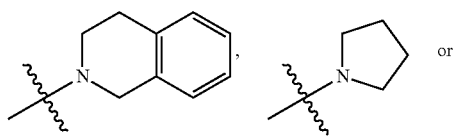

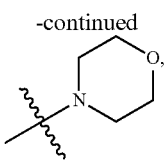

wherein $R^{6a}$, as an optional substituent of $R^x$, is $C_{1-4}$alkyl, cyclohexyl or phenyl; and the other $R^6$ group is H, $C_{1-4}$alkyl, CF$_3$, benzyl, phenyl, halo, —OH, $C_{1-4}$alkoxy, —NHCH$_2$CF$_3$,

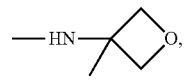

—NHC(O)$R^{6a}$, —N(CH$_3$)C(O)$R^{6a}$ or pyridyl, wherein $R^{6a}$, as an optional substituent of $R^y$, is $C_{1-4}$alkyl or phenyl; or the two $R^6$ groups, taken together, are oxo,

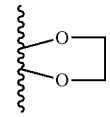

or $C_{1-4}$ alkylidene, wherein $C_{1-4}$ alkylidene is optionally substituted with phenyl; $X^2$ is —CH$_2$—; and $X^3$ is —CH$_2$—.

In a forty-ninth embodiment of the invention, the compound is represented by Formula I, II, IIA, IIB, IIC, IID, V, VA, VB, VC, VD, VI, VIA, VIB, VIC, VID, VII, VIIA, VIIB, VIIC or VIID or a pharmaceutically acceptable salt thereof, wherein $R^1$ is —CN; $R^2$ is H or $C_{1-4}$alkyl; $R^{3a}$ and $R^{3b}$ are each independently $C_{1-6}$alkyl; $R^4$ is H or $C_{1-4}$alkyl; X is —C(O)— or

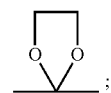

bonds "a" and "b" are each a single bond; $R^5$ is H or $C_{1-4}$alkyl; $X^1$ is C($R^6$)$_2$, wherein $R^6$, in each occurrence, is independently H or $C_{1-4}$alkyl; $X^2$ is C($R^7$)$_2$, wherein $R^7$, in each occurrence, is independently H or $C_{1-4}$alkyl; and $X^3$ is C($R^8$)$_2$, wherein $R^8$, in each occurrence, is independently H or $C_{1-4}$alkyl.

In a fiftieth embodiment of the invention, the compound is represented by Formula I, II, IIA, IIB, IIC, IID, V, VA, VB, VC, VD, VI, VIA, VIB, VIC, VID, VII, VIIA, VIIB, VIIC or VIID or a pharmaceutically acceptable salt thereof, wherein $R^1$ is —CN; $R^2$ is H; $R^{3a}$ and $R^{3b}$ are each independently $C_{1-4}$alkyl; $R^4$ is $C_{1-4}$alkyl; X is —C(O)— or

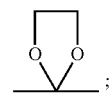

bonds "a" and "b" are each a single bond; $R^5$ is H; $X^1$ is —CH$_2$—; $X^2$ is —CHR$^7$—, wherein $R^7$ is H or $C_{1-4}$alkyl; and $X^3$ is —CH$_2$—.

In a fifty-first embodiment of the invention, the compound is represented by Formula I, III, IIIA, IIIB, IIIC or IIID or a pharmaceutically acceptable salt thereof, wherein $R^1$ is —CN or —CF$_3$; $R^2$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, $C_{1-4}$alkyl, and $C_{1-4}$alkoxy; $R^{3a}$ and $R^{3b}$ are each independently $C_{1-12}$alkyl optionally substituted with one to three groups independently selected from halo, $C_{1-4}$alkoxy, —CN, and —OH; $R^4$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; X is —C(O)—,

or —C(R$^9$)$_2$—, wherein R$^9$, in each occurrence, is independently H, halo, —CN, —OH, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight groups independently selected from halo, —OH, —CN, and $C_{1-4}$alkoxy; bond "a" is a double bond and "b" is a single bond; $R^5$ is H, halo, —OH, —CN, $C_{1-6}$alkyl or $C_{1-6}$alkoxy, wherein the $C_{1-6}$alkyl and $C_{1-6}$alkoxy are each optionally substituted by one to six groups independently selected from halo, —CN, —OH, and $C_{1-4}$alkoxy; $X^1$ is $CR^6$, wherein $R^6$, in each occurrence, is independently H, halo, $C_{1-6}$alkyl, —OR$^{6a}$, —N(R$^{6a}$)$_2$, —N(R$^{6a}$)S(O)$_2$R$^{6a}$, —N(R$^{6a}$)C(O)R$^{6a}$, a 3 to 8-membered carbocyclyl or a 5 to 10-membered heterocyclyl, wherein the $C_{1-6}$alkyl, 3 to 8-membered carbocyclyl, and 5 to 10-membered heterocyclyl are each optionally substituted with one to six R$^{65}$; R$^{6a}$, in each occurrence, is independently H, $C_{1-6}$alkyl, $C_{1-6}$acyl or 3 to 10-membered carbocyclyl, wherein $C_{1-6}$alkyl and 3 to 10-membered carbocyclyl are each optionally substituted with one to four R$^{17}$; R$^{65}$, in each occurrence, is independently 3 to 10-membered carbocyclyl or halo, wherein the 3 to 10-membered carbocyclyl is optionally substituted with one to four groups independently selected from halo, —OH, and $C_{1-6}$alkoxy; and R$^{17}$, in each occurrence, as an optional substituent of R$^{6a}$, is independently a 3 to 10-membered carbocyclyl, halo, —OH, $C_{1-4}$alkoxy or —CN; $X^2$ is $CR^7$, wherein $R^7$, in each occurrence, is independently H or $C_{1-6}$alkyl, wherein $C_{1-6}$alkyl is optionally substituted with one to six groups independently selected from halo, —OH, $C_{1-6}$alkoxy, and —CN; and $X^3$ is $C(R^8)_2$, wherein $R^8$, in each occurrence, is independently H, halo, —CN, —OH, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight groups independently selected from halo, —OH, —CN, and $C_{1-4}$alkoxy.

In a fifty-second embodiment of the invention, the compound is represented by Formula I, III, IIIA, IIIB, IIIC or IIID or a pharmaceutically acceptable salt thereof, wherein $R^1$ is —CN; $R^2$ is H or $C_{1-4}$alkyl; $R^{3a}$ and $R^{3b}$ are each independently $C_{1-4}$alkyl; $R^4$ is H or $C_{1-4}$alkyl; X is —C(R$^9$)$_2$—, wherein R$^9$, in each occurrence, is independently H or $C_{1-4}$alkyl; bond "a" is a double bond and "b" is a single bond; $R^5$ is H or $C_{1-4}$alkyl; $X^1$ is $CR^6$, wherein $R^6$, in each occurrence, is independently H, $C_{1-4}$alkyl, phenyl or pyridyl, wherein the $C_{1-4}$alkyl, phenyl, and pyridyl are each optionally substituted with one to four groups independently selected from phenyl and halo; $X^2$ is $CR^7$, wherein $R^7$, in each occurrence, is independently H or $C_{1-4}$alkyl; and $X^3$ is $C(R^8)_2$, wherein $R^8$, in each occurrence, is independently H or $C_{1-4}$alkyl.

In a fifty-third embodiment of the invention, the compound is represented by Formula I, III, IIIA, IIIB, IIIC or IIID or a pharmaceutically acceptable salt thereof, wherein $R^1$ is —CN; $R^2$ is H; $R^{3a}$ and $R^{3b}$ are each independently $C_{1-4}$alkyl; $R^4$ is $C_{1-4}$alkyl; X is —CH$_2$—; bond "a" is a double bond and "b" is a single bond; $R^5$ is H; $X^1$ is —CR$^6$—, wherein $R^6$ is H, —CH$_3$, benzyl, phenyl or pyridyl; $X^2$ is —CH$_2$—; and $X^3$ is —CH$_2$—.

In a fifty-fourth embodiment of the invention, the compound is represented by Formula I, IV, IVA, IVB, VIII, VIIIA, VIIIB, XI, XIA, XIB, X, XA or XB or a pharmaceutically acceptable salt thereof, wherein $R^1$ is —CN or —CF$_3$; $R^2$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, $C_{1-4}$alkyl, and $C_{1-4}$alkoxy; $R^{3a}$ and $R^{3b}$ are each independently $C_{1-12}$alkyl optionally substituted with one to three groups independently selected from halo, $C_{1-4}$alkoxy, —CN, and —OH; $R^4$ is H, halo, —OH, —CN, $C_{1-6}$alkyl or $C_{1-6}$alkoxy, wherein the $C_{1-6}$alkyl and $C_{1-6}$alkoxy are each optionally substituted with one to six groups independently selected from halo, —CN, —OH, and $C_{1-4}$alkoxy; X is —C(O)—,

or —C(R$^9$)$_2$—, wherein R$^9$, in each occurrence, is independently H, halo, —CN, —OH, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to eight groups independently selected from halo, —OH, —CN, and $C_{1-4}$alkoxy; bond "a" is a single bond and "b" is a double bond; $R^5$ is absent; $X^1$ is $C(R^6)_2$, wherein $R^6$, in each occurrence, is independently H, halo, $C_{1-6}$alkyl, —OR$^{6a}$, —N(R$^{6a}$)$_2$, —N(R$^{6a}$)S(O)$_2$R$^{6a}$, —N(R$^{6a}$)C(O)R$^{6a}$, a 3 to 8-membered carbocyclyl or a 5 to 10-membered heterocyclyl; or the two R$^6$ groups, taken together, are oxo, $C_{1-6}$ alkylidene or

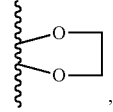

wherein the $C_{1-6}$alkyl, 3 to 8-membered carbocyclyl, 5 to 10-membered heterocyclyl, $C_{1-6}$ alkylidene, and

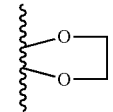

are each optionally substituted with one to six R$^{65}$; R$^{6a}$; in each occurrence, is independently H, $C_{1-6}$alkyl, $C_{1-6}$acyl or 3 to 10-membered carbocyclyl, wherein $C_{1-6}$alkyl and 3 to 10-membered carbocyclyl are each optionally substituted with one to four R$^{17}$; R$^{65}$, in each occurrence, is independently 3 to 10-membered carbocyclyl or halo, wherein the 3 to 10-membered carbocyclyl is optionally substituted with one to four groups independently selected from halo, —OH, and C$_{1-6}$alkoxy; and R$^{17}$, in each occurrence, as an optional substituent of R$^{6a}$, is independently a 3 to 10-membered carbocyclyl, halo, —OH, C$_{1-4}$alkoxy or —CN; X$^2$ is C(R$^7$)$_2$, wherein R$^7$, in each occurrence, is independently H or C$_{1-6}$alkyl, wherein C$_{1-6}$alkyl is optionally substituted with one to six groups independently selected from halo, —OH, C$_{1-6}$alkoxy, and —CN; and X$^3$ is CR$^8$, wherein R$^8$, in each occurrence, is independently H, halo, —CN, —OH, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight groups independently selected from halo, —OH, —CN, and C$_{1-4}$alkoxy.

In a fifty-fifth embodiment of the invention, the compound is represented by Formula I, IV, IVA, IVB, VIII, VIIIA, VIIIB, XI, XIA, XIB, X, XA or XB or a pharmaceutically acceptable salt thereof, wherein R$^1$ is —CN; R$^2$ is H or C$_{1-4}$alkyl; R$^{3a}$ and R$^{3b}$ are each independently C$_{1-6}$alkyl; R$^4$ is H or C$_{1-4}$alkyl; X is —C(O)— or —C(R$^9$)$_2$—, wherein R$^9$, in each occurrence, is independently H or C$_{1-4}$alkyl; bond "a" is a single bond and "b" is a double bond; R$^5$ is absent; X$^1$ is C(R$^6$)$_2$, wherein the two R$^6$ groups, taken together, are oxo, C$_{1-4}$ alkylidene or

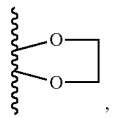, wherein the C$_{1-4}$ alkylidene and

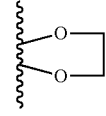

are each optionally substituted with one to four R$^{65}$; R$^{6a}$, in each occurrence, is independently H, C$_{1-4}$alkyl, 3 to 8-membered cycloalkyl or phenyl, wherein C$_{1-4}$alkyl, C$_{1-4}$acyl, and phenyl are each optionally substituted with one to three R$^{17}$; R$^{65}$, in each occurrence, is independently phenyl or halo; and R$^{17}$, in each occurrence, as an optional substituent of R$^{6a}$, is independently phenyl; X$^2$ is C(R$^7$)$_2$, wherein R$^7$, in each occurrence, is independently H or C$_{1-4}$alkyl; and X$^3$ is CR$^8$, wherein R$^8$, in each occurrence, is independently H or C$_{1-4}$alkyl.

In a fifty-sixth embodiment of the invention, the compound is represented by Formula I, IV, IVA, IVB, VIII, VIIIA, VIIIB, XI, XIA, XIB, X, XA or XB or a pharmaceutically acceptable salt thereof, wherein R$^1$ is —CN; R$^2$ is H; R$^{3a}$ and R$^{3b}$ are each independently C$_{1-4}$alkyl; R$^4$ is C$_{1-4}$alkyl; X is —CH$_2$— or oxo; bond "a" is a single bond and "b" is a double bond; X$^1$ is —CH$_2$— or —C(R$^6$)$_2$, wherein two R$^6$, taken together, are oxo or

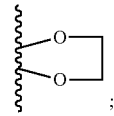;

X$^2$ is —CHR$^7$—, wherein R$^7$ is H or C$_{1-4}$alkyl; and X$^3$ is —CH$_2$—.

In a fifty-seventh embodiment of the invention, the compound is selected from the group consisting of:
(4'aR,8'aS)-4',4',8'a-trimethyl-3'-oxo-spiro[1,3-dioxolane-2, 7'-4a,5,6,8-tetrahydronaphthalene]-2'-carbonitrile,
(4aS,8aS)-4,4,8a-trimethyl-3,8-dioxo-4a,5,6,7-tetrahydronaphthalene-2-carbonitrile,
(4aR,8aS)-4,4,8a-trimethyl-3-oxo-5,6,7,8-tetrahydro-4aH-naphthalene-2-carbonitrile,
(4aR,8aS)-4,4,7,7,8a-pentamethyl-3-oxo-4a,5,6,8-tetrahydronaphthalene-2-carbonitrile,
(4aS,7S,8aS)-7-hydroxy-4,4,8a-trimethyl-3-oxo-5,6,7,8-tetrahydro-4aH-naphthalene-2-carbonitrile,
(4aS,7S,8aS)-7-methoxy-4,4,8a-trimethyl-3-oxo-5,6,7,8-tetrahydro-4aH-naphthalene-2-carbonitrile,
(4aS,8aS)-7,7-difluoro-4,4,8a-trimethyl-3-oxo-4a,5,6,8-tetrahydronaphthalene-2-carbonitrile,
(4aS,7R,8aS)-7-hydroxy-4,4,8a-trimethyl-3-oxo-5,6,7,8-tetrahydro-4aH-naphthalene-2-carbonitrile,
(8'aS)-4',4',8'a-trimethyl-3'-oxo-spiro[1,3-dioxolane-2,7'-6,8-dihydronaphthalene]-2'-carbonitrile,
(4aR,8aS)-4,4,8a-trimethyl-7-methylene-3-oxo-4a,5,6,8-tetrahydronaphthalene-2-carbonitrile,
(8aS)-4,4,8a-trimethyl-3,7-dioxo-6,8-dihydronaphthalene-2-carbonitrile,
(4aS,6S,8aS)-4,4,6,8a-tetramethyl-3,8-dioxo-4a,5,6,7-tetrahydronaphthalene-2-carbonitrile,
(4aS,6S,8aS)-6-ethyl-4,4,8a-trimethyl-3,8-dioxo-4a,5,6,7-tetrahydronaphthalene-2-carbonitrile,
(4aS,7S,8aS)-7-hydroxy-4,4,7,8a-tetramethyl-3-oxo-4a,5,6,8-tetrahydronaphthalene-2-carbonitrile,
(4aS,6R,8aS)-4,4,6,8a-tetramethyl-3,8-dioxo-4a,5,6,7-tetrahydronaphthalene-2-carbonitrile,
(4aS,8aS)-4,4,7,8a-tetramethyl-3-oxo-5,8-dihydro-4aH-naphthalene-2-carbonitrile,
(4aS,7S,8aS)-7-hydroxy-4,4,8a-trimethyl-3-oxo-7-(trifluoromethyl)-4a,5,6,8-tetrahydronaphthalene-2-carbonitrile,
(4aS,7R,8aS)-7-benzyl-4,4,8a-trimethyl-3-oxo-5,6,7,8-tetrahydro-4aH-naphthalene-2-carbonitrile,
(4aS,7R,8aS)-7-methoxy-4,4,8a-trimethyl-3-oxo-5,6,7,8-tetrahydro-4aH-naphthalene-2-carbonitrile,
(4aR,7E,8aS)-7-benzylidene-4,4,8a-trimethyl-3-oxo-4a,8-dihydronaphthalene-2-carbonitrile,
(6R,8aS)-6-ethyl-4,4,8a-trimethyl-3,8-dioxo-4a,5,6,7-tetrahydronaphthalene-2-carbonitrile,
(4aS,7R,8aS)-7-fluoro-4,4,8a-trimethyl-3-oxo-5,6,7,8-tetrahydro-4aH-naphthalene-2-carbonitrile,
(4aS,8aS)-4,4,8a-trimethyl-3-oxo-5,8-dihydro-4aH-naphthalene-2-carbonitrile,
(4aS,7R,8aS)-7-benzyl-7-hydroxy-4,4,8a-trimethyl-3-oxo-4a,5,6,8-tetrahydronaphthalene-2-carbonitrile,
(4aS,7S,8aS)-7-methoxy-4,4,7,8a-tetramethyl-3-oxo-4a,5,6,8-tetrahydronaphthalene-2-carbonitrile,
(4aS,8aS)-7-benzyl-4,4,8a-trimethyl-3-oxo-5,8-dihydro-4aH-naphthalene-2-carbonitrile,
(4aS,7R,8aS)-7-benzyl-7-methoxy-4,4,8a-trimethyl-3-oxo-4a,5,6,8-tetrahydronaphthalene-2-carbonitrile,
N-[(2S,4aS,8aS)-7-cyano-5,5,8a-trimethyl-6-oxo-2,3,4,4a-tetrahydro-1H-naphthalen-2-yl]acetamide, (4aR,7E,8aS)-7-benzylidene-4,4,8a-trimethyl-3-oxo-4a,5,6,8-tetrahydronaphthalene-2-carbonitrile,
(4aS,7S,8aS)-7-hydroxy-4,4,8a-trimethyl-3-oxo-7-phenyl-4a,5,6,8-tetrahydronaphthalene-2-carbonitrile,
(4aS,8aS)-4,4,8a-trimethyl-3-oxo-7-phenyl-5,8-dihydro-4aH-naphthalene-2-carbonitrile,
(4aS,7R,8aS)-7-hydroxy-4,4,8a-trimethyl-3-oxo-7-(3-pyridyl)-4a,5,6,8-tetrahydronaphthalene-2-carbonitrile hydrochloride,
(4aS,7S,8aS)-4,4,8a-trimethyl-3-oxo-7-phenyl-5,6,7,8-tetrahydro-4aH-naphthalene-2-carbonitrile,
(4aS,7S,8aS)-4,4,8a-trimethyl-7-(methylamino)-3-oxo-5,6,7,8-tetrahydro-4aH-naphthalene-2-carbonitrile hydrochloride,
(4aS,7S,8aS)-4,4,8a-trimethyl-7-morpholino-3-oxo-5,6,7,8-tetrahydro-4aH-naphthalene-2-carbonitrile,
(4aS,7S,8aS)-7-(benzylamino)-4,4,8a-trimethyl-3-oxo-5,6,7,8-tetrahydro-4aH-naphthalene-2-carbonitrile,
(6S,8aS)-4,4,6,8a-tetramethyl-3,8-dioxo-6,7-dihydronaphthalene-2-carbonitrile,
(4aS,8aS)-4,4,8a-trimethyl-3-oxo-7-(3-pyridyl)-5,8-dihydro-4aH-naphthalene-2-carbonitrile hydrochloride,
(4aS,7S,8aS)-4,4,8a-trimethyl-3-oxo-7-pyrrolidin-1-yl-5,6,7,8-tetrahydro-4aH-naphthalene-2-carbonitrile,
(4aR,7S,8aS)-7-(3,4-dihydro-1H-isoquinolin-2-yl)-4,4,8a-trimethyl-3-oxo-5,6,7,8-tetrahydro-4aH-naphthalene-2-carbonitrile,
(4aS,7S,8aS)-7-amino-4,4,8a-trimethyl-3-oxo-5,6,7,8-tetrahydro-4aH-naphthalene-2-carbonitrile hydrochloride,
N-[(2S,4aS,8aS)-7-cyano-5,5,8a-trimethyl-6-oxo-2,3,4,4a-tetrahydro-1H-naphthalen-2-yl]benzamide,
N-[(2S,4aS,8aS)-7-cyano-5,5,8a-trimethyl-6-oxo-2,3,4,4a-tetrahydro-1H-naphthalen-2-yl]cyclohexanecarboxamide,
N-[(2S,4aS,8aS)-7-cyano-5,5,8a-trimethyl-6-oxo-2,3,4,4a-tetrahydro-1H-naphthalen-2-yl]benzenesulfonamide,
(4aS,7S,8aS)-7-[benzyl(methyl)amino]-4,4,8a-trimethyl-3-oxo-5,6,7,8-tetrahydro-4aH-naphthalene-2-carbonitrile,
(4aS,7S,8aS)-7-(dimethylamino)-4,4,8a-trimethyl-3-oxo-5,6,7,8-tetrahydro-4aH-naphthalene-2-carbonitrile hydrochloride,
(4aR,8aR)-4,4,8a-trimethyl-3,7-dioxo-4a,5,6,8-tetrahydronaphthalene-2-carbonitrile,
(4aR,7S,8aR)-7-hydroxy-4,4,8a-trimethyl-3-oxo-7-phenyl-4a,5,6,8-tetrahydronaphthalene-2-carbonitrile,
(4aR,7R,8aR)-7-hydroxy-4,4,7,8a-tetramethyl-3-oxo-4a,5,6,8-tetrahydronaphthalene-2-carbonitrile,
(4aR,8aR)-7,7-difluoro-4,4,8a-trimethyl-3-oxo-4a,5,6,8-tetrahydronaphthalene-2-carbonitrile,
(4aR,7R,8aR)-7-benzyl-7-hydroxy-4,4,8a-trimethyl-3-oxo-4a,5,6,8-tetrahydronaphthalene-2-carbonitrile,
(4aR,8aR)-4,4,7,8a-tetramethyl-3-oxo-5,8-dihydro-4aH-naphthalene-2-carbonitrile,
(4aR,7R,8aR)-7-methoxy-4,4,7,8a-tetramethyl-3-oxo-4a,5,6,8-tetrahydronaphthalene-2-carbonitrile,
(4aR,8aR)-4,4,8a-trimethyl-3-oxo-7-phenyl-5,8-dihydro-4aH-naphthalene-2-carbonitrile,
(4aR,8aR)-4,4,8a-trimethyl-7-methylene-3-oxo-4a,5,6,8-tetrahydronaphthalene-2-carbonitrile,
(4aR,8aR)-4,4,8a-trimethyl-3-oxo-5,8-dihydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]-N-methyl-benzamide,
(4aS,7R,8aR)-4,4,8a-trimethyl-7-[(3-methyloxetan-3-yl)amino]-3-oxo-5,6,7,8-tetrahydro-4aH-naphthalene-2-carbonitrile,
(4aR,7R,8aR)-7-hydroxy-4,4,8a-trimethyl-3-oxo-5,6,7,8-tetrahydro-4aH-naphthalene-2-carbonitrile,
(4aR,7S,8aR)-7-hydroxy-4,4,8a-trimethyl-3-oxo-5,6,7,8-tetrahydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]acetamide,
(4aS,7R,8aR)-4,4,8a-trimethyl-3-oxo-7-(2,2,2-trifluoroethylamino)-5,6,7,8-tetrahydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]-N-methyl-acetamide,
N-[(2R,4aS,8aR)-7-cyano-5,5,8a-trimethyl-6-oxo-2,3,4,4a-tetrahydro-1H-naphthalen-2-yl]benzamide,
(4aR,7S,8aR)-7-methoxy-4,4,8a-trimethyl-3-oxo-5,6,7,8-tetrahydro-4aH-naphthalene-2-carbonitrile,
N-[(1R,4aS,8aS)-7-cyano-5,5,8a-trimethyl-6-oxo-2,3,4,4a-tetrahydro-1H-naphthalen-1-yl]acetamide,
N-[(1S,4aS,8aS)-7-cyano-5,5,8a-trimethyl-6-oxo-2,3,4,4a-tetrahydro-1H-naphthalen-1-yl]acetamide, and
(4aR,8aS)-4,4,8a-trimethyl-3,8-dioxo-4a,5,6,7-tetrahydronaphthalene-2-carbonitrile, or a pharmaceutically acceptable salt thereof.

As used herein, the term "alkyl" refers to a fully saturated branched or unbranched hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkylene" refers to a bivalent saturated hydrocarbon of 1-6 carbon atoms, wherein the alkylene group is attached with two σ-bonds, with two saturated carbon atoms as the points of attachment. An alkylene is a linear or branched acyclic structure. The groups, —CH$_2$— (methylene), —CH$_2$CH$_2$—, —CH$_2$C(CH$_3$)$_2$CH$_2$— and —CH$_2$CH$_2$CH$_2$—, are non-limiting examples of alkylene groups.

As used herein, the term "alkenyl" refers to an unsaturated hydrocarbon group which may be linear or branched and has at least one carbon-carbon double bond. Alkenyl groups with 2-12 carbon atoms or 2-6 carbon atoms are preferred. The alkenyl group may contain 1, 2 or 3 carbon-carbon double bonds, or more. Preferably, alkenyl groups contain one or two double bonds, most preferably one double bond. Examples of alkenyl groups include ethenyl, n-propenyl, isopropenyl, n-but-2-enyl, n-hex-3-enyl and the like.

As used herein, the term "alkenylene" refers to a bivalent unsaturated hydrocarbon of 1-6 carbon atoms, wherein the alkenylene group is attached with two σ-bonds, with two carbon atoms as points of attachment. An alkenylene is linear or branched acyclic structure having at least one nonaromatic carbon-carbon double bond with no carbon-carbon triple bonds and no atoms other than carbon and hydrogen. The groups, —CH═CH—, —CH═C(CH$_3$)CH$_2$— and —CH═CHCH$_2$—, are non-limiting examples of alkenylene groups.

As used herein, the term "alkynyl" refers to an unsaturated hydrocarbon group which is linear or branched and has at least one carbon-carbon triple bond. Alkynyl groups with 2-12 carbon atoms or 2-6 carbon atoms can be preferred. The alkynyl group may contain 1, 2 or 3 carbon-carbon triple bonds, or more. Preferably, alkynyl groups contain one or two triple bonds, most preferably one triple bond. Examples of alkynyl groups include ethynyl, n-propynyl, n-but-2-ynyl, n-hex-3-ynyl and the like.

As used herein, the term "alkynylene" refers to a bivalent unsaturated hydrocarbon of 1-6 carbon atoms, wherein the alkynylene group is attached with two σ-bonds, with two carbon atoms as points of attachment. An alkynylene is a linear or branched acyclic structure having at least one carbon-carbon triple bond with no atoms other than carbon and hydrogen. The groups, —C≡C—, —C≡CCH$_2$— and —C≡CCH(CH$_3$)—, are non-limiting examples of alkynylene groups.

As used herein, the term "alkylidene" refers to a bivalent unsaturated hydrocarbon of 1-6 carbon atoms (=CRR'), wherein the alkylidene group is attached with one σ-bond and one π-bond, in which R and R' are independently hydrogen, alkyl, or R and R' are taken together to represent alkylene. Non-limiting examples of alkylidene groups include: =CH$_2$, =CH(CH$_2$CH$_3$) and =C(CH$_3$)$_2$.

As used herein, the term "acyl" refers to a monovalent group, —C(O)R with a carbon atom of a carbonyl group as the point of attachment. R is a linear or branched, cyclo, hydrocarbon, optionally substituted with halo, —OH, —CN, C$_{1-12}$alkyl, C$_{2-12}$alkenyl, C$_2$-12alkynyl or C$_{1-12}$alkoxy. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$ and —C(O)CH$_2$C$_6$H$_5$, are non-limiting examples of acyl groups. The term "acyl" therefore encompasses, but is not limited to, groups sometimes referred to as "alkyl carbonyl" and "aryl carbonyl" groups.

As used herein, the term "alkoxy" refers to the group —OR, in which R is a C$_{1-12}$alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopropyl, —O-cyclobutyl, —O—cyclopentyl and —O-cyclohexyl.

The number of carbon atoms in a group is specified herein by the prefix "C$_{x-xx}$", wherein x and xx are integers. For example, "C$_{1-4}$alkyl" is an alkyl group which has from 1 to 4 carbon atoms.

As used herein, the term "halogen" or "halo" may be fluoro, chloro, bromo or iodo.

As used herein, the term "heterocyclyl" refers to a saturated or unsaturated, monocyclic or bicyclic (e.g., bridged, fused or spiro) ring system which has from 3- to 12-ring members, or in particular 3- to 6-ring members or 5- to 7-ring members, at least one of which is a heteroatom, and up to 4 (e.g., 1, 2, 3 or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings and heterocyclic rings that is not aromatic (i.e., "non-aromatic heterocycles"). As used herein, the term "heteroaryl" refers to an aromatic 5 to 12 membered monocyclic or bicyclic ring system, having 1 to 4 heteroatoms independently selected from O, S and N, and wherein N can be oxidized (e.g., N(O)) or quaternized, and S can be optionally oxidized to sulfoxide and sulfone. A non-aromatic heterocyclyl refers to a saturated or unsaturated, monocyclic or bicyclic (e.g., bridged, fused or spiro) ring system which has from 3- to 12-ring members. For example, a non-aromatic heterocyclyl is a 3- to 7-membered saturated monocyclic or a 3- to 6-membered saturated monocyclic or a 5- to 7-membered saturated monocyclic ring. A non-aromatic heterocyclyl is a 3- to 7-membered unsaturated monocyclic or a 3- to 6-membered unsaturated monocyclic or a 5- to 7-membered unsaturated monocyclic ring. In another embodiment, a heterocyclyl is a 6 or 7-membered bicyclic ring. The heterocyclyl group can be attached at a heteroatom or a carbon atom. Examples of non-aromatic heterocyclyls include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and examples of heteroaryls including pyrrolyl, furanyl, imidazolyl, pyrazolyl, oxazolyl, isoxazolyl, thiazolyl, isothiazolyl, oxadiazolyl, thiadiazolyl, triazolyl, tetrazolyl, pyridyl, pyranyl, pyrazinyl, pyrimidyl, pyridazinyl, oxazinyl, thiazinyl, dioxinyl, triazinyl, tetrazinyl, azepinyl, oxepinyl, thiepinyl, thiazepinyl, 1-oxo-pyridyl, thienyl, valerolactamyl, azaindolyl, benzimidazolyl, benzo[1,4]dioxinyl, benzofuryl, benzoisoxazolyl, benzoisothiazolyl, benzothiadiazolyl, benzothiazolyl, benzothienyl, benzotriazolyl, benzoxadiazolyl, benzoxazolyl, cyclopentaimidazolyl, cyclopentatriazolyl, imidazo[1,2-a]pyridyl, indazolyl, indolizinyl, indolyl, isoquinolinyl, oxazolopyridinyl, purinyl, pyrazolo[3,4]pyrimidinyl, pyridopyazinyl, pyridopyrimidinyl, pyrrolo[2,3]pyrimidinyl, pyrrolopyrazolyl, pyrroloimidazolyl, pyrrolotriazolyl, quinazolinyl, quinolinyl, thiazolopyridinyl, and the like. Examples of bicyclic nonaromatic heterocyclic ring systems include benzo[1,3]dioxolyl, tetrahydroindolyl, and 2-azaspiro[3.3]heptanyl.

As used herein, the term "carbocyclyl" refers to saturated, partially unsaturated, or aromatic monocyclic or bicyclic hydrocarbon groups of 3-12 carbon atoms, 3-6 carbon atoms or 5-7 carbon atoms. The term "carbocyclyl" encompasses cycloalkyl groups and aromatic groups. The term "cycloalkyl" refers to completely saturated monocyclic or bicyclic (e.g., bridged, fused or spiro) hydrocarbon groups of 3-12 carbon atoms, 3-6 carbon atoms or 5-7 carbon atoms. "Aryl" refers to an aromatic 6-12 membered monocyclic or bicyclic ring system. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O or S. A bridged ring system may have 6-12 ring members. Exemplary bridged carbocyclyl groups include decahydro-2,7-methanonaphthyl, bicyclo[2.2.1]heptyl, bicyclo[2.1.1]hexyl, bicyclo[2.2.1]heptenyl, tricyclo[2.2.1.0$^{2,6}$]heptanyl, 6,6-dimethylbicyclo[3.1.1]heptyl, and 2,6,6-trimethylbicyclo[3.1.1]heptyl.

The term "fused ring system," as used herein, is a ring system that has a carbocyclyl or heterocyclyl ring wherein two adjacent atoms of the ring are connected (bridged) by one or more (preferably from one to three) atoms selected from C, N, O or S. A fused ring system may have from 4-10 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members. Exemplary sprio ring carbocyclyl groups include spiro[2.2]pentanyl and spiro[3.3]heptanyl.

Pharmaceutical acceptable salts of the compounds disclosed herein are also included in the invention. In cases where a compound provided herein is sufficiently basic or acidic to form stable nontoxic acid; or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases can include, but are not limited to, sodium, potassium, lithium, ammonium, calcium and magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, heterocycloalkyl and the like. Also included are amines where the two or three substituents, together with the amino nitrogen, form a heterocycloalkyl and heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine and the like. Other carboxylic acid; derivatives can be useful, for example, carboxylic acid; amides, including carboxamides, lower alkyl carboxamides or dialkyl carboxamides and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, an enantiomerically enriched mixture, a mixture of diastereomers or a mixture of diastereomers and enantiomers). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular steroisomer (e.g., enantiomer, diasteromer, etc.) of a compound used in the disclosed methods is depicted by name or structure, the stereochemical purity of the compounds is at least 60%, 70%, 80%, 90%, 95%, 97%, 99%, 99.5% or 99.9%. "Stererochemical purity" means the weight percent of the desired stereoisomer relative to the combined weight of all stereoisomers. Compounds designated "D" in Table 1 are those in which the relative stereochemistry, but not the absolute stereochemistry, has been determined. As such, the invention also includes both enantiomers of compounds disclosed in the exemplification.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds provided herein can be useful to activate the NRF2 pathway in a cell. In one embodiment, the method comprises contacting a cell with an effective amount of a compound provided herein, or a pharmaceutically acceptable salt thereof. In one embodiment, the cell is contacted in vitro or in vivo. In one embodiment, contacting the cell includes administering the compound to a subject.

One embodiment of the invention includes a method for activating Nrf2 in a subject in need thereof, the method comprising administering to the subject a therapeutically effective amount of a compound described herein, or a pharmaceutically acceptable salt thereof, thereby activating Nrf2 in the subject.

One embodiment of the invention includes a method for inhibiting a KEAP1 protein in a cell, the method comprising contacting a cell with an effective amount of a compound provided herein, or a pharmaceutically acceptable salt thereof, thereby inhibiting a KEAP1 protein in the cell.

One embodiment of the invention includes a method for increasing a cell's ability to resist a stress, the method comprising administering to the subject a therapeutically effective amount of a compound described herein, or a pharmaceutically acceptable salt thereof, thereby increasing the cell's ability to resist the stress. The stress is selected from the group consisting of heat shock, oxidative stress, osmotic stress, DNA damage, inadequate salt level, inadequate nitrogen level and inadequate nutrient level.

One embodiment of the invention includes a method for mimicking the effect of nutrient restriction on the cell, the method comprising administering to the subject a therapeutically effective amount of a compound described herein, or a pharmaceutically acceptable salt thereof, thereby mimicking the effect of the nutrient restriction on the cell.

One embodiment of the invention includes a method for promoting survival of a eukaryotic cell (e.g., a mammalian cell) or increasing the lifespan of the cell, the method comprising administering to the subject a therapeutically effective amount of a compound provided herein, or a pharmaceutically acceptable salt thereof, thereby promoting survival of the eukaryotic cell or increasing the lifespan of the cell.

One embodiment of the invention includes a method for treating a disease associated with cell death in a subject, the method comprising administering to the subject a therapeutically effective amount of a compound described herein, or a pharmaceutically acceptable salt thereof.

One embodiment of the invention includes a method for treating a disease caused by oxidative stress in a subject, the method comprising administering to the subject a therapeutically effective amount of a compound provided herein, or a pharmaceutically acceptable salt thereof.

One embodiment of the invention includes a method for treating a disorder in a subject, wherein the disorder is selected from the group consisting of a neurodegenerative disease, inflammation/an inflammatory disease, an autoimmune disease, an ischemic fibrotic disease, a cancer, premature aging, a cardiovascular disease, a liver disease, a hemoglobinopathy, thalassemia (e.g. beta-thalassemia) and a metabolic disorder, the method comprising administering to the subject a therapeutically effective amount of a compound provided herein, or a pharmaceutically acceptable salt thereof. Hemoglobinopathy includes sickle cell disease (SCD). In one embodiment, the disorder is sickle cell disease or thalassemia (e.g. beta-thalassemia). More specifically, the disorder is sickle cell disease.

The neurodegenerative disease can be selected from the group consisting of Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia and epilepsy (repression of microglia activation). More preferably, the neurodegenerative disease is Parkinson's disease or amyotrophic lateral sclerosis.

The inflammatory disease can be selected from the group consisting of chronic cholecystitis, aortic valve stenosis, restenosis, a skin disease, a pulmonary diseases and a disease of the airway, inflammatory uveitis, atherosclerosis, arthritis, conjunctivitis, pancreatitis, a chronic kidney disease (CDK), an inflammatory condition associated with diabetes, an ischemia, a transplant rejection, a CD14 mediated sepsis, a non-CD14 mediated sepsis, Behcet's syndrome, ankylosing spondylitis, sarcoidosis and gout. In some embodiments, the skin disease is selected from the group consisting of rash, contact dermatitis and atopic dermatitis. In one embodiment, the pulmonary disease and disease of the airway is selected from the group consisting of Adult Respiratory Disease Syndrome (ARDS), Chronic Obstructive Pulmonary Disease (COPD), pulmonary fibrosis, an interstitial lung disease, asthma, chronic cough, allergic rhinitis, bronchiectasis and bronchitis. In one embodiment, the inflammatory condition associated with diabetes is selected from a diabetic retinopathy, a diabetic cardiomyopathy and a diabetes-induced aortic damage.

The autoimmune disease is selected from the group consisting of psoriasis, inflammatory bowel disease, rheumatoid arthritis, systemic lupus erythematosus, multiple sclerosis, type 1 diabetes, systemic sclerosis and Sjogren's syndrome. In one embodiment, the inflammatory bowel disease is Crohn's disease or ulcerative colitis. In one embodiment, the autoimmune disease is type 1 diabetes. Alternatively, the autoimmune disease is multiple sclerosis.

The ischemic fibrotic disease is selected from the group consisting of stroke, acute lung injury, acute kidney injury, ischemic cardiac injury, acute liver injury and ischemic skeletal muscle injury.

The cancer is selected from the group consisting of prostate cancer, bladder cancer, ovarian cancer, breast cancer (e.g., breast cancer with mutated BRCA1), head and neck cancer, chronic lymphocytic leukemia, thymus cancer, hepatocellular carcinoma, colorectal cancer, colon cancer, skin cancer, pancreatic cancer, leukemia, lung cancer, glioblastoma, cervical cancer, lymphoma, Waldenstrim's macroglobulinemia and multiple myeloma.

The cardiovascular disease can be selected from the group consisting of pulmonary arterial hypertension, systemic hypertension, coronary artery disease, peripheral artery disease and atherosclerosis.

The liver disease can be selected from the group consisting of non-alcoholic steatohepititis (NASH), alcoholic liver disease, primary biliary cirrhosis and primary sclerosing cholangitis.

The hemoglobinopathy is a condition that involves a mutation in human beta-globin or an expression control sequence thereof, such as sickle cell disease (SCD) or beta-thalassemia. SCD typically arises from a mutation substituting thymine for adenine in the sixth codon of the beta-chain gene of hemoglobin (i.e., GAG to GTG of the HBB gene). This mutation causes glutamate to valine substitution in position 6 of the Hb beta chain. The resulting Hb, referred to as HbS, has the physical properties of forming polymers under conditions of low oxygen tension. SCD is typically an autosomal recessive disorder. Beta-Thalassemias are a group of inherited blood disorders caused by a variety of mutational mechanisms that result in a reduction or absence of synthesis of β-globin and leading to accumulation of aggregates of unpaired, insoluble α-chains that cause ineffective erythropoiesis, accelerated red cell destruction, and severe anemia. Subjects with beta-thalassemia exhibit variable phenotypes ranging from severe anemia to clinically asymptomatic individuals. The genetic mutations present in β thalassemias are diverse, and can be caused by a number of different mutations. The mutations can involve a single base substitution or deletions or inserts within, near or upstream of the β globin gene. For example, mutations occur in the promoter regions preceding the beta-globin genes or cause production of abnormal splice variants. $\beta^0$ is used to indicate a mutation or deletion which results in no functional β globin being produced. $\beta^+$ is used to indicate a mutation in which the quantity or β globin is reduced or in which the β globin produced has a reduced functionality.

Examples of thalassemias include thalassemia minor, thalassemia intermedia, and thalassemia major.

Thalassemia minor refers to thalassemia where only one of beta-globin alleles bears a mutation. Individuals typically suffer from microcytic anemia. Detection usually involves lower than normal MCV value (<80 fL) plus an increase in fraction of Hemoglobin A2 (>3.5%) and a decrease in fraction of Hemoglobin A (<97.5%). Genotypes can be $\beta^+/\beta$ or Thalassemia intermedia refers to a thalassemia intermediate between the major and minor forms. Affected individuals can often manage a normal life but may need occasional transfusions, e.g., at times of illness or pregnancy, depending on the severity of their anemia. Genotypes can be $\beta^+/\beta^+$ or $\beta^0/\beta$.

Thalassemia major refers to a thalassemia where both beta-globin alleles have thalassemia mutations. This is a severe microcytic, hypochromic anemia. If left untreated, it causes anemia, splenomegaly, and severe bone deformities and typically leads to death before age 20. Treatment consists of periodic blood transfusion; splenectomy if splenomegaly is present, and treatment of transfusion-caused iron overload. Cure is possible by bone marrow transplantation. Genotypes include $\beta^+/\beta^0$ or $\beta^0/\beta^0$ or $\beta^+/\beta^+$. Mediterranean anemia or Cooley's anemia has a genotype of $\beta^0/\beta^0$ so that no hemoglobin A is produced. It is the most severe form of β-thalassemia.

Although carriers of sickle cell trait do not suffer from SCD, individuals with one copy of HbS and one copy of a gene that codes for another abnormal variant of hemoglobin, such as HbC or Hb beta-thalassemia, typically will have a less severe form of sickle cell disease. For example, another specific defect in beta-globin causes another structural variant, hemoglobin C (HbC). Hemoglobin C (abbreviated as Hb C or HbC) is an abnormal hemoglobin in which substitution of a glutamic acid; residue with a lysine residue at the 6th position of the β-globin chain has occurred. A subject that is a double heterozygote for HbS and HbC (HbSC disease) is typically characterized by symptoms of moderate clinical severity.

Another common structural variant of beta-globin is hemoglobin E (HbE). HbE is an abnormal hemoglobin in which substitution of a glutamic acid; residue with a lysine residue at the 26th position of the β-globin chain has occurred. A subject that is a double heterozygote for HbS and HbE has HbS/HbE syndrome, which usually causes a phenotype similar to HbS/b+ thalassemia, discussed below.

A subject that is a double heterozygote for HbS and $\beta^0$ thalassemia (i.e., HbS/$\beta^0$ thalassemia) can suffer symptoms clinically indistinguishable from sickle cell anemia.

A subject that is a double heterozygote for HbS and $\beta^+$ thalassemia (i.e., HbS/$\beta^+$ thalassemia) can have mild-to-moderate severity of clinical symptoms with variability among different ethnicities.

Rare combinations of HbS with other abnormal hemoglobins include HbD Los Angeles, G-Philadelphia, HbO Arab, and others.

Nrf2 upregulates fetal hemoglobin which alleviates some of the symptoms of these disorders. Therefore, in some embodiments, the disclosed compositions are used to treated SCD or thalassemia (e.g. beta-thalassemia), including those that involve a mutation in human beta-globin or an expression control sequence thereof, as described above.

In some embodiments, the disclosed compositions and methods are used to treat a subject with an HbS/$\beta^0$ genotype, an HbS/$\beta^+$ genotype, an HBSC genotype, an HbS/HbE genotype, an HbD Los Angeles genotype, a G-Philadelphia genotype, or an abHbO Arab genotype.

In some embodiments, the compositions disclosed herein are administered to a subject in a therapeutically effective amount to treat one or more symptoms of sickle cell disease, a thalassemia (e.g. beta-thalassemia), or a related disorder. In subjects with sickle cell disease, or a related disorder, physiological changes in RBCs can result in a disease with the following signs: (1) hemolytic anemia; (2) vaso-occlusive crisis; and (3) multiple organ damage from microinfarcts, including heart, skeleton, spleen, and central nervous system. Thalassemia can include symptoms such as anemia, fatigue and weakness, pale skin or jaundice (yellowing of the skin), protruding abdomen with enlarged spleen and liver, dark urine, abnormal facial bones and poor growth, and poor appetite.

Retinopathy due to SCD can also be treated by administering a therapeutically effective amount of a compound according to any one of described herein. Sickle retinopathy occurs when the retinal blood vessels get occluded by sickle red blood cells and the retina becomes ischemic, angiogenic factors are made in retina. In sickle cell disease, this occurs mostly in the peripheral retina, which does not obscure vision at first. Eventually, the entire peripheral retina of the sickle cell patient becomes occluded and many neovascular formations occur. Administration of a compound according to any one of described herein can reduce or inhibit the formation of occlusions in the peripheral retina of a sickle cell patient.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; and delaying, inhibiting or decreasing the likelihood of the progression of the disease, disorder or syndrome.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, orally, topically, enterally (e.g. orally), parenterally, transdermally, transmucosally, via inhalation, intracisternally, epidurally, intravaginally, intravenously, intramuscularly, subcutaneously, intradermally and intravitreally to the mammal. Administering a compound described herein, or a pharmaceutically acceptable salt thereof, to a mammal also includes administering topically, enterally (e.g. orally), parenterally, transdermally, transmucosally, via inhalation, intracisternally, epidurally, intravaginally, intravenously, intramuscularly, subcutaneously, intradermally and intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups or wafers and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that a therapeutically effective dosage level will be obtained.

The tablets, troches, pills, capsules and the like can include the following: binders such as gum tragacanth, acacia, corn starch and gelatin; excipients such as dicalcium phosphate; a disintegrating agent such as corn starch, potato starch, alginic acid; and the like; a lubricant such as magnesium stearate; a sweetening agent such as sucrose, fructose, lactose and aspartame; and a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions and sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols, glycols and water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

"A therapeutically effective amount" and "an effective amount" are interchangeable and refer to an amount that, when administered to a subject, achieves a desired effect for treating a disease treatable with a compound or pharmaceutically acceptable salt thereof as described herein. The therapeutically effective amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 µg to about 100 mg/kg of body weight per day.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXAMPLE

Key in Table 1 below:
A: Absolute configuration determined by x-ray crystallography and/or circular dichroism
B: Absolute configuration assigned by comparison to a class A compound or derived from a common intermediate in the synthesis of a class A compound
C: Absolute configuration assigned based on literature precedent
D: Absolute configuration unknown

TABLE 1

| Compound | Stereochemical Determination |
| --- | --- |
| 1-I | C |
| 1-J | C |
| 2 | C |
| 3 | C |
| 4 | C |
| 5-B | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | C |
| 20 | C |
| 21 | C |

TABLE 1-continued
| Compound | Stereochemical Determination |
|---|---|
| 22-F | C |
| 22 | C |
| 23 | C |
| 24 | C |
| 25 | C |
| 26 | C |
| 27 | C |
| 28 | C |
| 29 | C |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | C |
| 42 | C |
| 43 | C |
| 44 | C |
| 45 | C |
| 46 | C |
| 47 | C |
| 48 | C |
| 49 | C |
| 50 | C |
| 51 | C |
| 52 | C |
| 53 | C |
| 54 | C |
| 55 | C |
| 56 | C |
| 57 | C |
| 58 | C |
| 59 | C |
| 60 | C |
| 102 | C |
| 103 | C |
| A | C |
| B | C |
| C | C |
| D | C |
Example 1. Synthesis of Compounds 1-I and 1-J
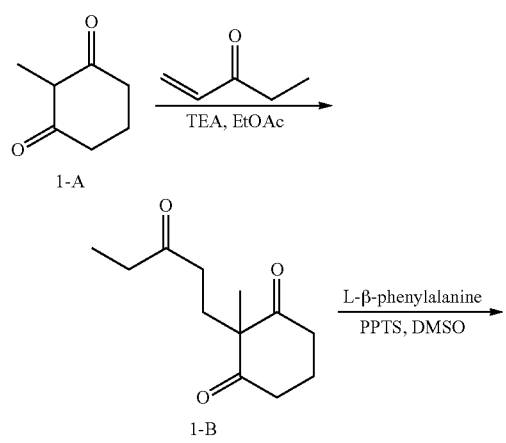
Preparation of Compound 1-B
To a mixture 2-methyl cyclohexanedione 1-A (CAS #1193-55-1) (4.5 g, 35.85 mmol, 1.0 eq.), TEA (6.5 mL, 46.60 mmol, 1.3 eq.) in ethyl acetate (100 mL) was added ethyl vinyl ketone (3.9 mL, 39.43 mmol, 1.1 eq.). The mixture was stirred at 70° C. for 10 h. TLC (PE/EA=2:1) showed the reaction was complete. The mixture was cooled to room temperature and concentrated to give a crude product, which was purified by column chromatography (PE/EA=10:1) to give compound 1-B (6.2 g, 82%) as yellow oil.

$^1$HNMR: (400 MHz, CDCl$_3$) δ: 2.85-2.74 (m, 2H), 2.73-2.63 (m, 2H), 2.44 (q, J=7.4 Hz, 2H), 2.41-2.34 (m, 2H), 2.17-2.06 (m, 3H), 2.01-1.89 (m, 1H), 1.29 (s, 3H), 1.07 (t, J=7.3 Hz, 3H).

Preparation of Compound 1-C

To a mixture of compound 1-B (5.0 g, 24 mmol, 1.0 eq.), L-β-phenylalanine (1.2 g, 7 mmol, 0.3 eq.) in DMSO (1.5 mL, 24 mmol, 1.0 eq.) was added PPTS (3 g, 12 mmol, 0.5 eq.). The mixture was stirred at 50° C. for 12 h. TLC (PE/EA=3:1) showed the reaction was complete. The mixture was diluted with EA (100 mL), washed with H$_2$O (50 mL), brine (50 mL), the organic layer was dried over Na$_2$SO$_4$, filtered and the filtrate was concentrated to give a crude product, which was purified by column chromatography (PE/EA=10:1) to give compound 1-C (3.2 g, 70%) as yellow oil.

Preparation of Compound 1-D

To a mixture of compound 1-C (3.2 g, 16.7 mmol, 1.0 eq.), D-CSA (0.19 g, 1.35 mmol, 0.07 eq.) in 2-ethyl-2-methyl-1,3-dioxolane (15.6 mL) and ethane-1,2-diol (10.4 mL). The mixture was stirred at 40° C. for 18 h. TLC (PE/EA=3:1) showed most compound 1-C was consumed. The mixture was poured into sat. NaHCO$_3$ (50 mL) and extracted with EA (50 mL×2), the combined organic layers were washed with H$_2$O (30 mL), brine (30 mL), dried over Na$_2$SO$_4$, filtered and concentrated to give a crude product, which was purified by column chromatography (PE/EA=30:1 to 15:1) to give compound 1-D (2.7 g, 68.7%) as yellow oil.

$^1$HNMR: (400 MHz, CDCl$_3$) δ: 4.07-3.86 (m, 4H), 2.81-2.61 (m, 1H), 2.54-2.33 (m, 2H), 2.31-2.10 (m, 2H), 1.96-1.82 (m, 2H), 1.76 (s, 3H), 1.75-1.53 (m, 3H), 1.33 (s, 3H).

Preparation of Compound 1-E

To a solution of compound 1-D (400 mg, 1.69 mmol, 1.0 eq.) in THF (6 mL) was added t-BuOK (1M in THF, 1.86 mL, 1.86 mmol, 1.1 eq.) dropwise at 0° C. under N$_2$, and the reaction mixture was stirred at 25° C. for 1 h. A solution of MeI (264 mg, 1.86 mmol, 1.1 eq.) was added to the above reaction mixture at 0° C. After addition, the reaction mixture was stirred at 25° C. for another 1 h. TLC (PE:EA=8:1) showed a new spot. Saturated NH$_4$Cl (2 mL) was added to quench the reaction. The two phases were separated, and the aqueous phase was extracted with EtOAc (10 mL×2). The combined organic phase was dried over Na$_2$SO$_4$, filtered, concentrated to give a crude product, which was purified by column chromatography (PE:EA=8:1) to give compound 1-E as colorless oil (350 mg, 82.3%).

$^1$HNMR: (400 MHz, CDCl$_3$) δ: 5.58 (t, J=3.2 Hz, 1H), 4.05-3.94 (m, 4H), 2.63-2.49 (m, 2H), 2.28-2.23 (m, 3H), 1.95-1.85 (m, 1H), 1.75-1.60 (m, 2H), 1.23 (s, 6H), 1.13 (s, 3H).

Preparation of Compound 1-F

To a solution of compound 1-E (0.4 g, 1.6 mmol, 1.0 eq.) in i-PrOH (3.2 mL) was added PhSiH$_3$ (173 mg, 1.6 mmol, 1.0 eq.) and TBHP (5.5 M in decane, 0.43 mL, 2.4 mmol, 1.5 eq.) at 25° C. The reaction mixture was charged with N$_2$ for 5 min. Then Mn(dpm)$_3$ (96.6 mg, 0.16 mmol, 0.1 eq.) was added, and the reaction mixture was charged with N$_2$ for 5 min, and the reaction mixture was stirred at 25° C. for 1 h. TLC (PE:EA=8:1) showed the starting material was consumed. The solvent was concentrated to give a crude product, which was purified by column chromatography (PE/EA=3:1) to give compound 1-F (0.35 g, 86.8%) as a colorless oil and it was used for the next step without further purification.

Preparation of Compound 1-G

To a solution of compound 1-F (0.85 g, 3.37 mmol, 1.0 eq.) in THF (15 mL) was added LDA (1.85 mL, 1.85 mmol, 1.1 eq.) at −78° C. under N$_2$. The reaction mixture was stirred at −70° C. for 1 h. Then TsCN (670 mg, 3.7 mmol, 1.1 eq.) in THF (20 mL) was added dropwise to the above reaction mixture at −70° C., and the reaction mixture was stirred at this temperature for 1 h. TLC (PE:EA=8:1) showed the starting material was consumed. Saturated NH$_4$Cl (5 mL) was added to quench the reaction. EtOAc (10 mL) was added, followed by water (10 mL). The two phases were separated, and the aqueous phase was extracted with EtOAc (10 mL×2). The combined organic phase was dried over Na$_2$SO$_4$, filtered, concentrated to give a crude product, which was purified by column chromatography (PE/EA=3:1) to give compound 1-G as yellow oil, which was used for the next step without any purification.

Preparation of Compound 1-H

A reaction mixture of compound 1-G (390 mg, 1.4 mmol, 1.0 eq.) and DDQ (582 mg, 2.1 mmol, 1.5 eq.) in PhMe (15 mL) was stirred under reflux for 2 h. LCMS showed the desired product. The reaction was cooled to 25° C., and the solid was filtered off. The filtrate was concentrated to give a crude product, which was purified by column chromatography (PE/EA=3:1) to give compound 1-H (300 mg, 77%) as yellow oil.

Preparation of Compounds 1-I and 1-J

This reaction was taken in two batches in parallel:

To a solution of compound 1-H (150 mg, 0.55 mmol, 1.0 eq.) in THF:H$_2$O (1:1, 1 mL) was added HCl (6M in H$_2$O, 1 mL) at 25° C., and the reaction mixture was stirred at 25° C. for 12 h. TLC (PE:EA=3:1) showed a little starting material remained with new spot detected. Saturated NaHCO$_3$ was added to neutralize the reaction. EtOAc (10 mL) was added, and the two phases were separated, the aqueous phase was extracted with EtOAc (10 mL×3). The combined organic phase was dried over Na$_2$SO$_4$, filtered, concentrated to give a crude product, which was purified by prep. HPLC (Mobile phase A: water with 0.225% FA, Mobile phase B: acetonitrile; Column: Phenomenex Synergi Max-RP 250×80 mm×10 um; Detection wavelength: 220 nm) to give a pair of isomer (68.5 mg, purity about 80%). These two isomers were further purified together with an additional 20 mg of impure material by prep. HPLC (Mobile phase A: water with 0.225% FA, Mobile phase B: acetonitrile; Column: Phenomenex Synergi Max-RP 250×80 mm×10 um; Detection wavelength: 220 nm) to give compound 1-I (28.2 mg, 31.8% separated yield) as white solid and compound 1-J (27.1 mg, 30.6% separated yield). The relative stereochemistry of each product was determined by 2D-NMR.

Spectra for 1-I

HPLC: (Purity: 100%)

MS: (M+1: 232.1)

$^1$HNMR: (400 MHz, CDCl$_3$) δ: 8.26 (s, 1H), 2.66 (m, 1H), 2.44-2.40 (m, 1H), 2.25-2.15 (m, 1H), 1.99-1.89 (m, 3H), 1.75-1.65 (m, 1H), 1.47 (s, 3H), 1.26 (s, 3H), 1.22 (s, 3H).

Spectra for 1-J

HPLC: (Purity: 100%)

MS: (M+1: 232.1)

¹HNMR: (400 MHz, CD₃CN) δ: 7.74 (s, 1H), 2.89-2.83 (m, 1H), 2.32-2.19 (m, 3H), 2.07-2.04 (m, 2H), 1.95-1.85 (m, 1H), 1.55 (s, 3H), 1.21 (s, 3H), 1.05 (s, 3H).

The four compounds listed below, namely compounds A-D, can be prepared using a method similar to that used for preparing compound 1-I except for the use of a starting material, which is slightly different from 1A.

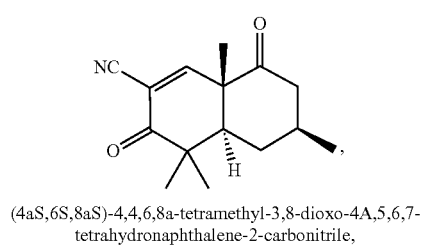

A (4aS,6S,8aS)-4,4,6,8a-tetramethyl-3,8-dioxo-4A,5,6,7-tetrahydronaphthalene-2-carbonitrile,

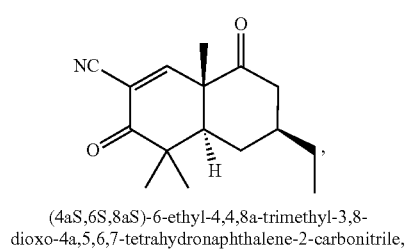

B (4aS,6S,8aS)-6-ethyl-4,4,8a-trimethyl-3,8-dioxo-4a,5,6,7-tetrahydronaphthalene-2-carbonitrile,

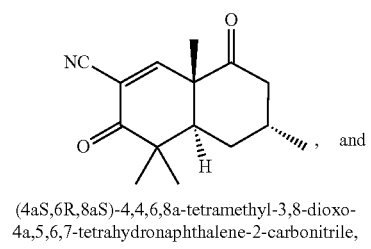

C (4aS,6R,8aS)-4,4,6,8a-tetramethyl-3,8-dioxo-4a,5,6,7-tetrahydronaphthalene-2-carbonitrile, and

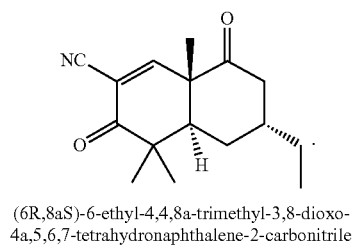

D (6R,8aS)-6-ethyl-4,4,8a-trimethyl-3,8-dioxo-4a,5,6,7-tetrahydronaphthalene-2-carbonitrile.

Example 2. Synthesis of Compound 2

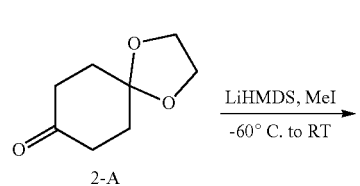

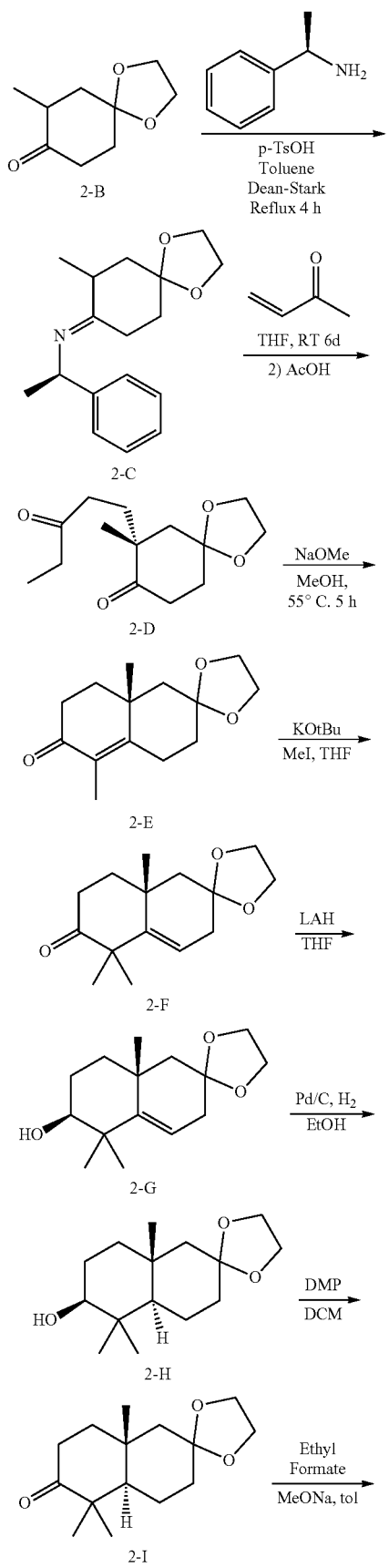

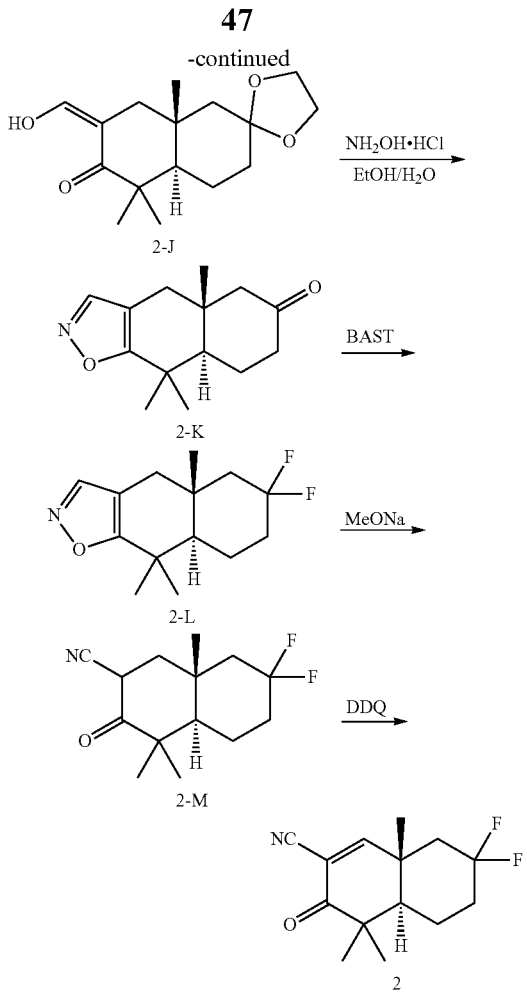

The method for preparing intermediates of compound 2, including compounds 2-C to 2-E, is described in Tenius, et al., Synthetic Communications, 30(8), 1371-1378 (2000).

Preparation of Compound 2-B

The reaction was set in two batches in parallel and work-up was combined.

To a stirred solution of 1 M of Lithium hexamethyldisilazide in THF (1.056 L, 1.056 mol, 1.03 eq) at −60° C. was added compound 2-A (160 g, 1.026 mol, 1 eq) in DMF (600 mL) slowly using an addition funnel and keeping the temperature below −60° C. The reaction mixture was allowed to stir below −60° C. for 1.5 h, and then treated with Methyl iodide (142 g, 1.00 mol, 0.99 eq) dropwise. Warmed to room temperature and stirred for 20 h. TLC (PE/EA=3:1) showed a little compound 2-A remained. The reaction mixture was quenched by half-saturated ammonium chloride solution (1.5 L) below 20° C. Extracted with MTBE (1 L×6). The combined organic phase was concentrated under reduced pressure to about 2 L, washed with brine (500 mL×3). The brine layer was extracted with MTBE (500 mL×3). The combined organic layer was dried over anhydrous $Na_2SO_4$, filtered and concentrated. The residue was azeotroped with heptane 4 times (300 mL×4). The resultant oil was slurried with heptanes (~800 mL) until it dissolved at room temperature, and then cooled to −10° C. with vigorous stirring. The reaction oiled out but eventually crystallized. The pale-yellow solid was filtered and rinsed with heptanes (300 mL×3) to supply compound 2-B (260 g, 74.5% yield) as pale-yellow solid.

$^1$H-NMR: (400 MHz, $CDCl_3$) δ: 4.14-3.92 (m, 4H), 2.81-2.58 (m, 2H), 2.44-2.31 (m, 1H), 2.16-1.89 (m, 3H), 1.78-1.67 (m, 1H), 1.03 (d, J=6.7 Hz, 3H)

Preparation of Compound 2-C

To 2 L of round bottom flask containing compound 2-B (50 g, 0.294 mol, 1.0 eq), (R)-1-phenylethan-1-amine (35.2 g, 0.291 mol, 1.0 eq) and TsOH (0.505 g, 2.94 mmol, 0.01 eq) in 600 mL of anhydrous toluene was fitted with a Dean-Stark and heated to reflux for 20 h. The reaction was cooled to room temperature, concentrated to about 300 mL, the formed solid was filtered off, the filtrate was concentrated under reduced pressure to supply crude compound 2-C which was used for next step directly.

Preparation of Compound 2-D

To the solution of compound 2-C (80.29 g, 0.294 mol, 1.0 eq) in 100 mL of anhydrous THF was added ethyl vinyl ketone (39.04 g, 0.441 mol, 1.5 eq). After addition the mixture was stirred at room temperature for 6 days under nitrogen. After that 120 mL of a solution of 20% aqueous acetic acid was added below 20° C. and the mixture was stirred at 25° C. for 3 h. The solvents were removed under reduced pressure. 1 N HCl (40 mL) was added to the residue oil. The mixture was diluted with water (100 mL), extracted with MTBE (200 mL×4), the combined organic layers was washed with brine (200 mL×2), dried over anhydrous $Na_2SO_4$. Filtered, the filtrate was concentrated under reduced pressure and the residue was purified by column chromatography on silica gel (PE/EA=30:1-20:1-10:1) to supply compound 2-D (44 g, 59% yield) as yellow oil $^1$H-NMR: (400 MHz, $CDCl_3$) δ: 3.98 (d, J=2.0 Hz, 4H), 2.65-2.46 (m, 2H), 2.45-2.32 (m, 3H), 2.28-2.17 (m, 1H), 2.14-2.06 (m, 1H), 2.01-1.90 (m, 3H), 1.85-1.69 (m, 2H), 1.10 (s, 3H), 1.03 (t, J=7.3 Hz, 3H).

Preparation of Compound 2-E

To a 2 L three-neck round bottom flask containing 600 mL of methanol in an ice/water bath was added Sodium (11.95 g, 0.52 mol, 3.0 eq) piecewise. Compound 2-D (44 g, 0.173 mol, 1.0 eq) was added as a solution in 600 mL of methanol. The reaction mixture was heated to 55° C. for 5 h. TLC (PE/EA=3:1) showed compound 2-D was consumed completely. The solvent was removed in vacuo. The residue was slurried in 1.0 L of MTBE and 160 mL of water. 1N HCl was added to pH of ~4 in ice-bath. The aqueous layer was separated and extracted with MTBE (300 mL×2). The organic phase was washed with brine (300 mL×3) and dried over anhydrous $Na_2SO_4$. Filtered and concentrated, the residue was purified by column chromatography on silica gel (PE/EA=50:1-30:1-15:1) to supply compound 2-E (33 g, 80% yield) as pale-yellow oil.

$^1$H-NMR: (400 MHz, $CDCl_3$) δ: 4.07-3.98 (m, 2H), 3.97-3.89 (m, 2H), 2.75 (td, J=3.7, 15.0 Hz, 1H), 2.61-2.34 (m, 3H), 1.97-1.89 (m, 1H), 1.88-1.70 (m, 6H), 1.68-1.62 (m, 2H), 1.35 (s, 3H).

Preparation of Compound 2-F

Potassium tert-butoxide (18.16 g, 162 mmol, 1.5 eq) was added to the solution of compound 2-E (25.5 g, 108 mmol, 1 eq) in 900 mL of THF by portionwise at 0-5° C., then the mixture was stirred at 25° C. for 1.5 h. Methyl iodide (34.88 g, 246 mmol, 2.3 eq) was added to the mixture at 0° C. by dropwise, and then stirred at 20-25° C. for 18 h. TLC (PE:EA=4:1) showed compound 2-E was remained and the desired product was observed. 50 mL of saturated $NH_4Cl$ was added to the mixture and the mixture was extracted with EtOAc (200 mL×3). The organic layers were combined and washed with 100 mL of brine, dried over anhydrous $Na_2SO_4$, filtered and concentrated. The residue was purified by column chromatography on silica gel (PE/acetone=200:1) to give compound 2-F (12 g, 52% yield) as yellow oil.

Preparation of Compound 2-G

To the suspension of LAH (7.459 g, 38.2 mmol, 1.2 eq) in 150 mL of anhydrous THF was added compound 2-F (8.0 g, 32 mmol, 1.0 eq) in 20 mL of anhydrous THF by dropwise. After addition the mixture was stirred at 25° C. for 1.5 h. TLC (PE:EA=3:1) showed compound 2-F was consumed completely. 1.45 mL of water was added slowly (caution: gas evolution), then 1.45 mL of 15% aqueous NaOH and 4.5 mL of water were added in turn. The mixture was diluted with EA (300 mL) and stirred with anhydrous $Na_2SO_4$ (20 g) for 30 min, filtered through a pad of celite. The filter cake was washed with EA (500 mL×2). The combined filtrate was concentrated under reduced pressure to supply crude compound 2-G (8.0 g) as pale-yellow oil.

$^1$H-NMR: (400 MHz, $CDCl_3$) δ: 5.52 (t, J=3.7 Hz, 1H), 4.05-3.85 (m, 4H), 3.27 (d, J=8.2 Hz, 1H), 2.47-2.36 (m, 1H), 2.34-2.24 (m, 1H), 1.89-1.76 (m, 1H), 1.74-1.62 (m, 3H), 1.60-1.51 (m, 2H), 1.47 (br. s., 1H), 1.29 (s, 3H), 1.17 (s, 3H), 1.07 (s, 3H).

Preparation of Compound 2-H

To a solution of compound 2-G (8 g, 31.7 mmol, 1.0 eq) in 80 mL of EtOH was added $Pd(OH)_2/C$ (2.0 g) under $N_2$ atmosphere. The suspension was degassed under vacuum and purged with $H_2$ for several times. The mixture was stirred under $H_2$ (15 psi) at 20° C. for 24 hours. TLC (PE/EA=3:1, $KMnO_4$) showed compound 2-G was consumed completely. The suspension was filtered through a pad of Celite and the pad was washed with EtOAc (300 mL×2). The combined filtrate was concentrated under reduced pressure to give crude compound 2-H (10 g) as colorless oil. The crude compound 2-H was slurried with MTBE/heptanes (6 mL/10 mL) and cooled to −10° C. The crystalline material formed was collected and dried under vacuum to supply compound 2-H (4.0 g pure) as white solid.

$^1$H-NMR: (400 MHz, $CDCl_3$) δ: 3.97-3.94 (m, 2H), 3.90-3.86 (m, 2H), 3.28-3.22 (m, 1H), 1.88-1.67 (m, 1H), 1.64-1.53 (m, 2H), 1.52-1.49 (m, 4H), 1.32-1.28 (m, 2H), 1.21-1.09 (m, 1H), 1.04 (s, 3H), 1.01 (s, 3H), 0.9-0.8 (m, 1H), 0.79 (s, 3H).

Preparation of Compound 2-I

To a solution of compound 2-H (2.0 g, 7.87 mmol, 1.0 eq) in 50 mL of DCM was added Dess-Marin Periodinane (DMP) (4.0 g, 9.45 mmol, 1.2 eq) in ice-bath. The mixture was stirred at 0-5° C. under $N_2$ atmosphere for 1.5 h. TLC (PE/EA=3:1) showed compound 2-H was consumed completely. The mixture was diluted with DCM (50 mL), adjusted pH to 8 by adding saturated aqueous $NaHCO_3$. The mixture was filtered through a pad of celite, concentrated. The residue was stirred in EtOAc (100 mL) and filtered, concentrated, purified by column chromatography on silica gel (PE/EA=50:1-40:1-30:1) to supply compound 2-I (1.4 g, 72.4% yield) as a colorless solid.

$^1$H-NMR: (400 MHz, $CDCl_3$) δ: 4.06-3.81 (m, 4H), 2.69-2.68 (m, 1H), 2.38-2.36 (m, 1H), 1.94-1.84 (m, 1H), 1.74-1.46 (m, 6H), 1.43-1.34 (m, 2H), 1.21 (s, 3H), 1.11 (s, 3H), 1.04 (s, 3H).

Preparation of Compound 2-J

To a solution of compound 2-H (4.5 g, 17.85 mmol, 1.0 eq) in 28 mL of Ethyl formate (26.39 g, 357 mmol, 20.0 eq) was added NaOMe (11.23 mL, 60.69 mmol, 3.4 eq, 5.4 M in MeOH) at 0-5° C. The mixture was stirred at 23° C. under $N_2$ atmosphere for 30 min, slurried with toluene (30 mL) for 4 h. TLC (PE/EA=6:1) showed compound 12-H was consumed completely. The reaction was quenched by addition of water (150 mL), adjusted pH to 5 by adding AcOH, extracted with EtOAc (50 mL×3). The combined organic layer was washed with brine (30 mL×2), dried over anhydrous $Na_2SO_4$, filtered, concentrated under reduced pressure to supply crude compound 2-J (5.0 g) as pale-yellow solid.

Preparation of Compound 2-K

To a solution of compound 2-J (5.0 g, 17.8 mmol, 1.0 eq) in 200 mL of $EtOH/H_2O$ (V:V=10:1) was added hydrochloride hydroxylamine (1.23 g, 17.8 mmol, 1.0 eq) in 20 mL of $EtOH/H_2O$ (V:V=10:1) by dropwise. After addition the mixture was stirred at 50° C. for 18 h. TLC (PE/EA=2:1) showed compound 2-J was consumed completely. The mixture was concentrated under reduced pressure to about 10 mL, diluted with water (100 mL), adjusted pH to 7 by adding saturated aqueous $NaHCO_3$. Extracted with EtOAc (50 mL×3). The combined organic layer was washed with brine (30 mL×2), dried over anhydrous $Na_2SO_4$, filtered, and concentrated under reduced pressure, the residue was slurried with MTBE (10 mL), filtered. The filter cake was collected to supply compound 2-K (2.1 g, 51% yield) as white solid and a second crop of 1.0 g of impure compound 2-K as yellow solid.

$^1$HNMR: (400 MHz, $CDCl_3$) δ: 8.03 (s, 1H), 2.53-2.20 (m, 6H), 2.16-2.06 (m, 1H), 2.05-1.97 (m, 1H), 1.93-1.77 (m, 1H), 1.42 (s, 3H), 1.24 (s, 3H), 0.92 (s, 3H).

Preparation of Compound 2-L

To a solution of compound 2-K (100 mg, 0.52 mmol, 1 eq) in DCM (5 mL) was added bis-(2-Methoxyethyl)aminosulfur trifluoride (BAST) (230 mg, 1.04 mmol, 2 eq). The mixture was stirred at 25° C. for 16 hours. The mixture was quenched with water (5 mL) and extracted with EA (10 mL×3). The combined organic phase was dried over sodium sulfate, and filtered. The filtrate was concentrated in vacuo to give the residue, which was purified by prep-HPLC (YMC-Actus Pro C18 150×30 5 um, water (0.1% TFA)-ACN) to give compound 2-L (30 mg, 22.7%) as an off-white solid.

$^1$HNMR: (400 MHz, $CDCl_3$) δ: 8.01 (s, 1H), 2.36-2.22 (m, 3H), 2.08-2.02 (m, 1H), 1.77-1.65 (m, 4H), 1.57-1.54 (m, 1H), 1.33 (s, 3H), 1.20 (s, 3H), 0.99 (s, 3H).

LCMS: (M+H: 256.0)

Preparation of Compound 2-M

To a solution of compound 2-L (25 mg, 0.1 mmol, 1 eq) in MeOH (5 mL) was added NaOMe (15 mg, 0.3 mmol, 3 eq). The mixture was stirred at 25° C. for 16 hours. The mixture was concentrated in vacuo to give the residue. The residue was taken up in water (15 mL) and extracted with EA (15 mL×3). The combined organic phase was dried over sodium sulfate and filtered. The filtrate was concentrated in vacuo to give compound 2-M (15 mg, crude), which was used directly in next step without purification.

Preparation of Compound 2

To a solution of compound 2-M (80 mg, 0.31 mmol, 1 eq) in toluene (5 mL) was added DDQ (213 mg, 0.93 mmol, 3 eq). The mixture was stirred at 110° C. for 3 hours. The mixture was concentrated in vacuo to give the residue. The residue was purified by column chromatography on silica gel (PE:EA=5:1) and further purified by prep-TLC (PE:EA=5:1) to give compound 2 (14.3 mg, 17.9%) as a yellow solid.

¹HNMR: (400 MHz, CDCl₃) δ 7.43 (s, 1H), 2.33-2.28 (m, 1H), 2.12-2.06 (m, 1H), 1.89-1.76 (m, 5H), 1.30 (s, 3H), 1.24 (s, 3H), 1.12 (s, 3H).
HPLC: (Purity: 100%).
SFC: (Purity: 98.8%)
LCMS: (M+H: 254.1)

Example 3. Synthesis of Compound 3

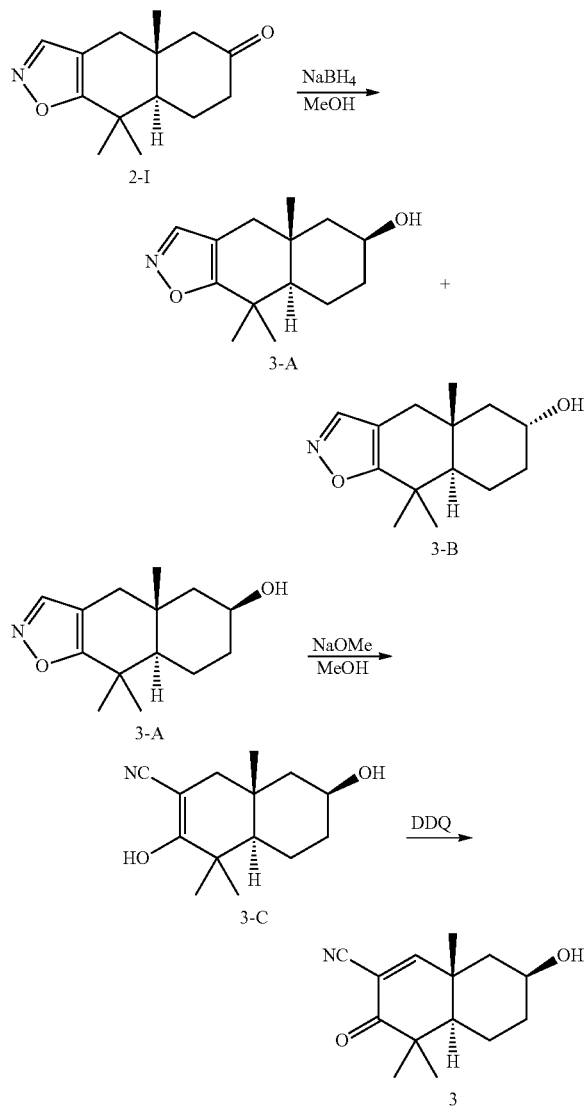

Preparation of Compounds 3-A and 3-B
To a solution of compound 2-I (1.5 g, 6.44 mmol, 1.0 eq) in 30 mL of methanol was added NaBH₄ (122 mg, 3.22 mmol, 0.5 eq) using ice-bath cooling. The mixture was stirred below 5° C. for 1 h. TLC (PE/EA=3:1) showed compound 2-I was consumed completely. The mixture was quenched by ice-water (100 mL), extracted with EtOAc (100 mL×3). The combined organic layer was washed with brine (50 mL×2), dried over anhydrous Na₂SO₄, filtered, and concentrated under reduced pressure. The residue was treated with MTBE (10 mL). The solid was collected by filtration and dried in vacuo to supply compound 3-A (1.05 g, 69.4% yield) as a white solid and 450 mg of a mixture of compounds 3-A and 3-B as pale-yellow solid.

¹HNMR: 3-A (400 MHz, CDCl₃) δ: 8.01 (s, 1H), 4.19 (br. s., 1H), 2.30-2.21 (m, 1H), 2.19-2.10 (m, 1H), 2.02-1.93 (m, 1H), 1.88-1.78 (m, 2H), 1.64-1.43 (m, 5H), 1.33 (s, 3H), 1.24 (s, 3H), 1.12 (s, 3H).

Preparation of Compound 3-C
To a suspension of compound 3-A (400 mg, 1.7 mmol, 1.0 eq) in 15 mL of anhydrous methanol was added NaOMe (275 mg, 5.1 mmol, 3.0 eq, 2.55 mL, 2 M in methanol). The mixture was stirred at 25° C. for 2 days. The suspension turned into a solution. TLC (PE/EA=2:1) showed compound 3-A was consumed completely. The mixture was concentrated under reduced pressure, the residue was diluted with water (50 mL), extracted with EtOAc (40 mL×3). The combined organic layer was washed with brine (30 mL×2), dried over anhydrous Na₂SO₄, filtered, concentrated under reduced pressure to supply crude compound 3-C (400 mg) as white solid.

Preparation of Compound 3
Compound 3-C (200 mg crude, 0.85 mmol, 1.0 eq) and DDQ (213 mg, 0.936 mmol, 1.1 eq) were added into 10 mL of anhydrous toluene. The mixture was stirred at 110° C. for 2 h.
TLC (PE/EA=2:1) showed only one spot was observed. The mixture was diluted with water (60 mL), extracted with EtOAc (50 mL×3). The combined organic layer was washed with brine (30 mL×2), dried over anhydrous Na₂SO₄, filtered, concentrated under reduced pressure. The residue was purified by column chromatography on silica gel (PE:acetone=10:1-8:1) and then re-purified by prep-TLC (PE: EA=2:1) to supply compound 3 (120 mg, 60% yield) as white solid.
HPLC: (Purity: 98.11%)
SFC: (EE: 100%)
MS: (M+H: 234.14)
¹HNMR: (400 MHz, CDCl₃) δ: 7.47 (s, 1H), 4.27 (br. s., 1H), 1.98 (d, J=14.3 Hz, 1H), 1.91-1.79 (m, 2H), 1.76-1.69 (m, 1H), 1.66-1.53 (m, 3H), 1.46 (s, 3H), 1.38 (br. s., 1H), 1.23 (s, 3H), 1.14 (s, 3H).

Example 4. Synthesis of Compounds 3 and 4

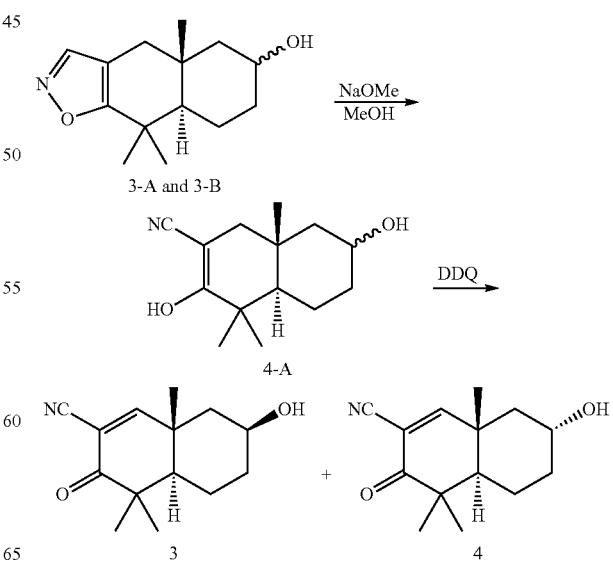

To a suspension of a mixture of compounds 3-A and 3-B obtained above (450 mg, 1.91 mmol, 1.0 eq) in 15 mL of anhydrous methanol was added NaOMe (2.85 mL, 5.7 mmol, 3.0 eq, 2M in methanol). The mixture was stirred at 30° C. for 20 h. TLC (PE/EA=2:1) showed starting material was consumed completely. The mixture was concentrated under reduced pressure to remove methanol, the residue was diluted with water (50 mL), extracted with EtOAc (20 mL×3). The combined organic layer was washed with brine (15 mL×2), dried over anhydrous $Na_2SO_4$, filtered, concentrated under reduced pressure to supply crude mixture 4-A (400 mg) as white solid.

To the mixture 4-A (400 mg, 1.7 mmol, 1.0 eq) in 20 mL of anhydrous toluene was added DDQ (348 mg, 1.53 mmol, 0.9 eq). The mixture was stirred at 110° C. for 2 h. It turned into red suspension. The mixture was diluted with EtOAc (50 mL), washed with brine (20 mL×3), dried over anhydrous $Na_2SO_4$, filtered, concentrated under reduced pressure. The residue was purified by column chromatography on silica gel (PE/EtOAc=10:1-6:1) and re-purified by prep-TLC (PE/EA=2:1) to supply compound 3 (63 mg, 16% yield) as white solid and compound 4 (33 mg, 8.3% yield) as purple solid.

Data for Compound 4
HPLC: (Purity: 100%)
SFC: (de: 99.44%)
MS: (M+H: 234.14)
$^1$HNMR: 19230-42-1D (400 MHz, $CDCl_3$) δ: 7.47 (s, 1H), 4.03-3.89 (m, 1H), 2.21 (d, J=11.2 Hz, 1H), 1.93 (dd, J=2.6, 11.9 Hz, 1H), 1.83-1.70 (m, 2H), 1.55-1.44 (m, 2H), 1.39 (t, J=11.7 Hz, 1H), 1.26 (s, 3H), 1.24 (s, 3H), 1.08 (s, 3H).

Example 5. Synthesis of Compound 5

Preparation of Compound 5-A
To a solution of freshly prepared 1M LDA (0.74 mL, 0.74 mmol) at −78° C. was added compound 2-I (0.135 g, 0.735 mmol) in a solution of 2 mL of THF. After 30 min, p-toluenesulfonyl cyanide (0.135 g, 0.743 mmol) in 1 mL of THF was added. The reaction was stirred at −78° C. for 30 min. The reaction was quenched by addition of 0.75 mL 1N HCL and the mixture was warmed to 0° C. The reaction was diluted with diethyl ether and the pH of the aqueous phase was adjusted using 1N HCl (~50 uL) to a pH of 3. The layers were separated and the organic phase was washed with brine, dried over $MgSO_4$, filtered, and concentrated. Purification using a 4 g silica gel column eluted with 10% acetone in heptanes afforded compound 5-A (110 mg; Yield=80%).

Data for 5-A:
$^1$H NMR (400 MHz, DMSO-d6) δ: 0.92-0.99 (m, 6H) 1.10 (s, 3H) 1.19-1.65 (m, 9H) 1.68-1.84 (m, 2H) 2.00-2.12 (m, 1H) 3.62-4.07 (m, 5H) 9.78 (s, 1H)
LC/MS (M+H)=278.

Preparation of Compound 5-B
To a solution of Compound 5-A (100.0 mg, 0.3605 mmol) in 10 mL benzene was added Dichlorodicyanoquinone (0.098 g, 0.43 mmol). The reaction was heated to reflux. After 30 min, the reaction was cooled to rt and filtered through Celite™ and rinsed with 5 mL benzene. The filtrate was concentrated and deposited on 400 mg silica gel. Purification by silica gel chromatography using a 4 g silica gel cartridge eluted using 20% ethyl acetate in heptanes afforded 80 mg of a white crystalline solid, compound 5-B.

Data for 5-B:
$^1$H NMR (400 MHz, DMSO-d6) δ: 1.00 (s, 3H) 1.14 (s, 3H) 1.24 (s, 3H) 1.38-1.68 (m, 4H) 1.71-1.92 (m, 3H) 3.73-3.98 (m, 4H) 7.93 (s, 1H).
LCMS (M+H)=273 HPLC: 98.9%.

Preparation of Compound 5
To a solution compound 5-B (37 mg, 0.13 mmol) in 3 mL of anhydrous acetone was added p-Toluenesulfonic acid monohydrate (0.0026 g, 0.013 mmol) and stirred for 2 d. The reaction was concentrated and deposited on 400 mg of silica gel and chromatographed with 20-30% ethyl acetate in heptanes on a 4 g silica gel column to afford a white solid, compound 5 (21 mg; Yield=68%).

Data for 5:
$^1$H NMR (400 MHz, DMSO-d6) δ: 1.02 (s, 3H) 1.09 (s, 3H) 1.16-1.25 (m, 3H) 1.73-1.89 (m, 1H) 1.90-2.02 (m, 1H) 2.22 (dd, J=13.80, 2.01 Hz, 1H) 2.28-2.47 (m, 3H) 2.57 (d, J=13.80 Hz, 1H) 7.87 (s, 1H).
LCMS: M+H=232
HPLC: 97.9%

Example 6. Synthesis of Compound 6

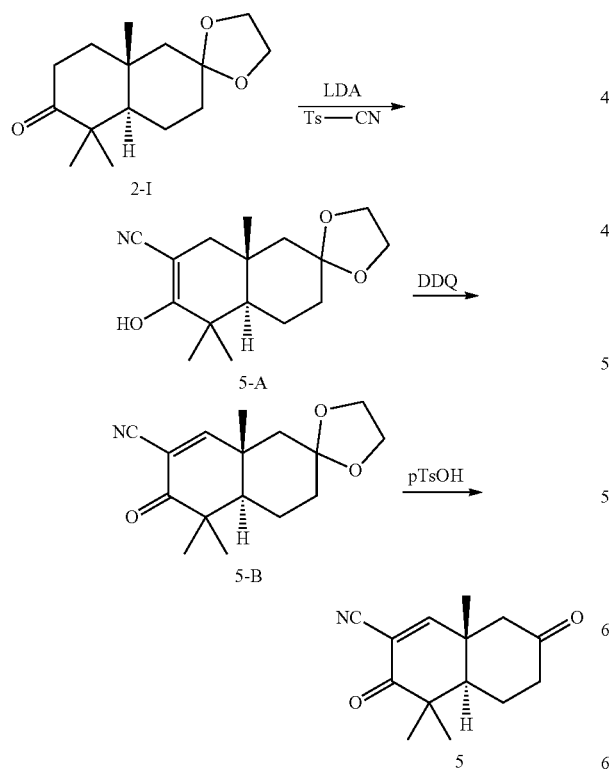

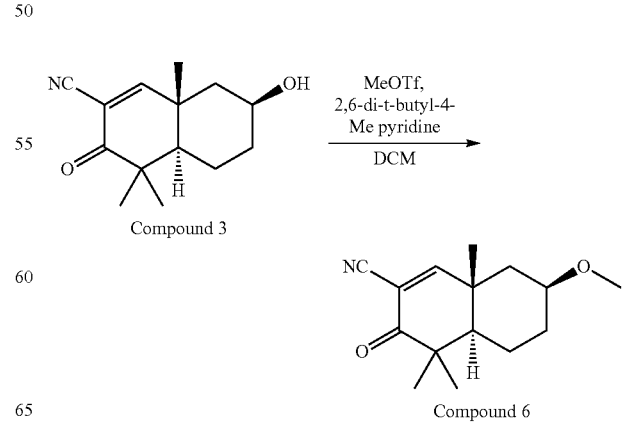

To a solution of compound 3 (95 mg, 0.41 mmol, 1.0 eq) in 15 mL of DCM was added 2,6-di-tert-butyl-4-methylpyridine (841 mg, 4.1 mmol, 10.0 eq) and MeOTf (535 mg, 3.28 mmol, 8.0 eq). The mixture was stirred at 30° C. for 36 h. TLC (PE/EA=2:1) showed compound 3 was consumed completely. The mixture was diluted with DCM (20 mL), washed with water (10 mL×2), dried over anhydrous Na$_2$SO$_4$, filtered, and concentrated under reduced pressure. The residue was purified by column chromatography on silica gel (PE/EtOAc=20:1-10:1) and then re-purified by prep-TLC (PE/EA=3:1) to supply compound 6 (60.4 mg, 59.8% yield) as white solid. Data for 6:

HPLC: (Purity: 99.01%)
LCMS: (M+H: 248.0)
$^1$HNMR: (400 MHz, CDCl$_3$) δ: 7.46 (s, 1H), 3.59 (br. s., 1H), 3.33 (s, 3H), 2.14 (d, J=13.9 Hz, 1H), 1.98 (d, J=13.9 Hz, 1H), 1.73 (br. s., 2H), 1.57-1.50 (m, 1H), 1.44 (d, J=13.5 Hz, 2H), 1.38 (s, 3H), 1.22 (s, 3H), 1.12 (s, 3H).

Example 7. Synthesis of Compound 7

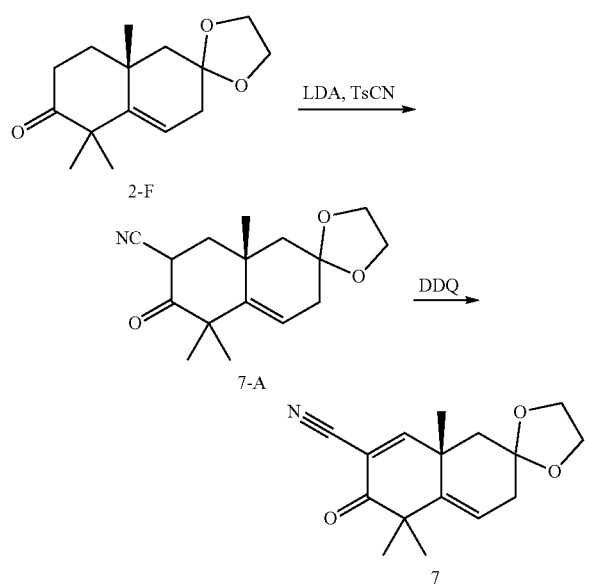

Preparation of Compound 7-A

To a solution of compound 2-F (150 mg, 0.6 mmol, 1.0 eq.) in THF (5 mL) was added LDA (0.45 mL, 0.9 mmol, 1.5 eq.) dropwise at −78° C. under N$_2$, and the reaction mixture was stirred a −70° C. for 1 h. Then TsCN (163 mg, 0.9 mmol, 1.5 eq.) in THF (3.0 mL) was added dropwise to the above reaction mixture at −78° C., and the reaction mixture was stirred at −70° C. for 1.5 h. TLC (PE:EA=3:1) showed the starting material was consumed. Saturated NH$_4$Cl (5 mL) was added to quench the reaction, followed by EtOAc (10 mL). The two phases were separated, and the aqueous phase was extracted with EtOAc (10 mL×3). The combined organic phase was dried over Na$_2$SO$_4$, filtered, concentrated to give a crude product, which was purified by column chromatography (PE:EA=10:1 to 2:1) to give crude product of compound 7-A as yellow oil (110 mg, 66.7%), which was used for next step without any further purification.

Preparation of Compound 7

A mixture of compound 7-A (110 mg, 0.4 mmol, 1.0 eq.) and DDQ (136 mg, 0.6 mmol, 1.5 eq.) in toluene (15 mL) was refluxed for 3 h. TLC (PE:EA=3:1) showed the starting material was consumed. The reaction mixture was concentrated to give a crude product, which was purified by prep-TLC (PE:EA=3:1) to give compound 7 (20.1 mg, 18.4%) as yellow solid.

$^1$H-NMR: (400 MHz, CDCl$_3$) δ: 7.54 (s, 1H), 5.72 (t, J=4.0 Hz, 1H), 4.04-3.98 (m, 2H), 3.90-3.87 (m, 2H), 2.41 (d, J=4.0 Hz, 2H), 1.93-1.90 (m, 1H), 1.70-1.66 (m, 1H), 1.53 (s, 3H), 1.34 (s, 3H), 1.32 (s, 3H).

HPLC: (purity: 97.39%).
LCMS: (M+H: 274.3).

Example 8. Synthesis of Compound 8

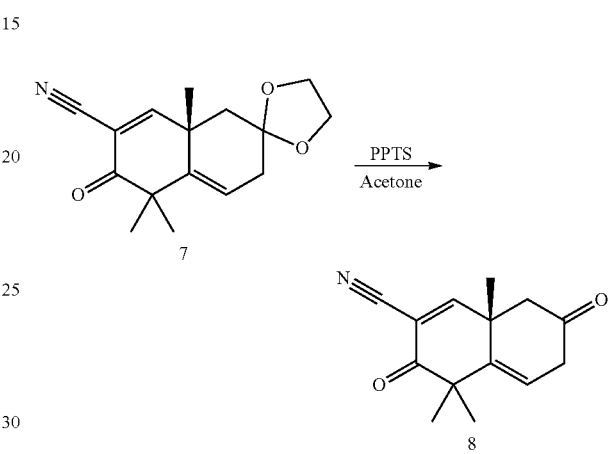

This reaction was run in two batches. A solution of 7 (160 mg, 0.59 mmol, 1.0 eq.) and PPTS (296 mg, 1.18 mmol, 2.0 eq.) in acetone (18 mL) and H$_2$O (2 mL) was stirred at 75° C. for 16 h. TLC (PE:EA=2:1) showed the starting material was consumed and new spot was detected. The reaction mixture was combined together with a second batch and concentrated to remove the acetone. Then EtOAc (15 mL) was added, followed by brine (10 mL). The two phases were separated, and the aqueous phase was extracted with EtOAc (10 mL×3). The combined organic phase was dried over Na$_2$SO$_4$, filtered, concentrated to give a crude product, which was purified by prep-HPLC (Column: Phenomenex Synergi C18 100×21.2 mm×4 um, Mobile phase: 0.225% FA in MeCN/H$_2$O, detection length: 220 nm) to give compound 8 (19.1 mg, 14.2%) as yellow solid.

$^1$H-NMR: (400 MHz, CDCl$_3$) δ: 7.24 (s, 1H), 5.85 (s, 1H), 3.10-2.95 (m, 2H), 2.46 (s, 3H), 1.45 (s, 3H), 1.42 (s, 3H), 1.40 (s, 3H).

HPLC: (purity: 80.96%, unstable in HPLC condition).
SFC: (purity: 95.26%).
LCMS: (M+H: 230.1).

Example 9. Synthesis of Compound 9

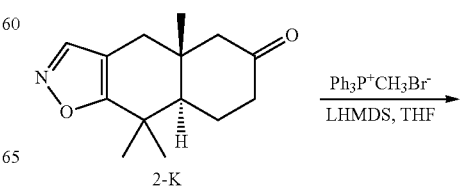

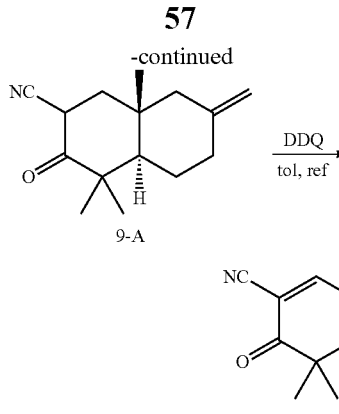

9-A

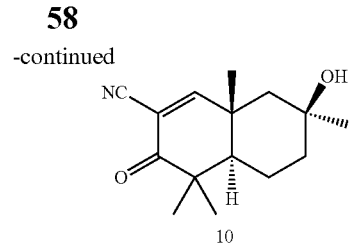

9

Preparation of Compound 9-A

To a suspension of methyl triphenylphosphonium bromide (1.43 g, 4 mmol, 4 eq) in THF (20 mL) was added 1 M LHMDS in THF (4 mL, 4 mmol, 4 eq) slowly. The yellow reaction suspension was stirred at 30° C. for 1 h, followed by addition of compound 2-K (233 mg, 1 mmol, 1 eq) in THF (2 mL). The resulting mixture was heated at 60° C. for 5 h. TLC (PE/EA=3:1) indicated the completion. Diluted with EA (40 mL), washed with water (20 mL×2). The organic phase was dried over $Na_2SO_4$, filtered, the filtrate was concentrated and then purified by column on silica gel eluted with PE:EA (10:1) to give the desired product of compound 9-A (53 mg, 23%) as colorless oil.

Preparation of Compound 9

To a solution of compound 9-A (53 mg, 0.23 mol, 1 eq) in toluene (2.5 mL) was added DDQ (57.4 mg, 0.253 mmol, 1.1 eq). The red suspension was refluxed for 2 h. TLC (PE:EA=6:1) indicated the completion. Diluted with EA (5 mL), filtered, the filter cake was washed with EA (5 mL). The combined organic phase was concentrated, and then purified by prep-TLC (PE:EA=6:1) to give the desired product of compound 9 (13 mg, 24.5%) as gum.

$^1$HNMR: (400 MHz, CHLOROFORM-d) δ: 7.34 (s, 1H), 4.80 (s, 1H), 4.68 (s, 1H), 2.42 (d, J=14.1 Hz, 1H), 2.15-2.07 (m, 1H), 2.05-1.92 (m, 2H), 1.80 (dd, J=2.3, 12.5 Hz, 1H), 1.73-1.64 (m, 1H), 1.46-1.39 (m, 1H), 1.16 (s, 3H), 1.06 (s, 3H), 1.00 (s, 3H).

HPLC: (purity 96.49%)

LCMS: (M+H: 230.0)

Example 10. Synthesis of Compound 10

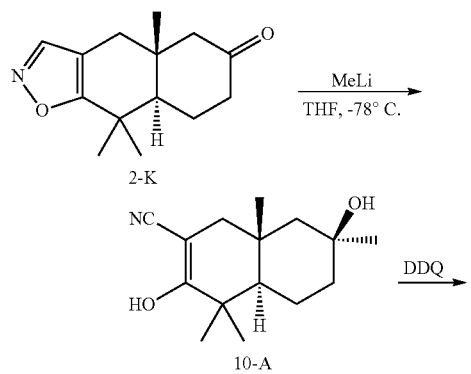

Preparation of Compound 10-A

To a solution of compound 2-K (500 mg, 2.15 mmol, 1.0 eq) in 20 mL of anhydrous THF was added MeLi (4.68 mL, 7.5 mmol, 3.5 eq, 1.6 M in $Et_2O$) at −70° C. After addition the mixture was stirred below −60° C. for 1 h. TLC (PE/EA=3:1) showed compound 2-K was consumed completely. The mixture was quenched by adding saturated aqueous $NH_4Cl$ (30 mL), diluted with brine, extracted with EtOAc (20 mL×3). The combined organic layer was washed with saturated aqueous $NH_4Cl$ (20 mL), dried over anhydrous $Na_2SO_4$, filtered, and concentrated under reduced pressure. The residue was purified by column chromatography on silica gel (PE:acetone=10:1) to supply compound 10-A (400 mg, 75% yield) as pale-yellow solid.

Preparation of Compound 10

To the solution of compound 10-A (400 mg, 1.6 mmol, 1.0 eq) in 20 mL of anhydrous toluene was added DDQ (365 mg, 1.6 mmol, 1.0 eq). The mixture was stirred at 110° C. for 2 h. TLC (PE/EA=2:1) showed only one spot was observed. The mixture was added methanol (10 mL), concentrated under reduced pressure. The residue was purified by column chromatography on silica gel (PE:acetone=10:1) to supply the crude compound 10 (360 mg), which was re-purified by prep-TLC (PE:EA=3:2) to supply compound 10 (200 mg). The obtained product was washed with MTBE to supply compound 10 (40 mg, 10.1% yield, purity: 96.05%) as white solid.

HPLC: (Purity: 96.05%)

SFC: (Purity: 96.22%)

MS: (M+H: 248.06)

$^1$H-NMR: (400 MHz, $CDCl_3$) δ: 7.47 (s, 1H), 1.91-1.79 (m, 2H), 1.68-1.64 (m, 2H), 1.62-1.55 (m, 1H), 1.53-1.39 (m, 5H), 1.27 (s, 3H), 1.22 (s, 3H), 1.14 (s, 3H), 1.07 (s, 1H).

Example 11. Synthesis of Compound 11

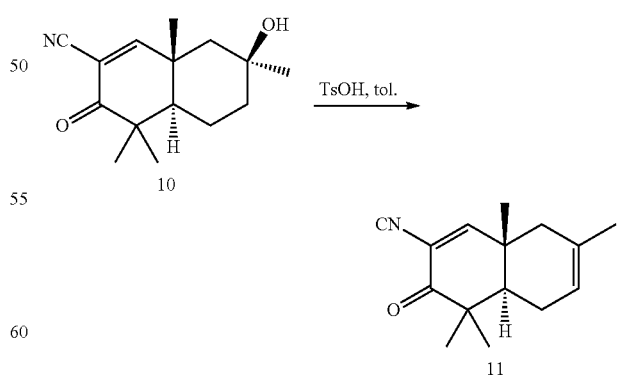

A mixture of compound 10 (80 mg, 0.324 mmol, 1.0 eq) and TsOH (28 mg, 0.164 mmol, 0.5 eq) in 3 mL of anhydrous toluene was stirred at 120° C. for 1 h. TLC (PE/EA=2:1) showed the compound 10 was consumed completely. The mixture was concentrated and purified by prep-TLC (PE:EA=4:1) to afford compound 11 (40 mg) as colorless solid.

HPLC: (Purity: 100%)
LCMS: (M+H: 230.0)
$^1$HNMR: (400 MHz, CDCl$_3$) δ: 7.41 (s, 1H), 5.48 (br. s., 1H), 2.18-2.00 (m, 3H), 1.97-1.89 (m, 1H), 1.76 (d, J=16.0 Hz, 1H), 1.69 (s, 3H), 1.20 (d, J=5.1 Hz, 6H), 1.11 (s, 3H).

Example 12. Synthesis of Compound 12

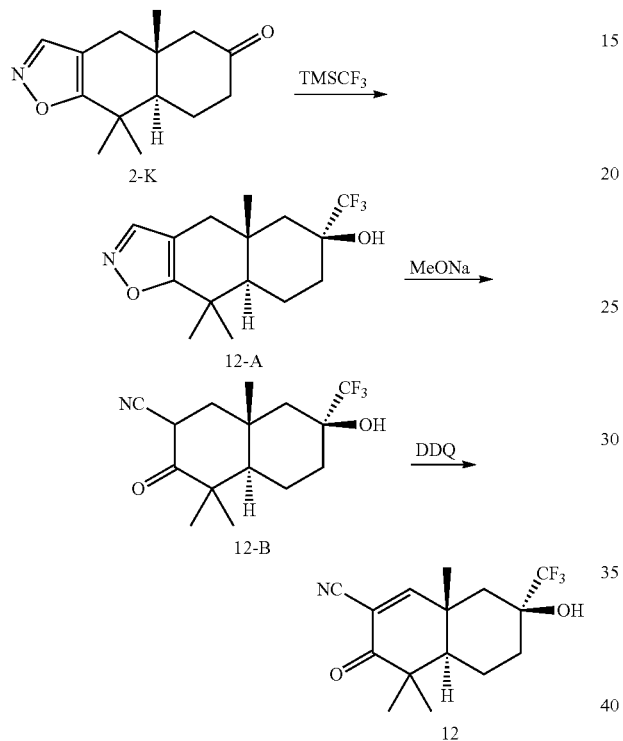

Preparation of Compound 12-A

To a solution of compound 2-K (400 mg, 1.71 mmol, 1 eq) and TMSCF$_3$ (291 mg, 2.05 mmol, 1.2 eq) in THF (5 mL) was added TBAF (0.17 mL, 0.17 mmol, 0.1 eq). The mixture was stirred at 25° C. for 18 hours. TLC (PE/EtOAc=5:1) showed the starting materials was consumed completely. The mixture was quenched with water (5 mL) and extracted with EA (10 mL×3). The combined organic phase was dried over sodium sulfate, and filtered. The filtrate was concentrated in vacuo to give the residue, which was purified by column chromatography on silica gel eluted with PE/EtOAc=20:1 to give compound 12-A (250 mg, 44.8%) as an off-white solid.

$^1$HNMR: (400 MHz, CDCl$_3$) δ: 8.02 (s, 1H), 2.35-2.31 (m, 1H), 2.22-2.14 (m, 1H), 1.98-1.91 (m, 1H), 1.81-1.69 (m, 5H), 1.65 (s, 1H), 1.47-1.51 (m, 1H), 1.34 (s, 3H), 1.24 (s, 3H), 1.12 (s, 3H).
LCMS: (M+H: 303.9)

Preparation of Compound 12-B

To a solution of compound 12-A (250 mg, 0.83 mmol, 1 eq) in MeOH (12 mL) was added NaOMe (179 mg, 3.32 mmol, 4 eq). The mixture was stirred at 25° C. for 16 hours. TLC (PE/EtOAc=2:1) showed the starting materials was consumed completely. The mixture was concentrated in vacuo to give the residue. The residue was taken up in water (15 mL) and extracted with EA (15 mL×3). The combined organic phase was dried over sodium sulfate and filtered. The filtrate was concentrated in vacuo to give compound 12-B (210 mg, crude), which was used directly in next step without purification.

Preparation of Compound 12

To a solution of compound 12-B (210 mg, 0.69 mmol, 1 eq) in toluene (5 mL) was added DDQ (233 mg, 1.03 mmol, 1.5 eq). The mixture was refluxed for 3 hours. TLC (PE/EtOAc=3:1) showed the starting materials was consumed completely. The mixture was concentrated in vacuo to give the residue. The residue was purified by column chromatography on silica gel (PE/EtOAc=5:1) and further purified by prep-TLC (PE/EtOAc=3:1) to give compound 12 (51 mg, 25%) as a white solid.

$^1$HNMR: (400 MHz, CDCl$_3$) δ: 7.47 (s, 1H), 1.97-1.91 (m, 1H), 1.90 (s, 1H), 1.85-1.82 (m, 2H), 1.76-1.71 (m, 4H), 1.45 (s, 3H), 1.25 (s, 3H), 1.15 (s, 3H).
HPLC: (Purity: 100%).
SFC: (de: 93.3%).
LCMS: (M+H: 302.1)

Example 13. Synthesis of Compound 13

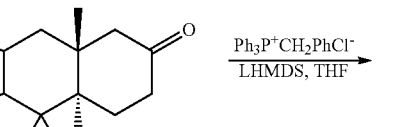

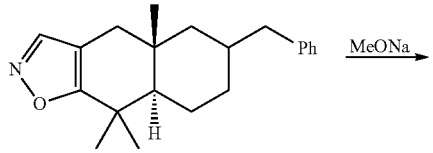

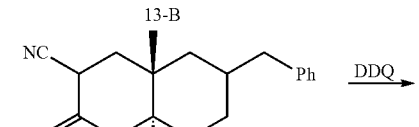

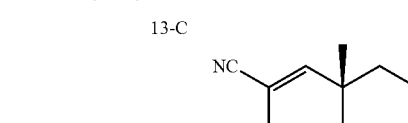

Preparation of Compound 13-A

To a suspension of compound 2-K (6.22 g, 16 mmol, 8 eq) in THF (90 mL) was added 1 M LHMDS in THF (16 mL, 16 mmol, 8 eq) dropwise. The resulting orange suspension was stirred at 25° C. for 1 h, followed by addition of benzyl triphenylphosphoniumchloride (466 mg, 2 mmol, 1 eq) in THF (10 mL) dropwise. The resulting mixture was stirred at 25° C. for additional 16 h. TLC (PE:EA=10:1) indicated the completion. The reaction mixture was concentrated, and the residue was diluted with EA (80 mL), washed with water (30 mL×3). The organic phase was dried over $Na_2SO_4$, filtered, the filtrate was concentrated and the residue was purified by flash column on silica gel with elution (PE to PE:EA=5:1) to give the desired product of compound 13-A (180 mg pure+ 150 mg mixture) as oil.

Preparation of Compound 13-B

To a solution of compound 13-A (31 mg, 0.1 mmol, 1 eq) in EtOAc (5 mL) was added 10% Pd/C (dry, 6 mg). The resulting mixture was purged with $H_2$ three times. Then the reaction mixture was stirred at 25° C. under a $H_2$-filled balloon for 18 h. The reaction mixture was filtered through Celite™, and the filtrate was concentrated to give the crude product 13-B (39 mg) as colorless oil.

$^1$H NMR: (400 MHz, CHLOROFORM-d) δ: 8.02 (s, 1H), 7.36-7.29 (m, 2H), 7.26-7.18 (m, 3H), 2.84-2.78 (m, 2H), 2.30-2.23 (m, 1H), 2.21-2.11 (m, 2H), 1.81 (d, J=13.3 Hz, 1H), 1.73-1.66 (m, 1H), 1.61 (d, J=6.3 Hz, 2H), 1.54-1.44 (m, 3H), 1.34 (s, 3H), 1.26 (s, 3H), 1.08 (s, 3H)

Preparation of Compound 13-C

To a solution of compound 13-B (140 mg, crude, 0.45 mmol, 1 eq) in MeOH (4.5 mL) was added NaOMe (72.9 mg, 1.35 mmol, 3 eq) slowly. The yellow mixture was stirred at 25° C. for 18 h. TLC (PE:EA=6:1) indicated the reaction had reached completion. The reaction was quenched by addition of HOAc to a pH at 6-7, and concentrated in vacuum. The residue was diluted with EA (20 mL), washed with water (10 mL×2), brine (10 mL). The organic phase was dried over $Na_2SO_4$, filtered, the filtrate was concentrated to give the crude product of compound 13-C (150 mg) as oil, which was directly use for next step.

Preparation of Compound 13

To a solution of compound 13-C (150 mg crude, 0.45 mol, 1 eq) in toluene (4.5 mL) was added DDQ (122.6 mg, 0.54 mmol, 1.2 eq). The resulting red suspension was refluxed for 2 h. TLC (PE:EA=6:1) indicated reaction completion. The reaction was filtered, and the filtrate was directly purified by prep-TLC (PE:EA=5:1) to give the desired product (80 mg, 58%) as oil. The obtained product was further purified by SFC (column: AD 250 mm×30 mm, 5 um; condition: 20% EtOH in $CO_2$; flow rate: 65 mL/min) to give the desired product of compound 13 (24.1 mg, 17%, Rt=3.48 min) as a gum. The relative stereochemistry was confirmed by 2D-NMR.

$^1$HNMR: (400 MHz, CHLOROFORM-d) δ: 7.41 (s, 1H), 7.33-7.25 (m, 2H), 7.23-7.17 (m, 1H), 7.14 (d, J=7.0 Hz, 2H), 2.72 (d, J=7.8 Hz, 2H), 2.20 (br. s., 1H), 1.79-1.70 (m, 2H), 1.69-1.60 (m, 3H), 1.56-1.46 (m, 2H), 1.36 (s, 3H), 1.19 (s, 3H), 1.11 (s, 3H).

HPLC: (purity 99.19%)
SFC: (de: 97.62%)
LCMS: (M+H: 308.2)

Example 14. Synthesis of Compound 14

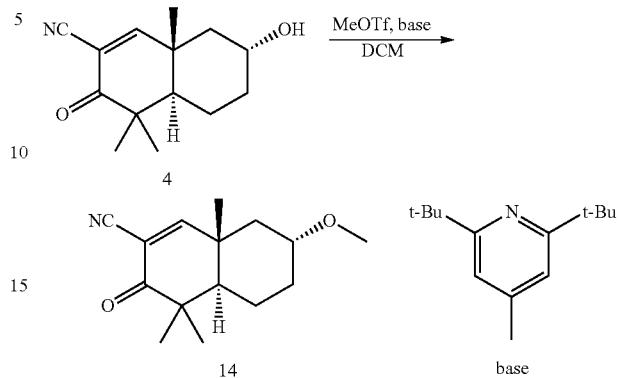

To a solution of compound 4 (38 mg, 0.16 mmol, 1.0 eq) and 2,6-di-tert-butyl-4-methylpyridine (328 mg, 1.6 mmol, 10 eq) in 6 mL of DCM was added methyl trifluoromethanesulfonate (214 mg, 1.3 mmol, 8.0 eq) The mixture was stirred at 21-23° C. for 20 h. TLC (PE:EA=2:1) showed compound 4 was consumed completely. The mixture was diluted with DCM (15 mL), washed with water (10 mL×3), dried over $Na_2SO_4$, filtered and concentrated under reduced pressure. The residue was purified by prep-TLC (PE/EA=2:1) to supply compound 14 (37.3 mg, 94% yield) as white solid.

HPLC: (Purity: 94.29%)
MS: (M+H: 248.1)
SFC: (de: 97.8%)
$^1$H-NMR: (400 MHz, CDCl$_3$) δ: 7.46 (s, 1H), 3.51-3.40 (m, 1H), 3.36 (s, 3H), 2.29 (d, J=11.7 Hz, 1H), 1.97 (dd, J=2.3, 12.0 Hz, 1H), 1.83-1.70 (m, 2H), 1.58-1.43 (m, 1H), 1.34-1.16 (m, 8H), 1.08 (s, 3H).

Example 15. Synthesis of Compound 15

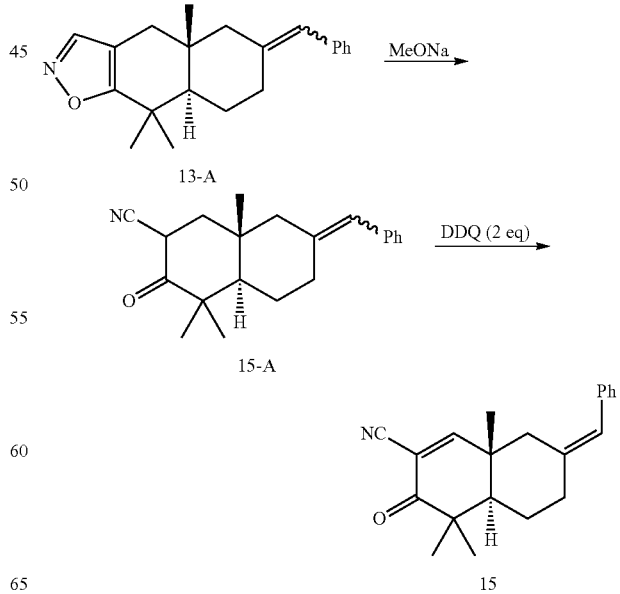

Preparation of Compound 15

To a solution of compound 13-A (240 mg, crude, 0.78 mmol, 1 eq) in MeOH (5 mL) was added NaOMe (84.4 mg, 1.56 mmol, 2 eq). The solution was stirred at 25° C. for 18 h. TLC (PE:EA=6:1) indicated the almost completion. Acidified the pH value to around 7, and concentrated in vacuum. The residue was diluted with EA (50 mL), washed with water (30 mL×3). The organic phase was dried over $Na_2SO_4$, filtered, the filtrate was concentrated to give the crude product of compound 15-A (260 mg) as oil, which was directly use for next step.

Preparation of Compound 15

To a solution of compound 15-A (410 mg crude, 1.33 mmol, 1 eq) in toluene (8 mL) was added DDQ (603.8 mg, 2.66 mmol, 2 eq). The resulting red suspension was refluxed for 2 h. TLC (PE:EA=6:1) indicated the reaction was mostly complete. The reaction was filtered, and the filter cake was washed with toluene (5 mL). The combined organic phase was concentrated to give the residue, which was purified by prep-TLC (PE:EA=6:1) twice to give the desired product (25 mg, 6.1%) as colorless oil. The obtained product combined with an additional batch and further purified by SFC (column: AD 250 mm×30 mm, 5 um; condition: 25% MeOH in $CO_2$; flow rate: 60 mL/min) to give the desired product of compound 15 (22 mg, Rt=3.62 min) as solid.

$^1$HNMR: (400 MHz, CHLOROFORM-d) δ: 7.52 (s, 1H), 7.35-7.27 (m, 2H), 7.24-7.13 (m, 3H), 6.47 (br. s., 1H), 6.33 (dd, J=2.7, 9.8 Hz, 1H), 5.68 (dd, J=2.2, 10.0 Hz, 1H), 2.87 (br. s., 1H), 2.73-2.66 (m, 1H), 2.57-2.50 (m, 1H), 1.25 (s, 3H), 1.08 (s, 3H), 1.07 (s, 3H).

HPLC: (purity 96.88%)

SFC: (purity: 94.29%)

LCMS: (M+H: 304.2)

Example 16. Synthesis of Compounds 16 and 17

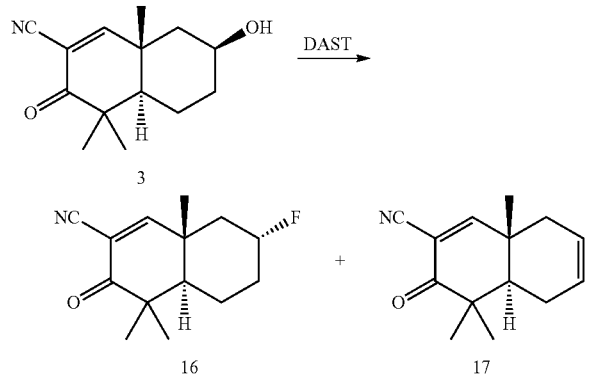

To the solution of compound 3 (300 mg, 1.29 mmol, 1.0 eq) in 15 mL of DCM was added DAST (2.15 g, 12.9 mmol, 10 eq) at −20° C.~−10° C. The mixture was allowed to warm to room temperature and stirred for 1 h. TLC (PE:EA=2:1) showed compound 3 was consumed completely. The mixture was diluted with DCM (20 mL), washed with water (15 M1×4). The organic layer was concentrated and purified by prep-TLC (PE:EA=6:1) to supply compound 16 (25.2 mg, 8.25% yield) as colorless solid, and 180 mg of a mixture of olefinic compounds. The mixture was further purified by prep-SFC (Mobile phase: 25% of Neu-IPA in $CO_2$; column: C2 250 mm×30 mm, 10 um) to supply compound 17 (100 mg, 36% yield) as colorless solid.

Data for 16:

HPLC: (Purity: 97.62%)

SFC: (purity: 98.61%)

MS: (M+H: 236.14)

$^1$HNMR: (400 MHz, $CDCl_3$) δ: 7.47 (s, 1H), 4.80 (m, 1H), 2.40-2.28 (m, 1H), 2.15-2.03 (m, 1H), 1.90-1.73 (m, 2H), 1.64-1.45 (m, 3H), 1.25 (d, J=6.3 Hz, 6H), 1.08 (s, 3H).

Data for 17:

HPLC: (Purity: 99.23%)

SFC: (de: 99.69%)

LCMS: (M+H: 216.1)

$^1$HNMR: (400 MHz, $CDCl_3$) δ: 7.40 (s, 1H), 5.79 (d, J=6.8 Hz, 1H), 5.68-5.53 (m, 1H), 2.22-2.08 (m, 3H), 2.08-1.98 (m, 1H), 1.98-1.87 (m, 1H), 1.24 (s, 3H), 1.20 (s, 3H), 1.12 (s, 3H).

Example 17. Synthesis of Compound 18

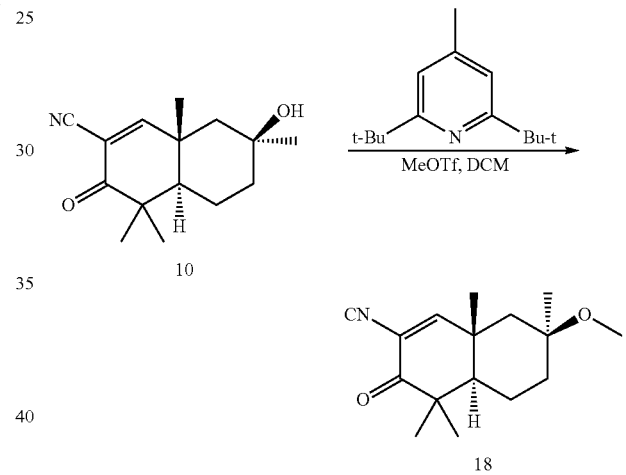

To the solution of compound 10 (100 mg, 0.4 mmol, 1.0 eq) and 2,6-di-tert-butyl-4-methylpyridine (1.31 g, 6.4 mmol, 16 eq) in 20 mL of DCM was added compound methyl trifluoromethanesulfonate (527 mg, 3.2 mmol, 8.0 eq) at 0-5° C. After addition the mixture was stirred at 14-18° C. for 2 days. TLC (PE/EA=2:1) showed about 30% of compound 10 remained. The mixture was diluted with DCM (30 mL), washed with water (20 mL×4), concentrated under reduced pressure. The residue was purified by column chromatography on silica gel (PE:EA=15:1-10:1-6:1) to recover compound 10 (44 mg) as white solid and afford 80 mg of impure compound 18, re-purified by prep-TLC (PE:EA=3:1) to supply 18 (34.4 mg, 33% yield) as colorless solid.

HPLC: (Purity: 100%)

MS: (M+H: 262.1)

SFC: (ee: 100%)

$^1$H-NMR: (400 MHz, $CDCl_3$) δ: 7.47 (s, 1H), 3.18 (s, 3H), 2.09 (dd, J=2.3, 14.1 Hz, 1H), 1.89 (dd, J=2.3, 14.1 Hz, 1H), 1.78-1.63 (m, 2H), 1.53 (d, J=11.3 Hz, 1H), 1.37 (s, 3H), 1.32-1.25 (m, 2H), 1.22 (s, 3H), 1.14 (d, J=8.2 Hz, 6H).

Example 18. Synthesis of Compound 19

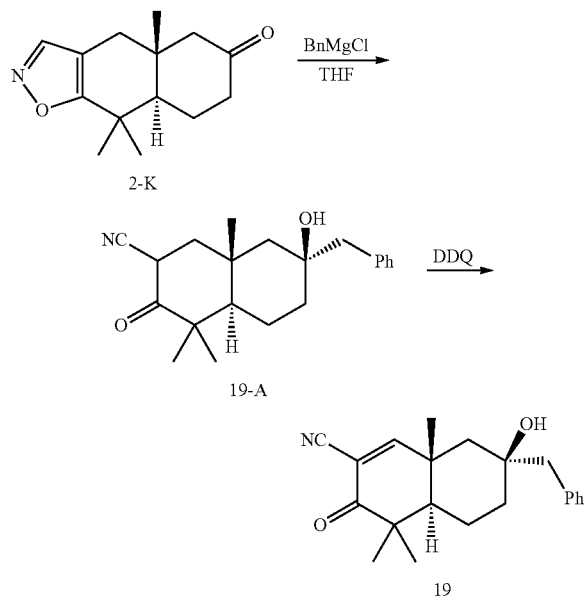

Preparation of Compound 19-A

To a solution of compound 2-K (350 mg, 1.5 mmol, 1 eq) in anhydrous THF (15 mL) was added 2 M PhCH$_2$MgCl in THF (7.5 mL, 15 mmol, 10 eq) at 20° C. The resulting clean brown solution was stirred at 20° C. for 18 h. TLC (PE: EA=6:1) indicated the completion. The reaction mixture was quenched by saturated NH$_4$Cl (30 mL), concentrated in vacuum to remove the solvent THF. Extracted with EA (20 mL×3). The combined organic phase was dried over Na$_2$SO$_4$, filtered, the filtrate was concentrated to give the crude product which was purified by column chromatography on silica gel eluted with PE to PE:EA=5:1 to give the desired product of compound 19-A (500 mg, >100%) as white solid.

$^1$H NMR: (400 MHz, CDCl$_3$) δ: 7.39-7.25 (m, 3H), 7.20-7.04 (m, 2H), 6.05 (br. s., 0.5H), 3.99-3.79 (m, 0.5H), 2.75-2.58 (m, 2H), 2.20-1.86 (m, 2H), 1.74-1.64 (m, 2H), 1.55-1.37 (m, 3H), 1.34-1.19 (m, 3H), 1.17-0.99 (m, 9H).

Preparation of Compound 19

A suspension of compound 19-A (500 mg, 1.5 mmol, 1 eq) and DDQ (510.75 mg, 2.25 mmol, 1.5 eq) in toluene (30 mL) was refluxed for 2 h. TLC (PE:EA=4:1) indicated the same spot, but strong UV absorption. Filtered, the filtrate was concentrated and the residue was purified by column chromatography on silica gel eluted with PE:EA=6:1 to give the desired product of compound 19 (400 mg, 82.5%) as reddish brown solid.

$^1$HNMR: (400 MHz, CD$_3$CN) δ: 7.66 (s, 1H), 7.35-7.20 (m, 5H), 2.76-2.67 (m, 2H), 2.36 (s, 1H), 1.84-1.65 (m, 3H), 1.64-1.44 (m, 4H), 1.36 (s, 3H), 1.18 (s, 3H), 1.09 (s, 3H).

HPLC: (purity 95.55%)
MS: (M+H: 324.2)

Example 19. Synthesis of Compound 20

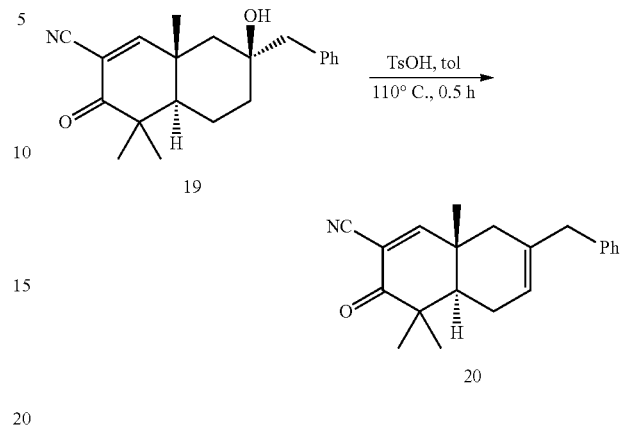

To a solution of compound 19 (97 mg, 0.3 mmol, 1 eq) in toluene (3 mL) was added TsOH (25.8 mg, 0.15 mmol, 0.5 eq). The red solution was refluxed for 0.5 h. TLC (PE:EA=4:1) indicated the completion. The reaction mixture was diluted with EA (20 mL), washed with water (10 mL), saturated NaHCO$_3$ (10 mL), dried over Na$_2$SO$_4$, filtered, and the filtrate was concentrated to give the reddish brown oil (around 100 mg) which was purified by prep-TLC (PE: EA=6:1) twice to give the desired product (90 mg, 97.8%, still impure by NMR and SFC) as colorless oil. This product was further purified by SFC (column: OD 250 mm×30 mm, 5 um; condition: 25% EtOH in CO$_2$; flow rate: 60 mL/min) to give the desired product of compound 20 (63 mg, Rt=3.165 min) as solid.

$^1$HNMR: (400 MHz, CHLOROFORM-d) δ: 7.31-7.24 (m, 3H), 7.22-7.16 (m, 1H), 7.12 (d, J=7.0 Hz, 2H), 5.58 (br. s., 1H), 3.34-3.17 (m, 2H), 2.22-2.05 (m, 2H), 2.04-1.86 (m, 2H), 1.69 (d, J=16.4 Hz, 1H), 1.17 (s, 3H), 1.10 (s, 3H), 1.07 (s, 3H).

HPLC: (purity 100%)
LCMS: (M+H: 306.1)

Example 20. Synthesis of Compound 21

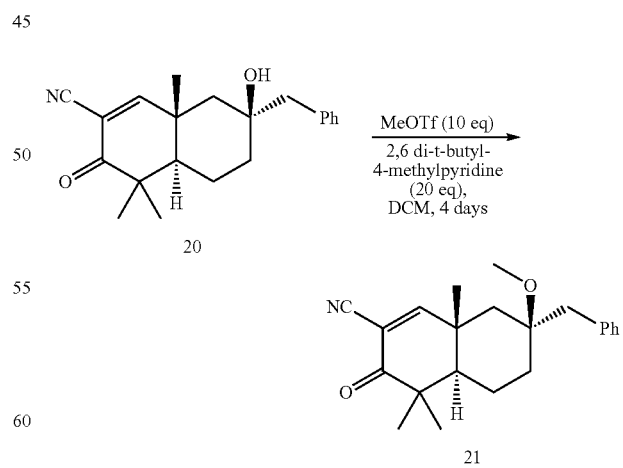

To a solution of compound 20 (164 mg, 0.5 mmol, 1 eq) and 2,6-Di-tert-butyl-4-methylpyridine (2.05 g, 10 mmol, 20 eq) in DCM (25 mL) was added MeOTf (0.82 g, 5 mmol, 10 eq) at 0° C. The resulting mixture was stirred at 15-20° C.

for 4 days. TLC (PE:EA=4:1) indicated more than 50% of 20 remained. The reaction mixture was washed with water (20 mL×3), dried over Na₂SO₄, filtered, and the filtrate was concentrated to give the crude product which was purified by column chromatography on silica gel eluted with PE:EA (10:1 to 5:1) to give the desired product (40 mg, 23.7%) as oil, and compound 21 (140 mg) was recovered. The obtained desired product was re-purified by P-TLC (PE:EA=2:1) to give the product of compound 21 (35.4 mg, 21%) as gum.

¹HNMR: (400 MHz, CDCl₃) δ: 7.41 (s, 1H), 7.33-7.19 (m, 3H), 7.11 (d, J=7.0 Hz, 2H), 3.31 (s, 3H), 2.81 (d, J=13.7 Hz, 1H), 2.64 (d, J=13.7 Hz, 1H), 2.11-1.99 (m, 1H), 1.74-1.59 (m, 2H), 1.56-1.45 (m, 2H), 1.34-1.23 (m, 5H), 1.14 (s, 3H), 1.08 (s, 3H).

HPLC: (purity 98.98%)

LCMS: (M+Na: 360)

Example 21. Synthesis of Compound 22

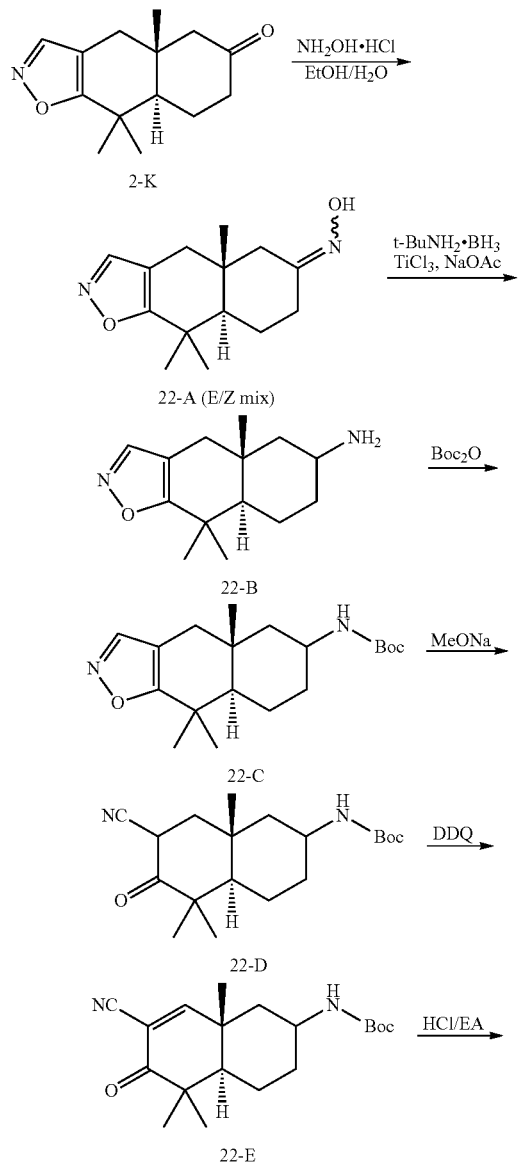

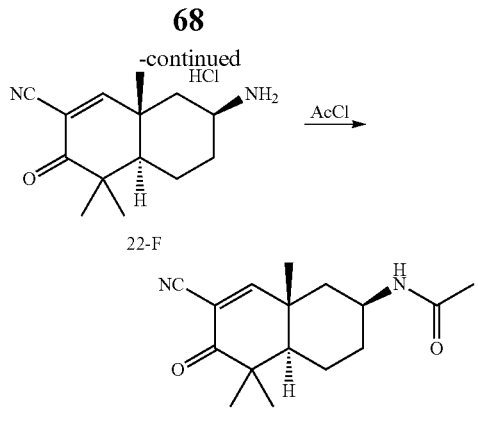

Preparation of Compounds 22-A Isomer 1 and 22-A Isomer 2

Compound 2-K (2.30 g, 9.86 mmol) and Hydroxylamine hydrochloride (822.21 mg, 11.83 mmol, 492.34 uL) were combined in 30 mL of ethanol and heated to 50° C. After 2 h, the reaction was concentrated to dryness and deposited on O1 g silica gel. The reaction was purified by silica gel chromatography using a 25-35% gradient of ethyl acetate in heptane to afford two white crystalline solids. The first eluting isomer was assigned the structure of compound 22-A Isomer 1 (900.00 mg, 3.62 mmol, 36.76% yield) The second eluting isomer was called compound 22-A Isomer 2 (1.10 g, 4.43 mmol, 44.93% yield). A mixture of the two oxime isomers was used in the next step.

Data for 22-A Isomer 1:

¹H NMR (400 MHz, CHLOROFORM-d) δ: 8.06 (s, 1H) 6.79 (s, 1H) 3.34 (dd, J=13.4, 2.4 Hz, 1H) 2.52-2.59 (m, 1H) 2.41 (d, J=2.0 Hz, 2H) 2.15 (td, J=13.5, 5.1 Hz, 1H) 1.93-2.00 (m, 1H) 1.62-1.80 (m, 3H) 1.57 (s, 1H) 1.38 (s, 3H) 1.23 (s, 3H) 0.92 (s, 3H).

Data for 22-A Isomer 2:

¹H NMR (400 MHz, CHLOROFORM-d) δ: 8.03-8.06 (m, 1H) 7.26 (s, 1H) 3.54 (ddt, J=14.2, 4.4, 2.1, 2.1 Hz, 1H) 2.33-2.41 (m, 2H) 2.25 (dd, J=13.4, 2.1 Hz, 1H) 2.10 (d, J=13.6 Hz, 1H) 1.93 (ddt, J=13.0, 5.5, 2.7, 2.7 Hz, 1H) 1.54-1.80 (m, 4H) 1.38-1.40 (m, 3H) 1.20-1.24 (m, 3H) 0.90 (s, 3H)

Preparation of Compound 22-B

Compound 22-A (Z/E mixture) (1.0 g, 4.03 mmol, 1.0 eq) in 20 mL of ethanol was added into the solution of sodium acetate (2.83 g, 34.5 mmol, 8.56 eq) and TiCl₃ (2.09 g, 13.7 mmol, 3.4 eq) in 10.5% aq.HCl (40 mL) at −20° C.~−10° C. by dropwise. The addition was conducted below 0° C. The mixture was stirred at 0° C. for 1 h. Compound t-BuNH₂.BH₃ (876 mg, 10.8 mmol, 2.5 eq) was added by portion wise at 0° C. The mixture was stirred at 20° C.~24° C. for 18 h. LCMS showed a little messy. The mixture was diluted with water (50 mL), adjusted pH to 8 by adding saturated aqueous NaHCO₃, filtered through a pad of celite. The filtrate was concentrated under reduced pressure, the residue was slurried with methanol (200 mL), filtered, concentrated to supply crude compound 22-B (4.0 g) which was used for next step directly.

LCMS: (M+H: 235.2)

Preparation of Compound 22-C

To the mixture of compound 22-B (940 mg, 4.0 mmol, 1.0 eq) in 30 mL of DCM was added (Boc)₂O (1.74 g, 8.0 mmol, 2.0 eq) and TEA (811 mg, 8.0 mmol, 2.0 eq). The mixture was stirred at 18° C.~24° C. for 24 h. TLC (PE/EA=4:1) showed one new spot was observed. The mixture was diluted with water (80 mL), extracted with DCM (30 mL×4). The combined organic layer was concentrated under reduced pressure and the residue was purified by column chromatography on silica gel (PE:EA=30:1-20:1-10:1) to supply compound 22-C (160 mg, 12% yield) as pale-yellow gum.

LCMS: (M+H: 335.1)

$^1$HNMR: (400 MHz, CDCl$_3$) δ: 8.02 (s, 1H), 4.69 (br. s., 1H), 3.89 (br. s., 1H), 2.33-2.10 (m, 2H), 1.98 (br. s., 2H), 1.68-1.54 (m, 5H), 1.46 (s, 9H), 1.33 (s, 3H), 1.21 (s, 3H), 1.02 (s, 3H).

Preparation of Compound 22-D

To a mixture of compound 22-C (220 mg, 0.656 mmol, 1.0 eq) in 1 mL of anhydrous methanol was added NaOMe (1.9 mL, 3.9 mmol, 6.0 eq, 2 M in methanol). The mixture was stirred at 14° C.~18° C. for 18 h. TLC (PE/EA=3:1) showed little compound 22-C remained.

The mixture was diluted with water (20 mL) and extracted with EtOAc (10 mL×3). The combined organic layer was washed with brine (10 mL), dried over anhydrous Na$_2$SO$_4$, filtered, concentrated under reduced pressure to supply crude compound 22-D (180 mg) as pale-yellow gum.

Preparation of Compound 22-E

To a solution of compound 22-D (180 mg, 0.54 mmol, 1.0 eq) in 6 mL of anhydrous toluene was added DDQ (122 mg, 0.54 mmol, 1.0 eq). The mixture was stirred at 110° C. for 2 h. TLC (PE/EA=3:1) showed compound 22-D was consumed completely. The mixture was concentrated under reduced pressure and purified by prep-TLC (PE:EA=3:1) to supply compound 22-E (80 mg, 45% yield) as pale-yellow solid.

HPLC: (purity: 82%)
LCMS: (M+Na: 354.9)

$^1$HNMR: (400 MHz, CDCl$_3$) δ: 7.46 (s, 1H), 4.52 (br. s, 1H), 3.93 (br. s, 1H), 2.17-1.96 (m, 1H), 1.93-1.74 (m, 1H), 1.65-1.63 (m, 5H), 1.46 (s, 9H), 1.36 (s, 3H), 1.22 (s, 3H), 1.12 (s, 3H).

Preparation of Compound 22-F

Compound 22-E (100 mg, 0.3 mmol, 1.0 eq) was added into 6 mL of HCl/EtOAc (about 4 M). The mixture was stirred at 12° C.~16° C. for 18 h. TLC (PE/EA=3:1) showed compound 22-E was consumed completely. The mixture was concentrated under reduced pressure to supply crude compound 22-F (60 mg, 74% yield) as an HCL salt. If desired, crude compound 22-F may be purified by SFC (mobile phase: A: CO$_2$, B: ethanol with 0.05% NH$_3$.H$_2$O, column: AD: 250 mm*30 mm, 5 um) to supply impure compound 22-F. Impure compound 22-F was re-purified by prep-HPLC (condition: water with 0.05% HCl-ACN, column: Phenomenex Synergi C18 150*30 mm*4 um) to supply pure compound 22-F as white solid.

HPLC: (purity: 100%)
SFC: (purity: 98.58%)
LCMS: (M+H: 233.1)

$^1$HNMR: (400 MHz, MeOD) δ: 7.74 (s, 1H), 3.66 (br. s., 1H), 2.02-1.85 (m, 5H), 1.78 (br. s., 2H), 1.39 (s, 3H), 1.23 (s, 3H), 1.12 (s, 3H).

Preparation of Compound 22

To the mixture of crude compound 22-F (60 mg, 0.26 mmol, 1.0 eq) in 5 mL of anhydrous DCM was added TEA (105 mg, 1.04 mmol, 4.0 eq) and AcCl (61 mg, 0.77 mmol, 3.0 eq). The mixture was stirred at 12~16° C. for 18 h. TLC (PE:EA=1:5) showed one main spot was observed. The mixture was diluted with water (15 mL), extracted with EtOAc (10 mL×3). The combined organic layer was washed with brine (10 mL), dried over anhydrous Na$_2$SO$_4$, filtered, and concentrated under reduced pressure. The residue was purified by prep-TLC (PE:EA=1:10) to supply crude compound 22 (40 mg). Impure compound 22 was re-purified by prep-SFC (condition: base-EtOH (0.1% NH$_3$.H$_2$O); column: AD, 250 mm*30 mm, 5 um; 220 nm) to supply compound 22 (21.7 mg, 30.5% yield) as pale-yellow solid.

HPLC: (purity: 99.91%)
SFC: (ee: 98.86%)
LCMS: (M+H: 275.1)

$^1$HNMR: (400 MHz, CDCl$_3$) δ: 7.44 (s, 1H), 5.57 (br. s., 1H), 4.19 (br. s., 1H), 2.14 (d, J=14.1 Hz, 1H), 2.00 (s, 3H), 1.94 (d, J=14.1 Hz, 1H), 1.81-1.54 (m, 6H), 1.34 (s, 3H), 1.23 (s, 3H), 1.11 (s, 3H).

Example 22. Synthesis of Compound 23

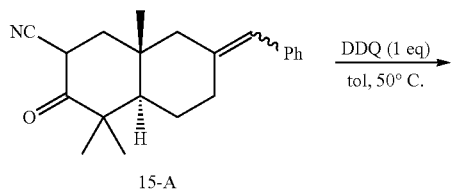

15-A

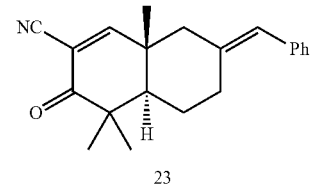

23

A red suspension of compound 15-A (150 mg crude, 0.49 mmol, 1 eq) and DDQ (122.3 mg, 0.54 mmol, 1.1 eq) in anhydrous toluene (4 mL) was heated at 50° C. for 1 h. TLC (PE:EA=6:1) indicated the completion. The reaction mixture was directly purified by P-TLC (PE:EA=4:1) to give a impure 23. The mixture combined with an additional batch (25 mg), and purified by SFC (column: AD 250 mm×30 mm, 5 um; condition: 30% MeOH in CO$_2$; flow rate: 60 mL/min) to give the desired product of compound 23 (12.1 mg, Rt=4.97 min) as gum.

$^1$HNMR: (400 MHz, CDCl$_3$) δ: 7.40 (s, 1H), 7.32-7.22 (m, 2H), 7.21-7.10 (m, 3H), 6.26 (br. s., 1H), 3.02 (d, J=14.1 Hz, 1H), 2.32 (d, J=12.9 Hz, 1H), 2.10 (d, J=12.5 Hz, 1H), 1.95-1.86 (m, 2H), 1.72-1.62 (m, 1H), 1.44 (dt, J=4.3, 12.9 Hz, 1H), 1.17 (s, 3H), 1.13 (s, 3H), 1.00 (s, 3H).

HPLC: (purity 94.29%)
MS: (M+H: 306)

Example 23. Synthesis of Compound 24

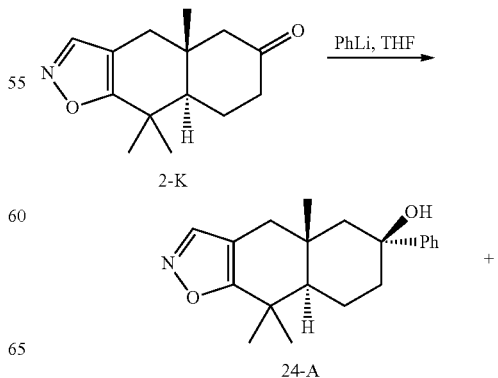

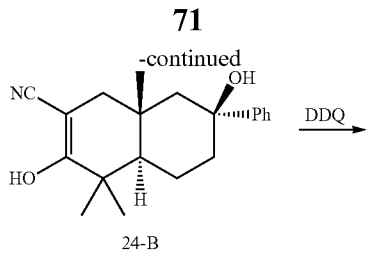

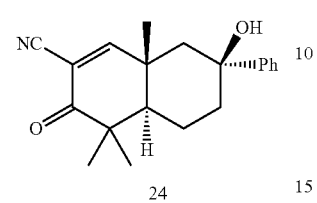

Preparation of Compounds 24-A and 24-B

To a solution of compound 2-K (400 mg, 1.72 mmol, 1.0 eq.) in THF (8.0 mL) was added PhLi (4.52 mL, 8.6 mmol, 5.0 eq.) dropwise at −78° C. under N$_2$, and the reaction mixture was stirred at −78° C. for 4 h. LCMS showed the starting material was consumed and the desired product was detected. Saturated NH$_4$Cl (5 mL) was added to quench the reaction, followed by EtOAc (10 mL) and H$_2$O (5 mL). The two phases were separated, and the aqueous phase was extracted with EtOAc (10 mL×3). The combined organic phase was dried over Na$_2$SO$_4$, filtered, concentrated to give a crude product, which was purified by column chromatography (PE/EA=20:1 to 2:1) to give compound 24-A (270 mg, 50.6%) and compound 24-B (160 mg, crude) as yellow oil.

Preparation of Compound 24

A reaction mixture of compound 24-B (160 mg, 0.51 mmol, 1.0 eq.) and DDQ (173 mg, 0.76 mol, 1.5 eq.) in PhMe (30 mL) was stirred under reflux for 2 h. TLC (PE/EA=2:1) showed the starting material was consumed with new spot detected. The solvent was concentrated to give a crude product, which was purified by column chromatography (PE/EA=10:1 to 2:1) to give a crude product of compound 24 (180 mg). 90 mg of compound 24 was further purified by prep-HPLC (Column: Phenomenex Gemini C18 250×21.2 mm×5 um. Condition: water with 10 mM NH$_4$HCO$_3$-ACN) to give compound 24 (7.3 mg) as white solid.

LCMS: (M+Na: 332.2)

HPLC: (purity: 97.83%)

$^1$H-NMR: (CD$_3$CN, 400 MHz) δ: 7.67 (s, 1H), 7.48 (d, J=7.6 Hz, 2H), 7.34 (t, J=7.6 Hz, 2H), 7.24 (t, J=7.6 Hz, 1H), 3.07 (s, 1H), 1.98 (m, 2H), 1.88-1.86 (m, 3H), 1.78-1.75 (m, 1H), 1.67-1.65 (m, 1H), 1.49 (s, 3H), 1.23 (s, 3H), 1.14 (s, 3H).

Example 24. Synthesis of Compound 25

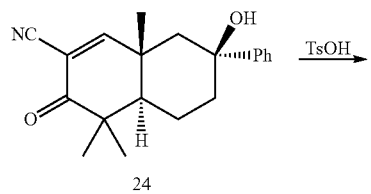

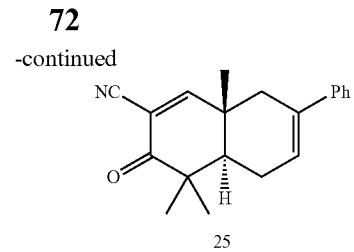

A mixture of compound 24 (60 mg, 0.19 mmol, 1.0 eq.) and p-TsOH (6.9 mg, 0.04 mmol, 0.2 eq.) in PhMe (10 mL) was stirred under reflux for 1 h. TLC (PE/EA=3:1) showed the starting material was consumed. The mixture was concentrated to give a crude product, which was purified by prep-HPLC (PE/EA=4:1) To give compound 25 (18.8 mg, 33.3%) as white solid.

$^1$H-NMR: CDCl$_3$, 400 MHz) δ: 7.50 (s, 1H), 7.34-7.28 (m, 5H), 6.15 (s, 1H), 2.58-2.55 (m, 1H), 2.36-2.31 (m, 3H), 2.13-2.09 (m, 1H), 1.29 (s, 3H), 1.25 (s, 3H), 1.16 (s, 3H).

HPLC: (purity: 97.29%).

LCMS: (M+H: 292.2)

Example 25. Synthesis of Compound 26

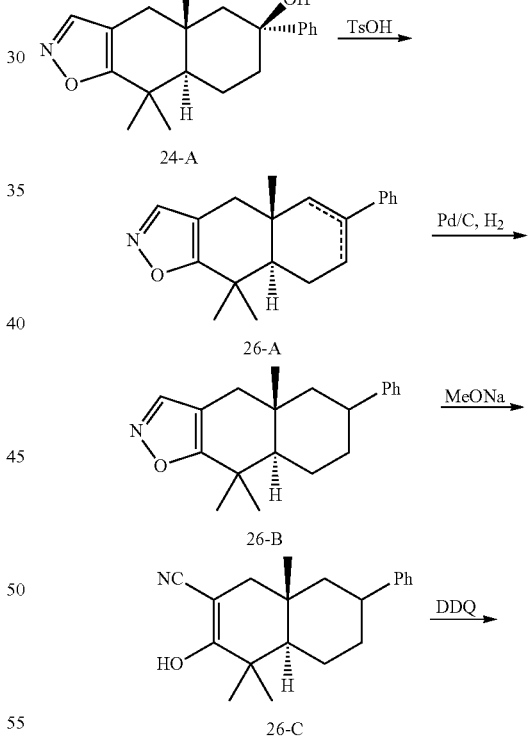

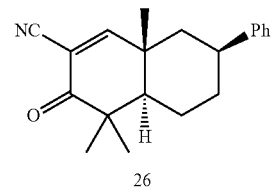

Preparation of Compound 26-A

A reaction mixture of compound 24-A (270 mg, 0.87 mmol, 1.0 eq) and p-TsOH (29.2 mg, 0.17 mmol, 0.2 eq.) in THF (8.0 mL) and PhMe (8 mL) was stirred under reflux for 1 h. TLC (PE/EA=3:1) showed the starting material was consumed with a new spot detected. The solvent was concentrated to give a residue. EtOAc (10 mL) and saturated NaHCO$_3$ (5 mL) were added. The two phases were separated, and the aqueous phase was extracted with EtOAc (5 mL×3). The combined organic phase was dried over Na$_2$SO$_4$, filtered, concentrated to give a crude product of compound 26-A (250 mg, 98.4%, isomeric mixture) as yellow solid.

$^1$H-NMR: (CDCl3, 400 MHz) δ: 8.04 (s, 1H), 7.40-7.29 (m, 4H), 7.23-7.17 (m, 1H), 6.12/5.83 (s, 1H), 2.60-2.47 (m, 2H), 2.40-2.33 (m, 3H), 1.93-1.90 (m, 1H), 1.76-1.71 (m, 1H), 1.36 (s, 3H), 1.28/1.25 (s, 3H), 1.00/0.94 (s, 3H).

Preparation of Compound 26-B

To a solution of compound 26-A (250 mg, 0.85 mmol, 1.0 eq.) in EtOAc (10 mL) was added Pd/C (0.5 g) at 25° C. Then the reaction mixture was charged with H$_2$ for 3 times, and the reaction mixture was stirred at 25° C. for 2 h. TLC (PE/EA=3:1) showed a little starting material was remained with new spot detected. The solid was filtered off, washed with EtOAc (20 mL). The combined organic phase was concentrated to give a crude product of compound 26-B (250 mg, crude), which was used for the next step without any further purification.

$^1$H-NMR: (CDCl3, 400 MHz) δ: 7.58 (s, 1H), 7.02-7.00 (m, 2H), 6.942-6.83 (m, 2H), 6.79-6.77 (m, 1H), 2.80 (br.s, 1H), 2.18-2.16 (m, 1H), 1.86-1.83 (m, 3H), 1.43-1.39 (m, 4H), 1.37-1.35 (m, 1H), 0.95 (s, 3H), 0.73 (s, 3H), 0.00 (s, 3H).

Preparation of Compound 26-C

To a solution of compound 26-B (250 mg, 0.85 mmol, 1.0 eq.) in MeOH (2 mL) was added MeONa (2M, 1.275 mL, 2.55 mmol, 3.0 eq.) at 25° C., and the reaction mixture was stirred at 25° C. for 16 h. TLC (PE/EA=4:1) showed the starting material was consumed with new spot detected. The solvent was concentrated. EtOAc (10 mL) and H$_2$O (10 mL) was added, the two phases were separated. The aqueous phase was extracted with EtOAc (10 mL×3). The combined organic phase was dried over Na$_2$SO$_4$, filtered, concentrated to give a crude product, which was purified by column chromatography (PE/EA=4:1) to give a crude product of compound 26-C (200 mg, 80%) as colorless oil, which was used for the next step without any further purification.

Preparation of Compound 26

A reaction mixture of compound 26-C (160 mg, 0.54 mmol, 1.0 eq.) and DDQ (122.6 mg, 0.54 mmol, 1.0 eq.) in PhMe (10 mL) was stirred at 50° C. for 1 h. TLC (PE/EA=4:1) showed the a little starting material was remained with new spot detected. The solid was filtered off, the filtrate was concentrated to give a crude product, which was purified (combined with batch 19225-147-1) by prep-TLC (PE/EA=4:1) to give compound 26 (12.0 mg, 7.6%) as white solid.

$^1$H-NMR: (400 MHz, CD$_3$CN) δ: 7.62 (s, 1H), 7.43-7.42 (m, 2H), 7.36-7.32 (m, 2H), 7.22-7.20 (m, 1H), 3.24 (br s, 1H), 2.47-2.45 (m, 1H), 2.16-2.12 (m, 1H), 2.04-2.00 (m, 2H), 1.85-1.78 (m, 3H), 1.21 (s, 3H), 1.03 (s, 3H), 0.83 (s, 3H).

HPLC: (98.87%).

MS: (M+H: 294.18).

Example 26. Synthesis of Compound 27

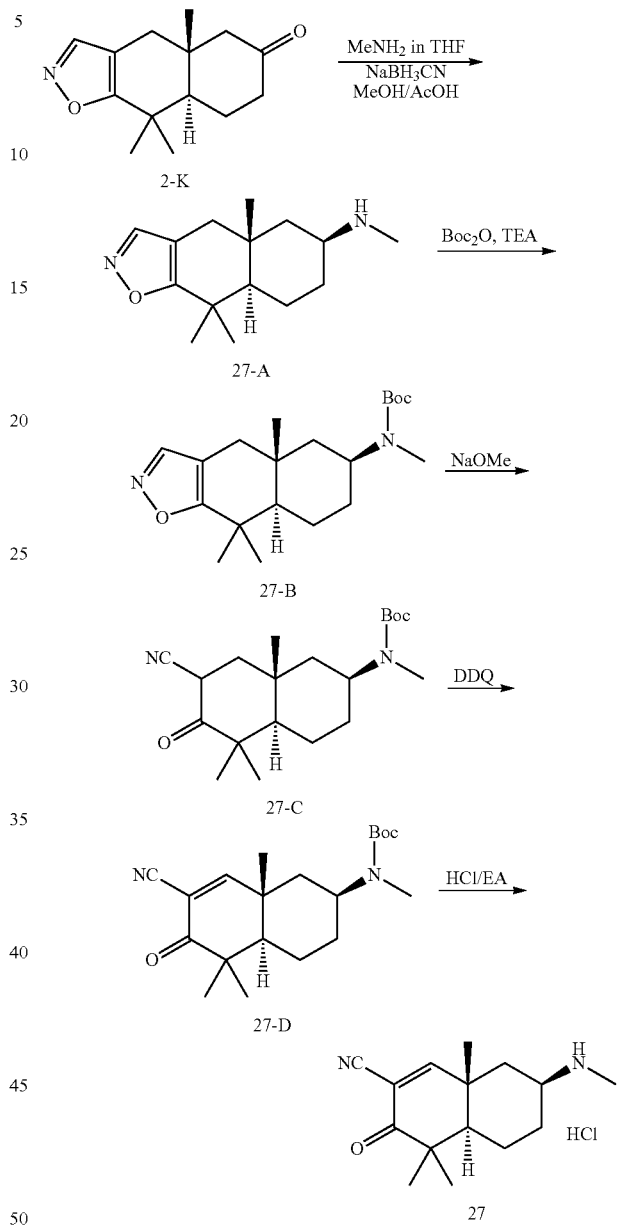

Preparation of Compound 27-A

To a suspension of compound 2-K (233 mg, 1 mmol, 1 eq) and HOAc (0.5 mL) in MeOH (8 mL) was added 1 M MeNH$_2$ in THF (5 mL, 5 mmol, 5 eq). The resulting mixture was stirred at 15° C. for 1 h, NaBH$_3$CN (95 mg, 1.5 mmol, 1.5 eq) was added to the mixture, and stirred at 15° C. for additional 2 h. TLC (PE:EA=2:1) indicated reaction completion. The reaction mixture was concentrated to remove the excess MeNH$_2$. The residue was diluted with MeOH (5 mL), then TEA (303 mg, 3 mmol, 3 eq) and Boc$_2$O (432 mg, 2 mmol, 2 eq) was added to the mixture and stirred at 10° C. for 18 h. LCMS indicated still major compound 27-A (only trace Boc protected product of compound 27-B). The reaction mixture was concentrated to remove the solvent, diluted with saturated NaHCO$_3$ (20 mL), extracted with EA (15 mL×4). The combined organic phase was dried over Na$_2$SO$_4$, filtered, the filtrate was concentrated to give the crude product 27-A (430 mg) as colorless oil.

Preparation of Compound 27-B

To a solution of compound 27-A (430 mg crude, 1 mmol, 1 eq) in DCM (8 mL) was added Boc$_2$O (432 mg, 2 mmol, 2 eq) and DMAP (122 mg, 1 mmol, 1 eq). The colorless solution was stirred at 4-10° C. for 2 days. TLC (PE:EA=4:1) and LCMS indicated the desired product. The reaction mixture was concentrated and the residue was purified by column on silica gel with elution PE:EA (10:1) to give the desired product of compound 27-B (350 mg, 100%) as colorless oil.

$^1$H NMR: (400 MHz, CHLOROFORM-d) δ: 7.94 (s, 1H), 4.11 (br. s., 1H), 2.74 (s, 3H), 2.67 (d, J=4.7 Hz, 1H), 2.30 (d, J=15.3 Hz, 1H), 2.13 (d, J=15.3 Hz, 1H), 1.93-1.76 (m, 2H), 1.76-1.59 (m, 2H), 1.58-1.52 (m, 2H), 1.40 (s, 9H), 1.23 (s, 3H), 1.13 (s, 3H), 0.84 (s, 3H).

Preparation of Compound 27-C

To a solution of MeONa (162 mg, 3 mmol, 3 eq) in MeOH (10 mL) was added compound 27-B (350 mg, 1 mmol, 1 eq) in MeOH (5 mL). The resulting mixture was stirred at 10° C. for 18 h. TLC (PE:EA=2:1) indicated the almost completion. Quenched the reaction by TFA to pH around 7, and concentrated in vacuum. The residue was diluted with EA (20 mL), washed with water (10 mL×2), brine (10 mL). The aqueous phase was extracted with EA (10 mL×2). The combined organic phase was dried over Na$_2$SO$_4$, filtered, the filtrate was concentrated to give the crude product of compound 27-C (360 mg) as gum, which was directly use for next step.

Preparation of Compound 27-D

A red suspension of compound 27-C (360 mg, 1 mmol, 1 eq) and DDQ (250 mg, 1.1 mmol, 1.1 eq) in toluene (7 mL) was heated at 50° C. for 1 h. TLC (PE:EA=4:1) indicated the completion. The reaction mixture was directly purified by prep-TLC (PE:EA=2:1) to give the desired product of compound 27-D (100 mg, 28.9%) as colorless gum.

$^1$HNMR: (400 MHz, CHLOROFORM-d) δ: 7.32 (s, 1H), 4.26 (br. s., 1H), 2.75 (s, 3H), 1.98-1.86 (m, 2H), 1.83-1.62 (m, 5H), 1.43 (s, 9H), 1.30 (s, 3H), 1.16 (s, 3H), 1.07 (s, 3H).

LCMS: (M+H-56: 290.9)

Preparation of Compound 27

To a solution of compound 27-D (100 mg, 0.29 mmol, 1 eq) in EA (4 mL) was added 4 M HCl/EA. The resulting mixture was stirred at 10° C. for 4 h. TLC (PE:EA=2:1) indicated reaction completion. The white precipitate was collected by filtration, washed with EA (5 mL). The white solid was then dried in vacuum to give the desired product of compound 27 (65 mg, 79.2%).

$^1$H-NMR: (400 MHz, CD$_3$OD) δ: 7.74 (s, 1H), 3.45 (br. s., 1H), 2.77 (s, 3H), 2.19-2.03 (m, 2H), 2.02-1.93 (m, 2H), 1.92-1.82 (m, 1H), 1.81-1.71 (m, 2H), 1.38 (s, 3H), 1.22 (s, 3H), 1.12 (s, 3H). 2D-NMR: (400 MHz, CD$_3$OD)

HPLC: (purity: 96.45%)

MS: (M+H: 247.1)

Example 27. Synthesis of Compound 28

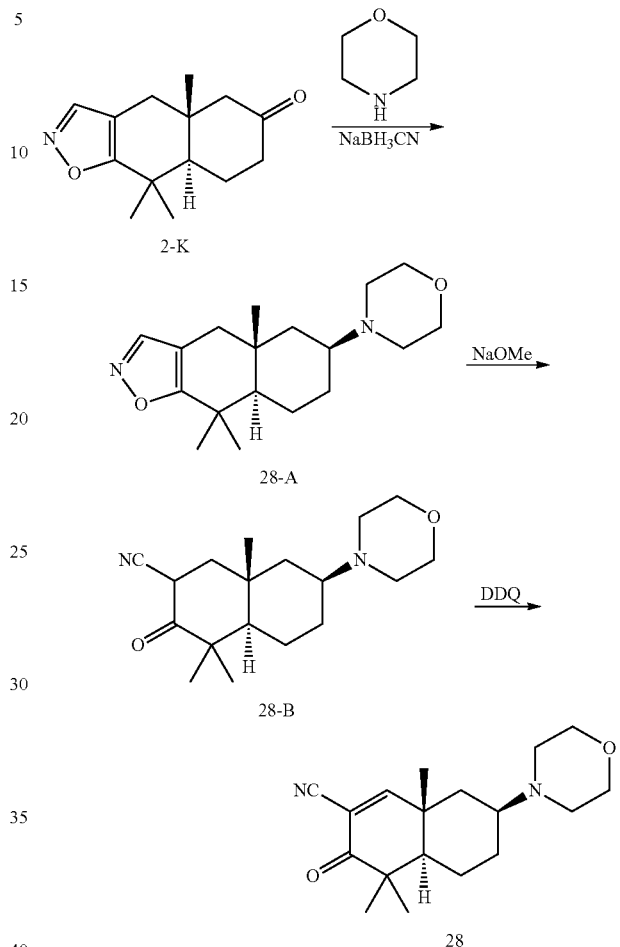

Preparation of Compound 28-A

Compound 2-K (100 mg, 0.43 mmol, 1 eq) and morpholine (75 mg, 0.86 mmol, 2 eq) were added into 2 mL of MeOH/AcOH (v/v=20:1) and stirred at 30° C. for 2 hours. Then NaBH$_3$CN (35 mg, 0.56 mmol, 1.3 eq) was added. The mixture was stirred at 30° C. for 18 hours. TLC (PE:EA=3:1) showed the reaction completed. The mixture was diluted with water (30 mL) and adjusted pH=8 by addition of aq.NaHCO$_3$. The mixture was extracted with EA (25 mL×3). The combined organic phase was dried over Na$_2$SO$_4$, and filtered. The filtrate was concentrated in vacuo to give the residue, which was purified by column chromatography on silica gel (PE:EA=20:1 to 10:1) to give compound 28-A (120 mg, 91%) as colorless solid.

LCMS: (M+H: 305.0).

Preparation of Compound 28-B

To a solution of compound 28-A (120 mg, 0.39 mmol, 1 eq) in MeOH (5 mL) was added a solution of NaOMe in MeOH (1.6 mL, 3.2 mmol, 2 M, 8 eq). The mixture was stirred at 18° C. for 16 hours. The mixture turned to clear. TLC (PE:EA=3:1) showed the reaction completed. Most of the starting material was consumed (R$_f$=0.5) and a new spot was detected (R$_f$=0.2). The mixture was quenched with aq.NH$_4$Cl (10 mL), and extracted with EA (25 mL×3). The combined organic phase was dried over Na$_2$SO$_4$, and filtered. The filtrate was concentrated in vacuo to give the compound 28-B (130 mg, crude), which was used directly in the next step without purification.

Preparation of Compound 28

To a solution of compound 28-B (130 mg, 0.43 mmol, 1 eq) in toluene (5 mL) was added DDQ (107 mg, 0.47 mmol, 1.1 eq). The mixture was stirred at 60° C. for 2 hours. The mixture turned to a black-brown suspension. TLC (PE: EA=1:1) showed the reaction completed. Most of the starting material was consumed ($R_f$=0.3) and a new spot was detected ($R_f$=0.2). The mixture was concentrated in vacuo to give the residue, which was purified by prep-TLC (PE: EA=1:1) to give compound 28 (7.1 mg, 5.5%) as blue-dark oil.

$^1$HNMR: (400 MHz, CDCl$_3$) δ: 7.38 (s, 1H), 3.66 (m, 4H), 2.50-2.30 (m, 5H), 2.22-2.14 (m, 1H), 2.01-1.94 (m, 1H), 1.77-1.71 (m, 1H), 1.64-1.56 (m, 1H), 1.42 (m, 4H), 1.38-1.27 (m, 2H), 1.14 (s, 3H), 1.07 (s, 3H).

HPLC: (Purity: 94.6%).

LCMS: (M+H: 303.2)

Example 28. Synthesis of Compound 29

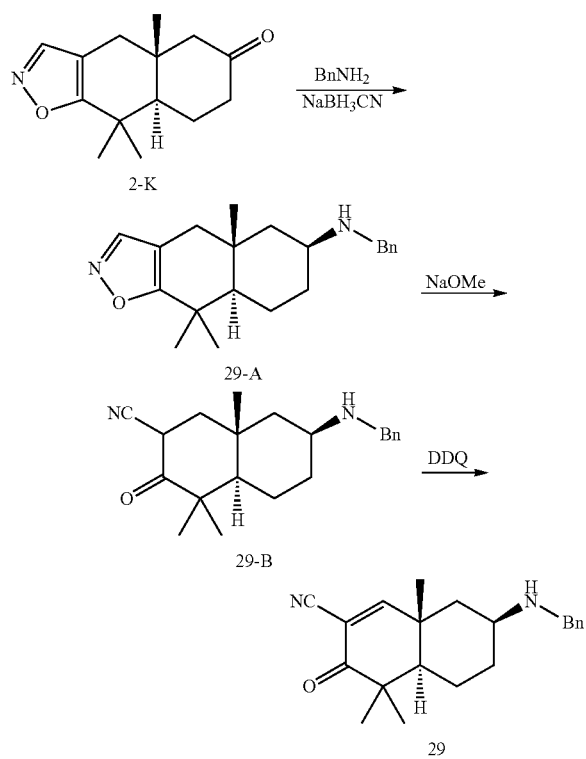

Preparation of Compound 29-A

Compound 2-K (300 mg, 1.28 mmol, 1.0 eq) and phenylmethanamine (276 mg, 2.57 mmol, 2.0 eq) were added into the 10 mL of MeOH/AcOH (V:V=10:1), and the mixture was stirred at 30° C. for 1.5 h. Compound NaBH$_3$CN (106 mg, 1.67 mmol, 1.3 eq) was added and the mixture was stirred at 30° C. for 20 h. TLC (PE/EA=2:1) showed compound 2-K was consumed completely. The desired product was detected by LCMS. The mixture was concentrated to remove the solvent. The residue was diluted with water (30 mL), extracted with EtOAc (15 mL×3). The combined organic layer was dried over anhydrous Na$_2$SO$_4$, filtered, concentrated under reduced pressure to supply crude compound 29-A (400 mg) as colorless gum.

LCMS: 19257-10-3 (M+H: 325.21)

Preparation of Compound 29-B

To a suspension of compound 29-A (400 mg, 1.23 mmol, 1.0 eq) in 5 mL of anhydrous methanol was added NaOMe (2.46 mL, 4.94 mmol, 4.0 eq, 2 M in methanol). The mixture was stirred at 30° C. for 20 h. TLC (PE/EA=3:1) showed a one new spot. The mixture was diluted with water (30 mL), concentrated under reduced pressure to remove methanol, extracted with EtOAc (20 mL×3). The combined organic layer was washed with brine (10 mL), dried over anhydrous Na$_2$SO$_4$, filtered, concentrated under reduced pressure to supply crude compound 29-B (300 mg) as pale-yellow solid.

Preparation of Compound 29

To the solution of compound 29-B (240 mg, 0.74 mmol, 1.0 eq) in 8 mL of anhydrous toluene/DMSO (V:V=3:1) was added DDQ (168 mg, 0.74 mmol, 1.0 eq). The mixture was stirred at 65° C. for 2 h. TLC (PE/EA=2:1) showed compound 29-B was consumed completely. The mixture was diluted with water (30 mL), extracted with EtOAc (20 mL×3).

The combined organic layer was concentrated. The residue was purified by column chromatography on silica gel (PE/EtOAc=10:1-6:1-2:1) and re-purified by prep-TLC (PE/EA=2:1) for two times to supply compound 29 (10.5 mg, 4.4% yield) as pale-yellow gum.

HPLC: (Purity: 95.75%)

SFC: (Purity: 100%)

MS: (M+H: 323.21)

$^1$HNMR: (400 MHz, MeOD) δ: 7.72 (s, 1H), 7.37-7.27 (m, 4H), 7.25-7.19 (m, 1H), 3.83-3.70 (m, 2H), 3.06 (br. s., 1H), 2.02-1.79 (m, 4H), 1.63-1.49 (m, 6H), 1.19 (s, 3H), 1.12 (s, 3H).

Example 29. Synthesis of Compound 30

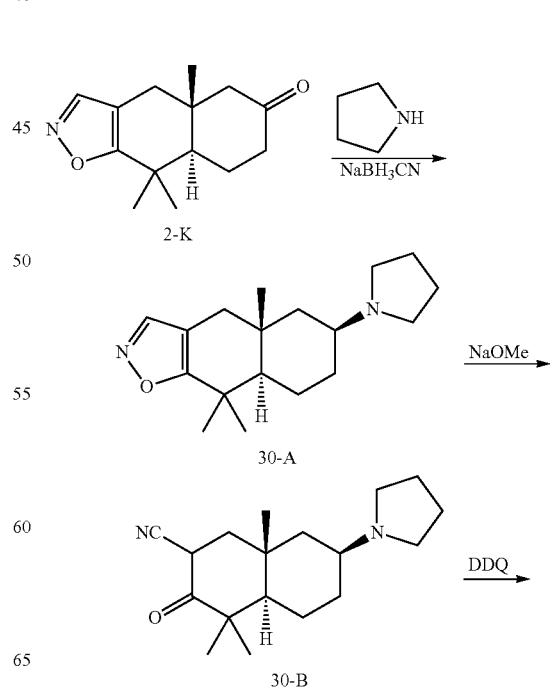

79 80

-continued

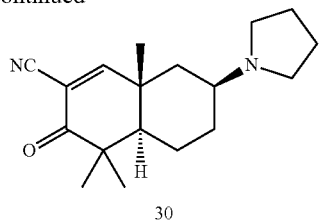

30

Preparation of Compound 30-A

To a solution of compound 2-K (300 mg, 1.28 mmol, 1 eq) in MeOH (4 mL) and AcOH (0.2 mL) was added pyrrolidine (182 mg, 2.57 mmol, 2 eq). After stirring at 20° C. for 1 hour, NaBH$_3$CN (106 mg, 1.7 mmol, 1.3 eq) was added. The mixture was stirred at 20° C. for 16 hours. TLC (PE:EA=3:1) showed the reaction was completed. Most of the starting material was consumed (Rf=0.5) and a new spot was detected (Rf=0.2). The mixture was quenched with aq.NaHCO$_3$ until pH=8, and extracted with EA (25 mL×3). The combined organic phase was dried over Na$_2$SO$_4$, and filtered. The filtrate was concentrated in vacuo to give the residue, which was purified by column chromatography on silica gel to give compound 30-A (320 mg, crude) as colorless oil.

LCMS: (M+H: 289.0)

Preparation of Compound 30-B

To a solution of compound 30-A (320 mg, 1.11 mmol, 1 eq) in MeOH (3 mL) was added a solution of NaOMe in MeOH (1.8 M, 3.1 mL, 5.55 mmol, 5 eq). The mixture was stirred at 20° C. for 16 hours. TLC (DCM:MeOH=20:1) showed the reaction completed. Most of the starting material was consumed (Rf=0.5) and a new spot was detected (Rf=0.45). The mixture was quenched with aq.NH$_4$Cl until pH=7, and extracted with EA (25 mL×3). The combined organic phase was dried over Na$_2$SO$_4$, and filtered. The filtrate was concentrated in vacuo to give the compound 30-B (328 mg, crude), which was used directly in the next step without purification.

Preparation of Compound 30

To a solution of compound 30-B (300 mg, 1.04 mmol, 1 eq) in MeCN (5 mL) was added DDQ (236 mg, 1.04 mmol, 1 eq). The mixture was stirred at 60° C. for 2 hours. The mixture turned to a black-brown suspension. TLC (DCM:MeOH=20:1) showed the reaction completed. Most of the starting material was consumed (Rf=0.45) and a new spot was detected (Rf=0.75). The mixture was concentrated in vacuo to give the residue, which was purified by column chromatography on silica gel (PE:EA=1:1) and further purified by prep-TLC (DCM:MeOH=20:1) to give 30 (17.1 mg, 5.7%) as a pale-yellow solid.

$^1$HNMR: (400 MHz, CDCl$_3$) δ: 7.38 (s, 1H), 2.49-2.37 (m, 4H), 2.35-2.28 (m, 1H), 2.12-2.04 (m, 2H), 1.93-1.84 (m, 1H), 1.68 (m, 5H), 1.48-1.30 (m, 6H), 1.13 (s, 3H), 1.07 (s, 3H).

HPLC: (Purity: 96.2%).

SFC: (purity: 98.91%).

LCMS: (M+H: 286.9).

Example 30. Synthesis of Compound 31

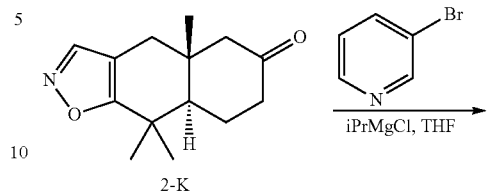

2-K

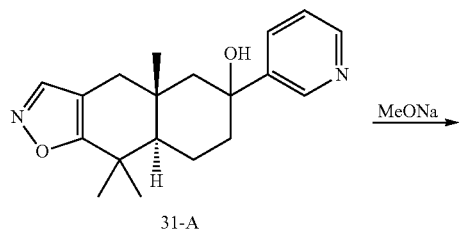

31-A

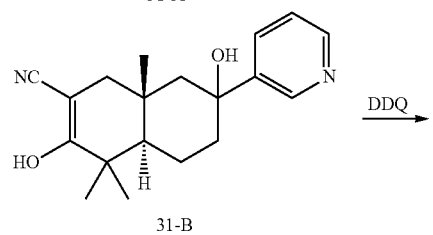

31-B

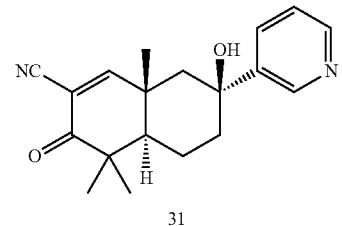

31

Preparation of Compound 31-A

To a solution of compound 3-bromopyridine (2.71 g, 17 mmol, 10 eq) in THF (5 mL) was added i-PrMgCl (8.5 mL, 17 mmol, 2M, 10 eq) dropwise at 0° C. and stirred at 22° C. for 2 h. The resulting mixture was added to a solution of compound 2-K (400 mg, 1.71 mmol, 1 eq) in THF (10 mL) and the mixture was stirred at 22° C. for 18 hours. TLC (PE/EtOAc=1:5) showed the starting materials was consumed completely. The mixture was quenched with NH$_4$Cl (20 mL) and extracted with EA (15 mL×2). The combined organic phase was dried over sodium sulfate, and filtered. The filtrate was concentrated in vacuo to give the residue, which was purified by silica gel chromatography eluted with PE/EtOAc=5:1-1:5) to give compound 31-A (270 mg, 65%) as an off-white solid. This reaction mainly gave one isomer and it was identified at the final step.

$^1$HNMR: (400 MHz, CDCl$_3$) δ: 8.79 (s, 1H), 8.49 (d, J=3.5 Hz, 1H), 8.03 (s, 1H), 7.84 (d, J=7.8 Hz, 1H), 7.33-7.29 (m, 1H), 2.33-2.25 (m, 1H), 2.21-2.15 (m, 1H), 1.97-1.91 (m, 2H), 1.78-1.71 (m, 2H), 1.61-1.48 (m, 2H), 1.36 (s, 3H), 1.26 (s, 3H), 1.20 (s, 3H).

Preparation of Compound 31-B

To a solution of compound 31-A (270 mg, 0.86 mmol, 1 eq) in MeOH (12 mL) was added NaOMe in MeOH (1.73 mL, 3.46 mmol, 2M, 4 eq). The mixture was stirred at 21° C. for 18 hours. TLC (PE/EtOAc=1:5) showed the starting materials was consumed completely. The mixture was concentrated in vacuo to give the residue. The residue was taken up in water (15 mL) and extracted with EA (15 mL×3). The combined organic phase was dried over sodium sulfate and filtered. The filtrate was concentrated in vacuo to give compound 31-B (280 mg, crude), which was used directly in next step without purification.

Preparation of Compound 31

To a solution of compound 31-B (270 mg, 0.86 mmol, crude) in toluene (5 mL) was added DDQ (196 mg, 0.86 mmol, 1.0 eq). The mixture was stirred at 100° C. for 1 hour. TLC (PE:EA=1:1) showed the starting material was consumed completely. The mixture was concentrated in vacuo to give the residue. The residue was purified by column chromatography on silica gel (PE:EA=4:1) to give compound 31 (170 mg, purity: 50%) as a white solid. 50 mg of the obtained product was re-purified by prep-HPLC (Phenomenex Synergi C18 150*30 mm*4 um 0.05% HCl-ACN as mobile phase, from 3-23%, Flow Rate (ml/min): 25) to give compound 31 (8.2 mg, yield: 21%) as a white solid.

$^1$HNMR: (400 MHz, MeOD) δ: 8.98 (s, 1H), 8.76 (d, J=6.6 Hz, 2H), 8.05 (t, J=6.6 Hz, 1H), 7.75 (s, 1H), 2.11-1.97 (m, 5H), 1.92 (m, 1H), 1.77 (d, J=11.0 Hz, 1H), 1.55 (s, 3H), 1.27 (s, 3H), 1.18 (s, 3H).

HPLC: (Purity: 95.48%).

LCMS: (M+H: 310.9).

Example 31. Synthesis of Compound 32

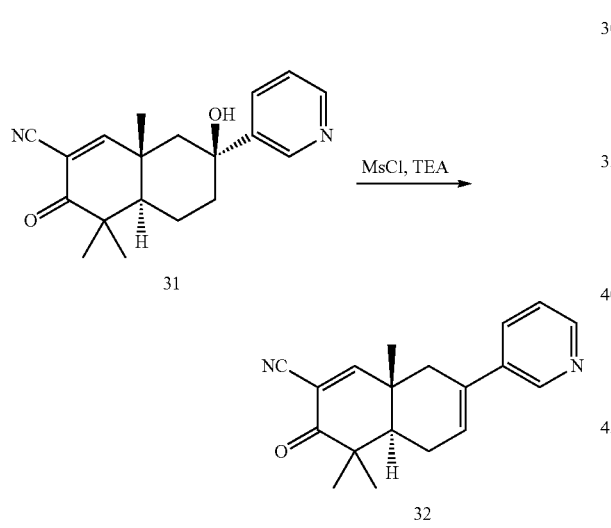

To a solution of compound 31 (80 mg, 0.26 mmol, 1.0 eq) and TEA (103 mg, 1.03 mmol, 4.0 eq) in DCM (5 mL) was added MsCl (65 mg, 0.52 mmol, 2.0 eq) at 0° C. The mixture was stirred at 15° C. for 2 hours. LCMS showed the starting material was consumed completely. The mixture was concentrated in vacuo to give the residue, which was purified by prep-HPLC (Phenomenex Synergi C18 150*30 mm*4 um 0.05% HCl-ACN as mobile phase, from 8-23%, Flow Rate: 25 mL/min) to give compound 32 (3 mg, yield: 3.5%) as a white solid.

$^1$HNMR: (400 MHz, MeOD) δ: 8.91 (s, 1H), 8.76-8.68 (m, 2H), 8.06 (dd, J=8.1, 5.8 Hz, 1H), 7.79 (s, 1H), 6.66 (br. s, 1H), 2.70 (m, 1H), 2.48 (m, 3H), 2.24 (m, 1H), 1.32 (s, 3H), 1.24 (s, 3H), 1.17 (s, 3H).

HPLC: (Purity: 100%).

LCMS: (M+H: 292.9).

Example 32. Synthesis of Compound 33

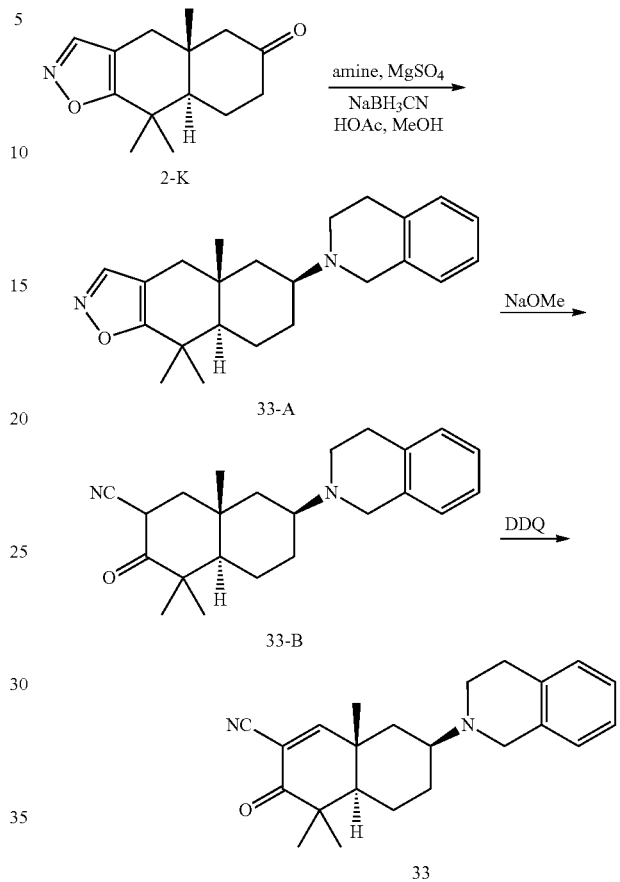

Preparation of Compound 33-A

A suspension of compound 2-K (233 mg, 1 mmol, 1 eq), 1,2,3,4-Tetrahydroisoquinoline (266 mg, 2 mmol, 2 eq), MgSO$_4$ (600 mg, 5 mmol, 5 eq) and HOAc (180 mg, 3 mmol, 3 eq) in MeOH (8 mL) was stirred at 30° C. for 2 h. NaBH$_3$CN (126 mg, 2 mmol, 2 eq) was added to the mixture, and stirred at 30° C. for 18 h. TLC (PE:EA=2:1) indicated the completion. The reaction mixture was concentrated, the residue was diluted with EA (50 mL), washed with saturated NaHCO$_3$ (20 mL×3). The organic phase was dried over Na$_2$SO$_4$, filtered, the filtrate was concentrated to give the crude product which was purified by column chromatography on silica gel eluted with PE:EA=8:1 to give the desired product of compound 33-A (200 mg, 57.1%) as solid.

$^1$H-NMR: (400 MHz, CD$_3$OD) δ: 7.94 (s, 1H), 7.13-6.96 (m, 4H), 3.85 (d, J=14.5 Hz, 1H), 3.42 (d, J=14.5 Hz, 1H), 3.04 (br. s., 1H), 2.87 (d, J=10.2 Hz, 1H), 2.78-2.66 (m, 1H), 2.47-2.28 (m, 3H), 2.23-2.04 (m, 4H), 1.69-1.56 (m, 1H), 1.53-1.29 (m, 4H), 1.25 (s, 3H), 1.09 (d, J=13.7 Hz, 6H).

Preparation of Compound 33-B

To a solution of compound 33-A (200 mg, 0.57 mmol, 1 eq) in MeOH (8 mL) was added MeONa (123.1 mg, 2.28 mmol, 4 eq). The resulting mixture was stirred at 5-10° C. for 2 days (about 42 h). TLC (PE:EA=4:1) indicated the almost completion. Quenched the reaction by HOAc (137 mg, 2.28 mmol, 4 eq). The reaction mixture was concentrated in vacuum to give the residue. The residue was diluted with EA (20 mL), washed with water (20 mL). The aqueous phase was extracted with EA (10 mL×3). The combined organic phase was dried over Na$_2$SO$_4$, filtered, the filtrate was concentrated to give the crude product of compound 33-B (203 mg) as solid, which was directly use for next step.

Preparation of Compound 33

A suspension of compound 33-B (203 mg crude, 0.57 mmol, 1 eq) and DDQ (136 mg, 0.6 mmol, 1.05 eq) in MeCN (6 mL) was heated at 60° C. for 1 h. TLC (PE:EA=4:1) indicated the same spot. The LCMS indicated the completion. The reaction mixture was concentrated in vacuum to give the residue, which was diluted with EA (30 mL). Washed with saturated aqueous Na$_2$CO$_3$. The aqueous phase was extracted with DCM (10 mL×2). The combined organic phase was dried over Na$_2$SO$_4$, filtered, the filtrate was concentrated and the residue was purified y pre-TLC (PE:EA=3:1) to give the desired product (60 mg, 30% yield, purity on SFC is only 90%) as solid. This product was further purified by SFC (column: AD 250 mm×30 mm, 5 um; condition: 25% EtOH in CO$_2$; flow rate: 70 mL/min) to give the pure product of compound 33 (38 mg, Rt=2.89 min, yield: 19%) as solid.

$^1$H-NMR: (400 MHz, CD$_3$CN) δ: 7.70 (s, 1H), 7.23-7.02 (m, 4H), 3.87 (d, J=15.0 Hz, 1H), 3.53 (d, J=15.0 Hz, 1H), 3.11-3.00 (m, 1H), 2.95-2.79 (m, 2H), 2.61-2.50 (m, 2H), 2.41 (d, J=14.3 Hz, 1H), 2.28 (br. s., 1H), 1.92 (d, J=2.2 Hz, 1H), 1.81-1.67 (m, 1H), 1.59-1.50 (m, 3H), 1.47 (s, 3H), 1.19 (s, 3H), 1.08 (s, 3H). 2D-NMR: (400 MHz, CD$_3$CN).

HPLC: (purity: 100%)
SFC: (purity: 95.12%)
LCMS: (M+H: 349.2)

Example 33. Synthesis of Compound 34

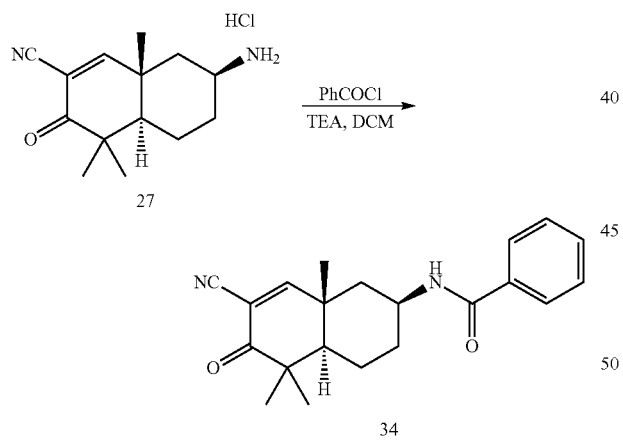

To the mixture of compound 27 (50 mg, 0.22 mmol, 1.0 eq) in 2 mL of anhydrous DCM was added TEA (44 mg, 0.43 mmol, 2.0 eq) and benzoyl chloride (39 mg, 0.28 mmol, 1.3 eq). The mixture was stirred at 6-18° C. for 1 h. TLC (PE:EA=1:1) showed one main spot was observed. The mixture was diluted with DCM (10 mL), washed with water (6 mL×3). The organic phase was concentrated and the residue was purified by prep-TLC (PE:EA=1:1) for two times to supply compound 34 (18.4 mg, 24.9% yield) as white solid.

HPLC: (purity: 98.73%)
SFC: (purity: 99.45%)
LCMS: (M+H: 337.1)

$^1$HNMR: (400 MHz, CDCl$_3$) δ: 7.75 (d, J=7.4 Hz, 1H), 7.58-7.38 (m, 4H), 6.15 (br. s., 1H), 4.42 (br. s., 1H), 2.26 (d, J=14.1 Hz, 1H), 2.08 (d, J=14.1 Hz, 1H), 1.91-1.56 (m, 5H), 1.41 (s, 3H), 1.26 (s, 3H), 1.14 (s, 3H).

Example 34. Synthesis of Compound 35

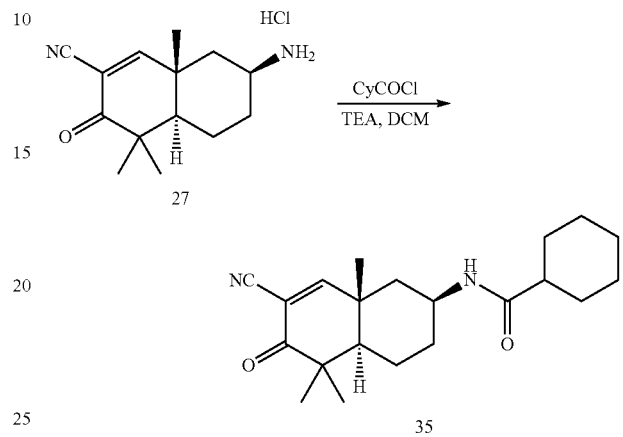

To the mixture of compound 27 (80 mg, 0.34 mmol, 1.0 eq) in 5 mL of anhydrous DCM was added TEA (69 mg, 0.68 mmol, 2.0 eq) and cyclohexanecarbonyl chloride (65 mg, 0.45 mmol, 1.3 eq). The mixture was stirred at 3-13° C. for 1 h. TLC (PE:EA=1:1) showed one main spot was observed. The mixture was diluted with DCM (20 mL), washed with water (10 mL×3). The organic phase was concentrated and the residue was purified by prep-TLC (PE:EA=1:1) for two times to supply compound 35 (45.5 mg, 39.2% yield) as white solid.

HPLC: (purity: 98.83%)
SFC: (purity: 98.86%)
LCMS: (M+H: 343.2)

$^1$HNMR: (400 MHz, CDCl$_3$) δ: 7.43 (s, 1H), 5.44 (d, J=4.7 Hz, 1H), 4.20 (br. s., 1H), 2.19-2.01 (m, 2H), 1.96-1.66 (m, 9H), 1.64-1.58 (m, 2H), 1.49-1.35 (m, 2H), 1.35-1.21 (m, 9H), 1.12 (s, 3H).

Example 35. Synthesis of Compound 36

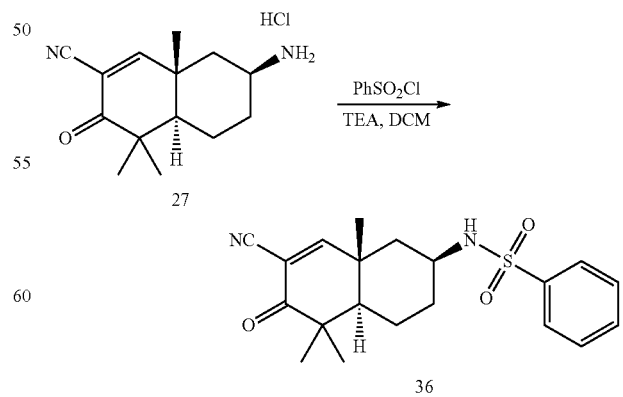

To the mixture of compound 27 (100 mg, 0.43 mmol, 1.0 eq) in 8 mL of anhydrous DCM was added TEA (130 mg, 1.29 mmol, 3.0 eq) and benzenesulfonyl chloride (152 mg, 0.86 mmol, 2.0 eq). The mixture was stirred at 5-16° C. for 18 h. TLC (PE:EA=1:1) showed one main spot was observed. The mixture was diluted with DCM (20 mL), washed with water (10 mL×3). The organic phase was concentrated and the residue was purified by silica gel column chromatography (PE:EA=10:1-6:1) and re-purified by prep-TLC (PE:EA=1:1) to supply compound 36 (14.7 mg, 9.2% yield) as pale-yellow gum.

HPLC: (purity: 97.05%)
SFC: (purity: 96.73%)
MS: (M+H: 373.16)
$^1$HNMR: (400 MHz, CDCl$_3$) δ: 7.90 (d, J=7.4 Hz, 2H), 7.68-7.48 (m, 3H), 7.40 (s, 1H), 4.88 (d, J=3.9 Hz, 1H), 3.52 (br. s., 1H), 1.99 (d, J=14.1 Hz, 1H), 1.83 (d, J=12.9 Hz, 1H), 1.69-1.48 (m, 5H), 1.40 (s, 3H), 1.19 (s, 3H), 1.09 (s, 3H).

Example 36. Synthesis of Compound 37

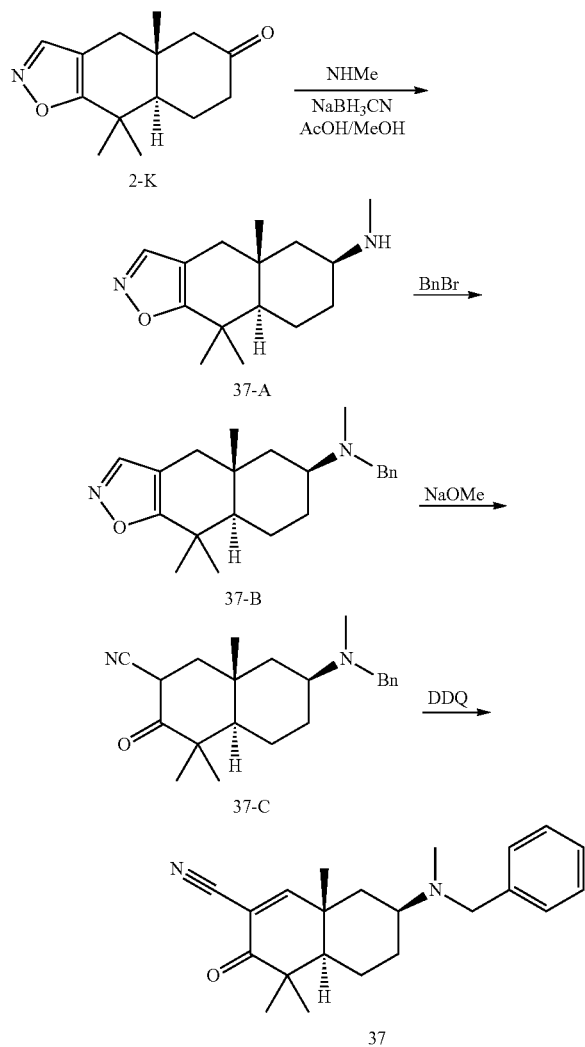

Preparation of Compound 37-A

To a solution of compound 2-K (400 mg, 1.7 mmol, 1.0 eq) in 10 mL of EtOH/AcOH (V:V=20:1) was added methylamine (17 mL, 17 mmol, 10 eq, 1M in THF). After addition the mixture was stirred at 18° C. for 1 h under N$_2$ atmosphere. NaBH$_3$CN (161 mg, 2.55 mmol, 1.5 eq) was added and the mixture was stirred at 18° C. for 2 h. TLC (PE:EA=3:1) showed compound 2-K was consumed completely. LCMS detected the desired product. The mixture was concentrated under reduced pressure to remove the solvent. The residue was diluted with water (15 mL), extracted with EtOAc (10 mL×5). The combined organic layer was concentrated to supply crude compound 37-A (400 mg) as colorless gum.

LCMS: (M+H: 249.2)

Preparation of Compound 37-B

To a solution of compound 37-A (280 mg, 1.13 mmol, 1.0 eq) in 10 mL of DCM was added TEA (341 mg, 3.38 mmol, 3.0 eq) and BnBr (579 mg, 3.38 mmol, 3.0 eq). After addition the mixture was stirred at 3-12° C. for 18 h. TLC (PE:EA=4:1) showed one new spot. The mixture was diluted with DCM (20 mL), washed with water (10 mL×3). The organic layer was concentrated and purified by column chromatography on silica gel (PE:EA=20:1-15:1-10:1) to supply compound 37-B (90 mg, 27% yield) as white solid.

$^1$HNMR: (400 MHz, CDCl$_3$) δ: 8.01 (s, 1H), 7.36-7.20 (m, 5H), 3.68 (d, J=13.7 Hz, 1H), 3.49 (d, J=13.3 Hz, 1H), 2.48-2.31 (m, 2H), 2.20 (m, 3H), 2.11 (s, 3H), 1.82-1.68 (m, 1H), 1.57-1.41 (m, 4H), 1.33 (s, 3H), 1.27 (s, 6H).

Preparation of Compound 37-C

To a mixture of compound 37-B (130 mg, 0.38 mmol, 1.0 eq) in 2 mL of anhydrous methanol was added NaOMe (1.15 mL, 2.3 mmol, 6.0 eq, 2 M in methanol). The mixture was stirred at 5° C.~16° C. for 18 h. TLC (PE:EA=3:1) showed compound 37-B was consumed completely. The mixture was concentrated to remove methanol, the residue was diluted with water (15 mL), adjusted pH to 7 by adding 1M HCl, and then extracted with EtOAc (10 mL×3). The combined organic layer was dried over anhydrous Na$_2$SO$_4$, filtered, concentrated under reduced pressure to supply crude compound 37-C (100 mg) as pale-yellow solid.

Preparation of Compound 37

To a solution of compound 37-C (100 mg, 0.3 mmol, 1.0 eq) in 5 mL of acetonitrile/anhydrous toluene (V:V=3:2) was added DDQ (67 mg, 0.3 mmol, 1.0 eq). The mixture was stirred at 80° C. for 1.5 h. TLC (PE:EA=3:1) showed compound 37-C was consumed completely. The mixture was concentrated under reduced pressure. The residue was diluted with EtOAc (30 mL), washed with saturated aqueous NaHCO$_3$ (15 mL×4). The organic layer was dried over anhydrous Na$_2$SO$_4$, filtered, concentrated under reduced pressure. The residue was purified by prep-TLC (PE:EA=2:1) for two times to supply compound 37 (8.7 mg, 8.7% yield) as pale-yellow gum.

HPLC: (purity: 97.29%)
SFC: (purity: 100%)
LCMS: (M+H: 337.2)
$^1$HNMR: (400 MHz, CDCl$_3$) δ: 7.48 (s, 1H), 7.38-7.22 (m, 5H), 3.67-3.49 (m, 2H), 2.60 (br. s., 1H), 2.35 (m, 1H), 2.17-2.08 (m, 4H), 1.88-1.70 (m, 2H), 1.62-1.45 (m, 6H), 1.23 (s, 3H), 1.17 (s, 3H).

Example 37. Synthesis of Compound 38

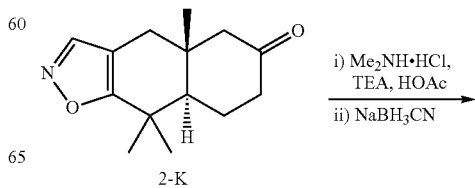

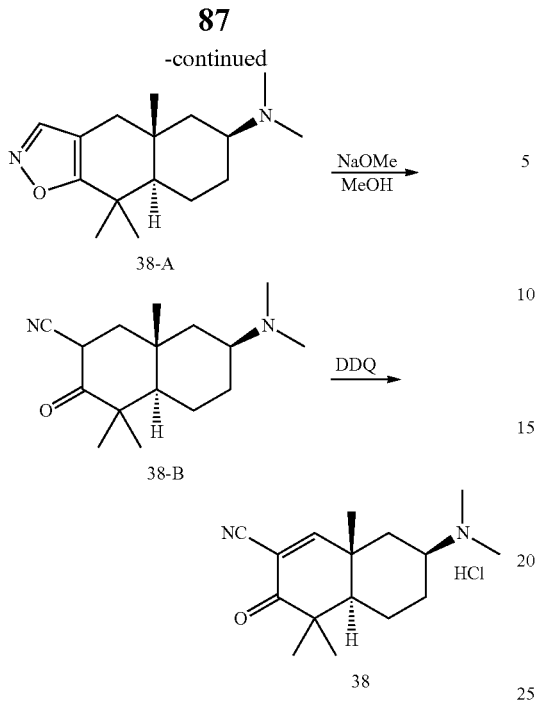

Preparation of Compound 38-A

To a suspension of compound 2-K (233 mg, 1 mmol, 1 eq), and Me₂NH.HCl (489 mg, 6 mmol, 6 eq) in HOAc (0.5 mL) and MeOH (6 mL) was added TEA (505 mg, 5 mmol, 5 eq). The resulting mixture was stirred at 30° C. for 2 h. NaBH₃CN (126 mg, 2 mmol, 2 eq) was added to the mixture, and stirred at 30° C. for 18 h. LCMS indicated the completion. The reaction mixture was concentrated, the residue was diluted with EA (30 mL), washed with saturated NaHCO₃ (20 mL×2). The aqueous phase was extracted with EA (30 mL). The combined organic phase was dried over Na₂SO₄, filtered, and the filtrate was concentrated to give the crude product of compound 38-A (~300 mg) which was directly used for next step.

Preparation of Compound 38-B

To a solution of MeONa (216 mg, 4 mmol, 4 eq) in MeOH (4 mL) was added compound 38-A (300 mg crude, 1 mmol, 1 eq) in MeOH (2 mL). The mixture was stirred at 25° C. for 18 h. LCMS indicated the completion. Quenched the reaction by HOAc (240 mg, 4 mmol, 4 eq).

The reaction mixture was concentrated in vacuum to give the residue. To the residue was added MeCN (6 mL). The mixture was filtered and the filtrate containing compound 38-B was directly used for next step without purification.

Preparation of Compound 38

To a solution of compound 38-B (about 1 mmol, 1 eq) in MeCN (6 mL) was added DDQ (250 mg, 1.1 mmol, 1.1 eq). The mixture was stirred at 60° C. for 1 h. LCMS indicated the completion. The reaction mixture was concentrated in vacuum to give the residue, which was diluted with EA (30 mL). The organic phase was washed with saturated aqueous Na₂CO₃. The aqueous phase was extracted with EA (10 mL×3). The combined organic phase was dried over Na₂SO₄, filtered, the filtrate was concentrated to give the residue (about 250 mg), which was purified prep-HPLC (column: Phenomenex Synergi C18 150*30 mm*4 um; condition: elution A: water with 0.05% HCl; elution B: acetonitrile; flow rate: 25 mL/min) to give the compound 38 (100 mg, yield: 33.7%) as gum.

¹H-NMR: (400 MHz, MeOD) δ: 7.70 (s, 1H), 3.65-3.48 (m, 1H), 2.89 (d, J=3.5 Hz, 6H), 2.11-2.01 (m, 4H), 1.97-1.82 (m, 3H), 1.42 (s, 3H), 1.18 (s, 3H), 1.11 (s, 3H). Note there was 10% diastereomer on H-NMR.

HPLC: (purity: 99.01%)

SFC: (purity: 92.73%)

LCMS: M+H: 261.2)

Example 38. Synthesis of Compound 39

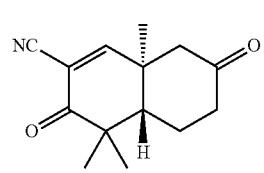

Compound 39 was made in a manner analogous to that already described for compound 5, using (S)-1-phenylethan-1-amine instead of (R)-1-phenylethan-1-amine in the conversion of 2-B to 2-C.

Data for 39:

¹HNMR: (400 MHz, CDCl3) δ: 7.33 (s, 1H), 2.60-2.58 (m, 1H), 2.46-2.30 (m, 4H), 2.23-2.22 (m, 1H), 1.90-1.89 (m, 1H), 1.32 (s, 3H), 1.21 (s, 3H), 1.13 (s, 3H).

HPLC: (Purity: 97.93%)

SFC: (ee: 99.56%) [SFC (column: AD (250 mm*30 mm, 10 μm), condition: 0.1% NH₃H₂O ETOH]

LCMS: (M+H: 232.2).

Example 39. Synthesis of Compound 40

Compound 40 was made in a manner analogous to that already described for compound 24, using (S)-1-phenylethan-1-amine instead of (R)-1-phenylethan-1-amine in the conversion of 2-B to 2-C.

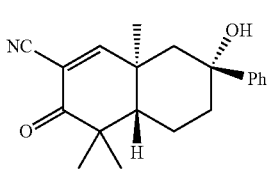

Data for 40:

HPLC: (purity=100%)

LCMS: (M+H=310.0)

SFC: (see value=99.74%) [prep-SFC (Neu-ETOH, OJ (250 mm*30 mm, 5 μm), 60 ml/min)]

¹H-NMR: (400 MHz, DMSO) δ: 7.96 (s, 1H) 1.05 (s, 3H) 1.16 (s, 3H) 1.43 (s, 3H) 1.56 (br d, J=11.8 Hz, 1H) 1.68-1.74 (m, 1H) 1.76-1.91 (m, 4H) 1.98 (br d, J=11.8 Hz, 1H) 3.29 (s, 1H) 4.91 (s, 1H) 7.14-7.21 (m, 1H) 7.28 (t, J=7.6 Hz, 2H) 7.48 (d, J=7.0 Hz, 2H)

Example 40. Synthesis of Compound 41

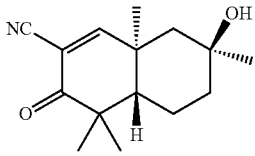

41

Compound 41 was made in a manner analogous to that already described for compound 10, using (S)-1-phenylethan-1-amine instead of (R)-1-phenylethan-1-amine in the conversion of compound 2-B to 2-C.

Data for 41:
HPLC: (Purity: 100%)
SFC: (Rt=2.853 min, purity: 100%). SFC (column: OD 250 mm×30 mm, 5 um; Neu-EtOH)
LCMS: (M+H: 248.2)
$^{1}$H-NMR: (400 MHz, CDCl$_{3}$) δ: 7.48 (s, 1H), 1.91-1.80 (m, 2H), 1.74-1.65 (m, 2H), 1.63-1.56 (m, 1H), 1.51-1.47 (m, 2H), 1.45 (s, 3H), 1.29 (s, 3H), 1.24 (s, 3H), 1.15 (s, 3H), 1.09 (br, 1H)

Example 41. Synthesis of Compound 42

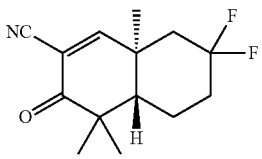

42

Compound 42 was made in a manner analogous to that already described for compound 2, using (S)-1-phenylethan-1-amine instead of (R)-1-phenylethan-1-amine in the conversion of 2-B to 2-C.

prep-SFC conditions: (0.1% NH$_{3}$H$_{2}$O ETOH, AD (250 mm*30 mm, 10 um) 50 ml/min)
$^{1}$HNMR: (400 MHz, CDCl$_{3}$) δ: 7.44 (s, 1H), 2.33 (s, 1H), 2.06-2.18 (m, 1H), 1.70-1.91 (m, 6H), 1.32 (d, J=3.2 Hz, 4H), 1.13 (s, 3H), 1.26 (s, 3H).
HPLC: (Purity: 100%).
SFC: (ee value: 98.3%)
LCMS: (M+H: 254.1).

Example 42. Synthesis of Compound 43

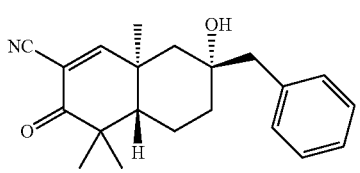

43

Compound 43 was made in a manner analogous to that already described for compound 19, using (S)-1-phenylethan-1-amine instead of (R)-1-phenylethan-1-amine in the conversion of 2-B to 2-C.

Prep SFC conditions (0.1% NH$_{3}$H$_{2}$O/ETOH, AD (250 mm*30 mm, 10 um) 60 ml/min)
$^{1}$HNMR: (400 MHz, DMSO) δ: 7.91 (s, 1H), 7.14-7.26 (m, 5H), 4.26 (s, 1H), 2.61 (s, 2H), 1.52-1.68 (m, 4H), 1.31-1.46 (m, 3H), 1.29 (s, 3H), 1.08 (s, 3H), 0.98 (s, 3H).
HPLC: (purity: 99.07%)
LCMS: (M+H: 324.0)
SFC: (ee value: 99.69%)

Example 43. Synthesis of Compound 44

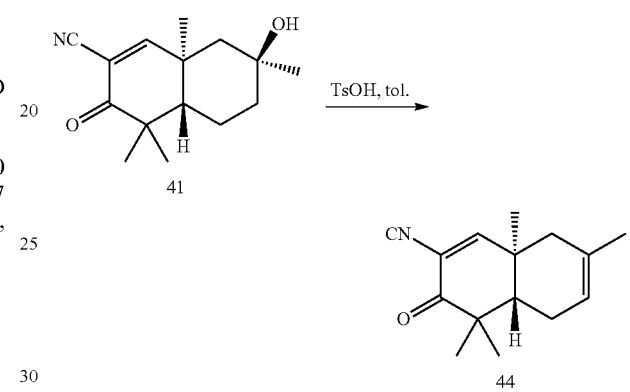

To a solution of compound 41 (50 mg, 0.20 mmol, 1.0 eq) in toluene (3 mL) was added TsOH (19 mg, 0.10 mmol, 0.5 eq). The reaction mixture was stirred at 110° C. for 2 h. TLC (PE/EA=3:1) showed the compound 41 was consumed completely. The mixture was concentrated and purified by prep-TLC (PE:EA=3:1) to give compound 44 (50 mg, 72.5% yield) as a white solid. The compound 44 was further purified by SFC (Column: AD (250 mm*30 mm, 10 um); Condition: Neu-EtOH) to give 44 (Rt=2.132 min, 20 mg, 40% yield) as a white solid.

$^{1}$HNMR: (400 MHz, CDCl$_{3}$) δ: 7.40 (s, 1H), 5.48 (br s, 1H), 2.19-2.01 (m, 3H), 1.96-1.90 (m, 1H), 1.76 (d, J=15.9 Hz, 1H), 1.69 (s, 3H), 1.20 (d, J=4.4 Hz, 6H), 1.11 (s, 3H)
HPLC: Purity: 98.92%)
SFC: (purity: 96.43%)
LCMS: (M+H: 230.1)

Example 44. Synthesis of Compound 45

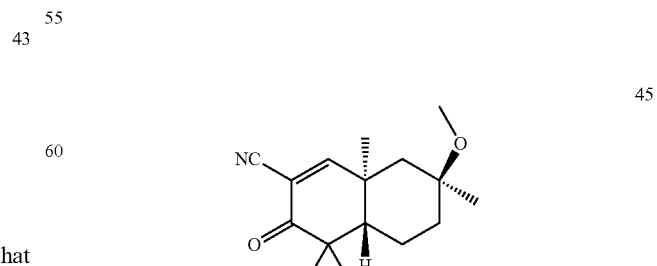

45

Compound 45 was made in a manner analogous to that already described for compound 18, using (S)-1-phenylethan-1-amine instead of (R)-1-phenylethan-1-amine in the conversion of 2-B to 2-C.

Data for 45: (pending from WuXi)

Example 45. Synthesis of Compound 46

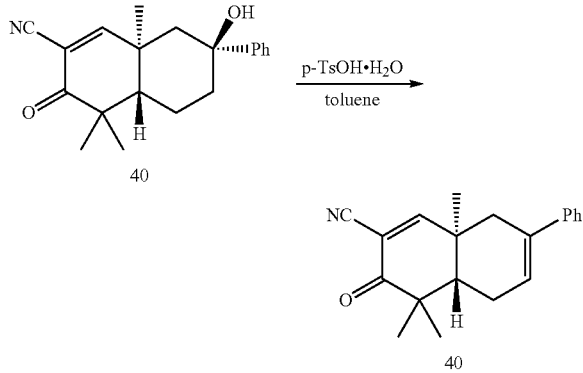

To the solution of compound 40 (350 mg, 1.13 mmol, 1.0 eq) in 20 mL of toluene was added p-TsOH.H$_2$O (108.3 mg, 0.57 mmol, 0.5 eq) was refluxed for 2 h. TLC (PE/EA=5:1, Rf=0.5) showed compound 40 was consumed completely. The reaction mixture was filtered and the filtrate was concentrated to get the residue which was purified by prep-TLC (PE:EA=5:1) to supply the crude compound 46 (150 mg). The crude compound 46 was re-purified by prep-HPLC (water (0.05% HCl)-CAN, Phenomenex Synergi C18 150*30 mm*4 um, from 55%-75%, FlowRate (mL/min) 25) to give compound 46 (100 mg, crude), which was further purified by prep-SFC (Neu-ETOH, OD (250 mm*30 mm, 5 um), 50 mL/min) to supply compound 46 (83 mg) as white solid.

$^1$H-NMR: (400 MHz, CDCl$_3$) δ: 7.50 (s, 1H), 7.32-7.37 (m, 4H), 7.27-7.31 (m, 1H), 6.13-6.18 (m, 1H), 2.55-2.59 (m, 1H), 2.23-2.42 (m, 3H), 2.11 (dd, J=11.8, 5.2 Hz, 1H), 1.29 (s, 3H). 1.25 (s, 3H). 1.16 (s, 3H).

Example 46. Synthesis of Compound 47

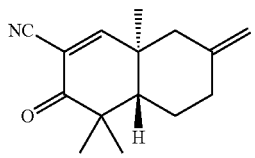

Compound 47 was made in a manner analogous to that already described for compound 9, using (S)-1-phenylethan-1-amine instead of (R)-1-phenylethan-1-amine in the conversion of 2-B to 2-C.

$^1$HNMR: (400 MHz, CHLOROFORM-d) δ: 7.42 (s, 1H), 4.92-4.85 (m, 1H), 4.75 (m, 1H), 2.50 (m, 1H), 2.23-2.16 (m, 1H), 2.13-2.08 (m, 2H), 1.88 (dd, J=2.8, 12.8 Hz, 1H), 1.76 (m, 1H), 1.54-1.47 (m, 1H), 1.24 (s, 3H), 1.14 (s, 3H), 1.08 (s, 3H)

HPLC: (purity 100%)
SFC: (purity: 97.49%)
LCMS: (M+H: 230.2)

Example 47. Synthesis of Compound 48

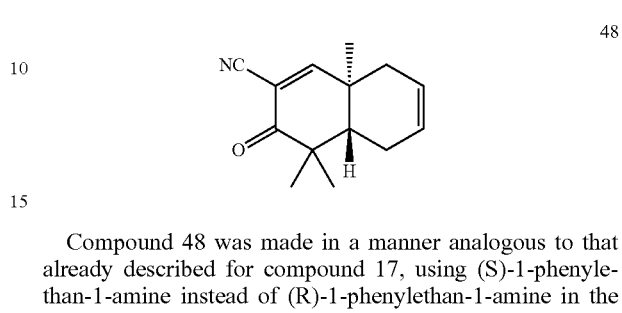

Compound 48 was made in a manner analogous to that already described for compound 17, using (S)-1-phenylethan-1-amine instead of (R)-1-phenylethan-1-amine in the conversion of 2-B to 2-C.

Data for 48: (Pending from WuXi)

Example 48. Synthesis of Compound 49

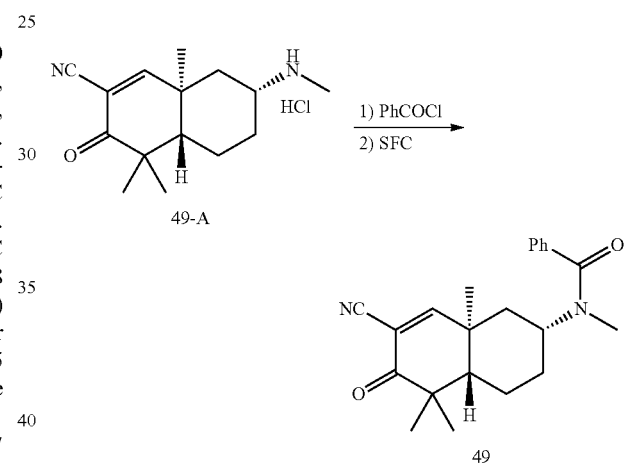

Compound 49-A was made in a manner analogous to that already described for compound 27, using (S)-1-phenylethan-1-amine instead of (R)-1-phenylethan-1-amine in the conversion of 2-B to 2-C.

To the mixture of compound 49-A (100 mg, 0.35 mmol, 1.0 eq) and TEA (106 mg, 1.05 mmol, 3.0 eq) in 5 mL of anhydrous DCM was added benzoyl chloride (64 mg, 0.46 mmol, 1.3 eq). The mixture was stirred at 10-13° C. for 3 h. TLC (DCM:MeOH=20:1) showed compound 49-A remained, one new spot was observed. Additional TEA (106 mg, 1.05 mmol, 3.0 eq) and additional benzoyl chloride (64 mg, 0.46 mmol, 1.3 eq) were added. The resulting mixture was stirred at 10-13° C. for 18 h. TLC (PE:EA=1:3) was used to visualize the reaction. The mixture was diluted with DCM (20 mL), washed with water (10 mL×3). The organic layer was dried over anhydrous Na2SO4, filtered, concentrated under reduced pressure and purified by prep-TLC (PE:EA=1:3) to supply compound 49 (120 mg, 80.75% yield) as colorless gum. Compound 49 was further purified by SFC (column: OJ 250 mm*30 mm, 5 um, condition: NEU-EtOH) to give 49 (Rt=4.718 min, 86 mg, 57.8% yield) as white solid.

HPLC: (purity: 99.32%)

SFC: (Rt: 4.718 min, purity: 100%)

LCMS: (M+H: 351.1)

1HNMR: (400 MHz, CDCl3) δ: 7.44-7.32 (m, 6H), 4.62 (br s, 1H), 4.85-4.38 (m, 1H), 2.92 (s, 3H), 2.15-1.71 (m, 7H), 1.41 (s, 3H), 1.17 (br s, 3H), 1.10 (s, 3H).

Example 49. Synthesis of Compound 50

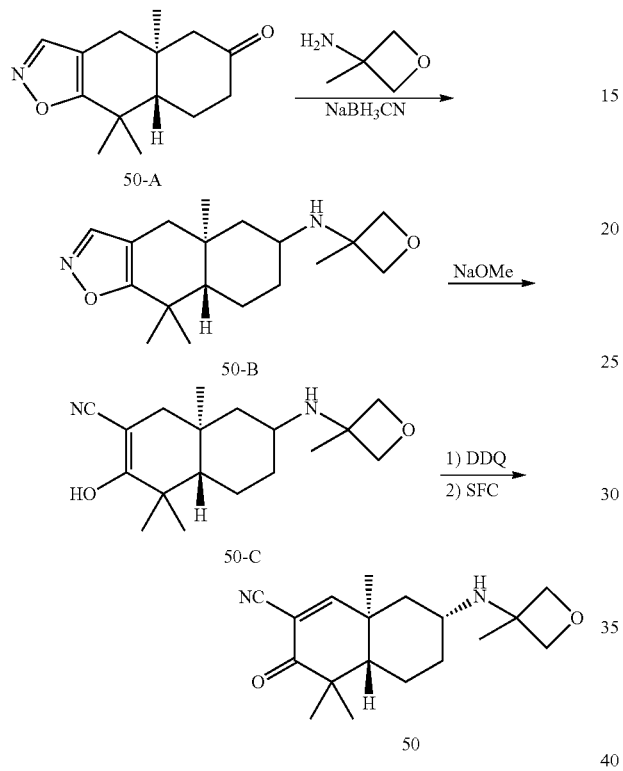

Compound 50-A was made in a manner analogous to that already described for compound 2-K, using (S)-1-phenylethan-1-amine instead of (R)-1-phenylethan-1-amine in the conversion of 2-B to 2-C.

Preparation of Compound 50-B

Compound 50-A (350 mg, 1.50 mmol, 1.0 eq), 3-methyloxetan-3-amine (223 mg, 3.0 mmol, 2.0 eq) and AcOH (180 mg, 3.0 mmol, 2.0 eq) were added into the 5 mL of MeOH, and the mixture was stirred at 80° C. for 18 h. NaBH$_3$CN (123 mg, 1.95 mmol, 1.3 eq) was added under ice-bath cooling, and the resulting mixture was stirred at 50° C. for 4 h. TLC (PE:EA=1:1) showed one new spot. The mixture was concentrated to remove the solvent. The residue was diluted with water (20 mL), adjusted to pH~10, extracted with EtOAc (15 mL×4). The combined organic layers were washed with brine (20 mL), dried over anhydrous Na$_2$SO$_4$, filtered, concentrated and purified by column chromatography on silica gel (PE:EA=8:1~1:1) to supply crude compound 50-B (270 mg, 59.2% yield) as off-white gum.

$^1$HNMR: (400 MHz, CDCl$_3$) δ: 8.00 (s, 1H), 4.53 (m, 2H), 4.41 (m, 2H), 3.11 (m, 1H), 2.28-2.22 (m, 1H), 2.16-2.10 (m, 1H), 1.69-1.61 (m, 4H), 1.60-1.51 (m, 2H), 1.49 (s, 3H), 1.46-1.41 (m, 1H), 1.32-1.31 (m, 3H), 1.22 (s, 3H), 1.10 (s, 3H).

Preparation of Compound 50-C

To a solution of compound 50-B (270 mg, 0.89 mmol, 1.0 eq) in 5 mL of methanol was added NaOMe (2.66 mL, 5.32 mmol, 6.0 eq, 2M in methanol). The mixture was stirred at 20-23° C. for 18 h. TLC (PE:EA=1:1) showed compound 50-B was consumed completely. The mixture was concentrated to remove methanol, the residue was diluted with water (15 mL), extracted with DCM/MeOH (v:v=15:1, 15 mL×10). TLC (PE:EA=1:2) showed the aqueous layer contained the desired product. The aqueous phase was concentrated under reduced pressure. The solid was stirred with EA/MeCN (v:v=2:1, 50 mL×2), filtered. The filtrates and extracts were combined together and dried over anhydrous Na$_2$SO$_4$, filtered, concentrated under reduced pressure to supply crude compound 50-C (240 mg) as pale-yellow gum.

Preparation of Compound 50

Compound 50-C (240 mg, 0.79 mmol, 1.0 eq) and DDQ (197 mg, 0.86 mmol, 1.1 eq) were added into anhydrous toluene/MeCN (5 mL/2 mL). The mixture was stirred at 90° C. for 1.5 h.

TLC (PE:EA=1:4) showed compound 50-C was consumed completely. The mixture was concentrated and purified by prep-TLC (DCM:MeOH=20:1) twice to supply compound 50 (70 mg, 29.4% yield) as a white solid with ee value of 81.48%, which was further purified by SFC (column: AD 250 mm*30 mm, 5 um, condition: 0.1% NH$_3$.H$_2$O-MeOH) to give compound 50 (Rt=6.346 min, 44 mg, 16.9% yield) as white solid.

HPLC: (Purity: 98.01%)

SFC: Purity: 99.39%)

MS: (M+H: 303.2)

$^1$HNMR: (400 MHz, MeOD) δ: 7.93 (s, 1H), 4.42 (m, 2H), 4.17 (m, 2H), 3.05 (br s, 1H), 2.08 (br d, J=5.3 Hz, 1H), 1.77-1.66 (m, 2H), 1.65-1.53 (m, 3H), 1.50-1.36 (m, 8H), 1.11 (s, 3H), 1.03 (s, 3H).

Example 50. Synthesis of Compound 51

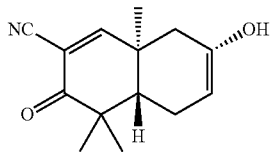

Compound 51 was made in a manner analogous to that already described for compound 3, using (S)-1-phenylethan-1-amine instead of (R)-1-phenylethan-1-amine in the conversion of 2-B to 2-C.

Data for 51:

$^1$H NMR: 19327-87-1A (400 MHz, CDCl$_3$) δ: 7.47 (s, 1H), 4.27 (br, 1H), 2.02-1.94 (m, 1H), 1.90-1.80 (m, 2H), 1.73 (dd, J=2.0, 12.6 Hz, 1H), 1.65-1.58 (m, 3H), 1.46 (s, 3H), 1.38 (d, J=2.2 Hz, 1H), 1.23 (s, 3H), 1.15 (s, 3H)

HPLC: 19327-87-1B (Purity: 99.72%)

LCMS: 19327-87-1A (M+H: 234.2)

SFC: 19327-87-1A_E1 (Rt=3.286 min, Purity: 98.5%)

Example 51. Synthesis of Compound 52

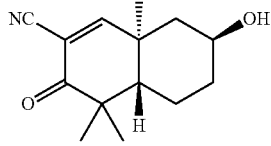

Compound 52 was made in a manner analogous to that already described for compound 4, using (S)-1-phenylethan-1-amine instead of (R)-1-phenylethan-1-amine in the conversion of 2-B to 2-C.

Data for 52:

$^1$H NMR: (400 MHz, CDCl$_3$) δ: 7.47 (s, 1H), 4.07-3.88 (m, 1H), 2.26-2.15 (m, 1H), 1.93 (m, 1H), 1.81-1.72 (m, 2H), 1.57-1.46 (m, 2H), 1.42-1.35 (m, 1H), 1.25 (d, J=10.8 Hz, 7H), 1.08 (s, 3H)

HPLC: (Purity: 95.86%)

LCMS: (M+H: 234.2)

SFC: (Rt=3.749, Purity: 96.07%)

Example 52. Synthesis of Compound 53

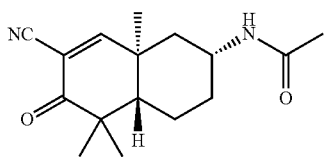

Compound 53 was made in a manner analogous to that already described for compound 22, using (S)-1-phenylethan-1-amine instead of (R)-1-phenylethan-1-amine in the conversion of 2-B to 2-C.

Data for 53:

$^1$HNMR: (400 MHz, Methanol-d$_4$) δ: 7.70 (s, 1H), 4.03 (s, 1H), 2.14-2.10 (m, 1H), 1.95 (s, 3H), 1.88-1.86 (m, 3H), 1.83-1.68 (m, 2H), 1.56 (d, J=9.6 Hz, 1H), 1.32 (s, 3H), 1.21 (s, 3H), 1.12 (s, 3H).

HPLC: Purity: 100%

SFC: (Rt: 3.199 min, ee: 95.60%)

LCMS: (M+H: 275.1).

Example 53. Synthesis of Compound 54

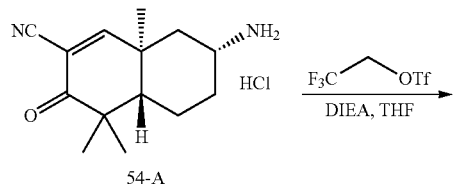

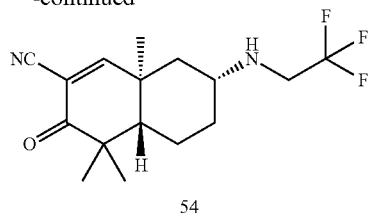

Compound 54-A was obtained in a manner analogous to that already described for compound 22-F, using (S)-1-phenylethan-1-amine instead of (R)-1-phenylethan-1-amine in the conversion of 2-B to 2-C.

A mixture of compound 54-A (120 mg, 0.42 mmol, 1.0 eq), 2,2,2-trifluoroethyl trifluoromethanesulfonate (111.6 mg, 0.48 mmol, 1.1 eq) and DIEA (162 mg, 1.26 mmol, 3.0 eq) in THF (10 mL) was stirred at 75° C. for 16 h. LCMS showed compound 16 was consumed completely. The mixture was purified by prep-HPLC (water (0.05% HCl)-CAN, Phenomenex Synergi C18 150*30 mm*4 um, from 29%-59%, 25 mL/min) to supply compound 54 (7 mg) as yellow solid.

Data for 54:

$^1$HNMR: (400 MHz, CDCl$_3$) δ: 7.44 (s, 1H) 3.11-3.22 (m, 3H) 1.68-1.89 (m, 4H) 1.61 (d, J=4.4 Hz, 1H) 1.49-1.55 (m, 2H) 1.46 (s, 3H) 1.22 (s, 3H) 1.13 (s, 3H).

HPLC: (Purity: 100%)

SFC: (Column: Chiralpak AD-3 150×4.6 mm I.D., 3 um Mobile phase: A: CO2 B: methanol (0.05% DEA) Gradient: from 5% to 40% of B in 5 min and hold 40% for 2.5 min, then 5% of B for 2.5 min Flow rate: 2.5 mL/min Column temp.: 35° C. Rt: 1.053 min, ee: 96.04%)

LCMS: (M+H: 315.1).

Example 54. Synthesis of Compound 55

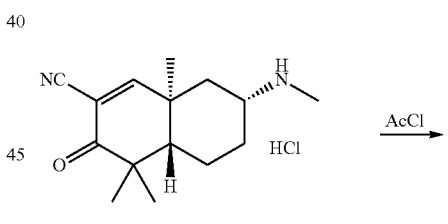

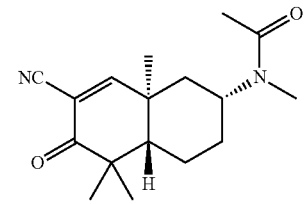

AcCl (18 mg, 1.5 eq, 0.64 mmol) was added to a solution of compound 49-A (120 mg, 0.42 mmol, 1.0 eq), TEA (85 mg, 2.0 eq, 0.84 mmol) in CH$_2$Cl$_2$ 2 mL at 0° C. The mixture was stirred at 20° C. for 1.5 hours. TLC (PE:EtOAc=1:3, Rf=0.5) showed compound 49-A was consumed completely. The mixture was concentrated, and the residue was purified by prep-TLC (PE/EtOAc=1:1) to get compound 55 (53 mg, 42.9% yield).

¹HNMR: (400 MHz, Methanol-d₄) δ: 7.61 (s, 1H), 4.68-4.67 (m, 1H), 2.98 (s, 2H), 2.81 (s, 1H), 2.11-2.04 (m, 5H), 1.85-1.65 (m, 5H), 1.43-1.38 (m, 3H), 1.18 (s, 3H), 1.10 (s, 3H).
HPLC: Purity: 98.74%)
SFC: (Rt: 5.202 min, ee: 98.44%)
LCMS: (M+H: 289.2).

Example 55. Synthesis of Compound 56

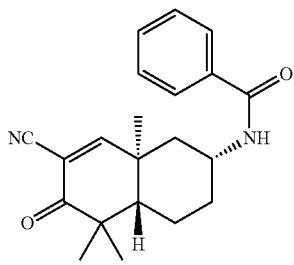

Compound 56 was made in a manner analogous to that already described for compound 34, using (S)-1-phenylethan-1-amine instead of (R)-1-phenylethan-1-amine in the conversion of 2-B to 2-C.

Data for 56:
¹HNMR: (400 MHz, Methanol-d₄) δ: 7.73 (d, J=7.6 Hz, 5H), 7.48-7.55 (m, 4H), 6.09 (s, 1H), 4.23 (s, 1H), 2.25 (d, J=14.4 Hz, 1H), 1.90 (d, J=9.6 Hz, 1H), 1.70-1.85 (m, 5H), 1.40 (s, 3H), 1.26 (s, 3H), 1.14 (s, 3H).
HPLC: (Purity: 97.79%)
SFC: (Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 98.0%)
LCMS: (M+H: 337.1)

Example 56. Synthesis of Compound 57

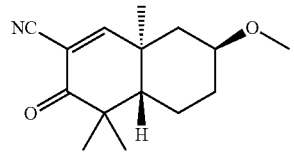

Compound 57 was made in a manner analogous to that already described for compound 6, using (S)-1-phenylethan-1-amine instead of (R)-1-phenylethan-1-amine in the conversion of 2-B to 2-C.

Data for 57:
¹HNMR: (400 MHz, CDCl₃) δ: 7.47 (s, 1H), 3.41-3.48 (m, 1H), 3.37 (s, 3H), 2.28-2.30 (m, 1H), 1.96-1.99 (m, 1H), 1.73-1.77 (m, 1H), 1.49-1.50 (m, 1H), 1.25-1.42 (m, 4H), 1.23 (s, 3H), 1.08 (s, 3H).
HPLC: (Purity: 100%)
SFC: (Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C. (ee: 100%)
LCMS: (M+H): 248.1

Example 57. Synthesis of Compound 58

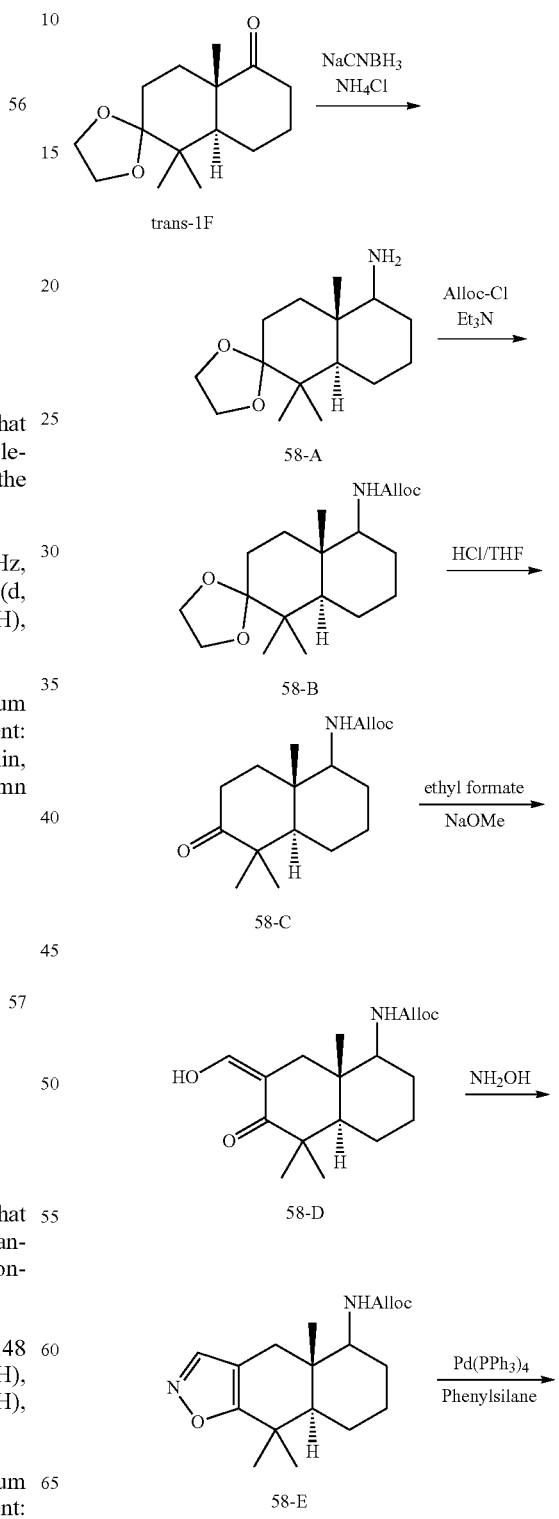

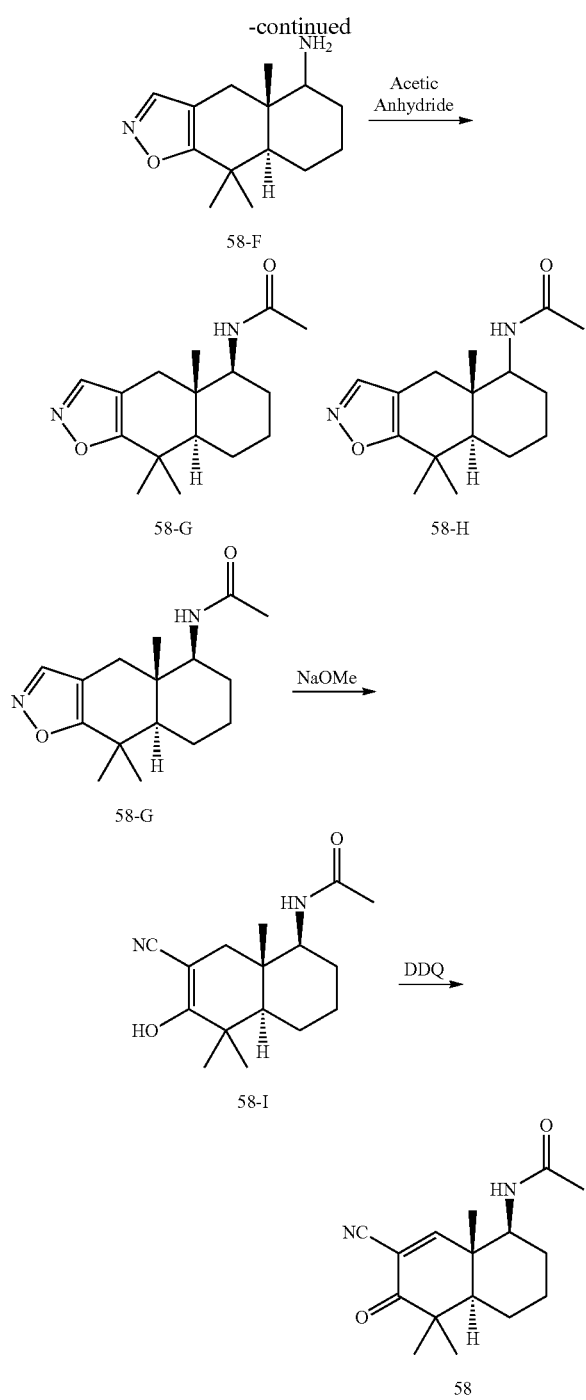

Compound trans-1F can be obtained from 1-F by silica gel column chromatography using a gradient of 5-10% ethyl acetate in heptanes to afford the cis and trans isomers of 1-F. The first eluting isomer is trans-1F.

Data for trans-1F: 1H NMR (400 MHz, CHLOROFORM-d) δ: 0.97-1.14 (m, 6H) 1.20-1.33 (m, 4H) 1.38-1.64 (m, 7H) 1.62-1.79 (m, 3H) 1.80-1.90 (m, 1H) 1.96 (td, J=13.43, 5.27 Hz, 1H) 2.24-2.44 (m, 1H) 2.63 (ddd, J=15.06, 13.80, 6.27 Hz, 1H) 3.77-4.06 (m, 4H).

Preparation of Compound 58-A

Compound trans-1F (1.01 g, 4.00 mmol) in 40 mL methanol was treated with ammonium acetate (6.17 g, 80.00 mmol). After 15 min, Sodium cyanoborohydride (502.72 mg, 8.00 mmol) in 8 mL THF was added over 1 h via syringe and the reaction was stirred at RT for 2 h. The reaction was quenched by addition of sat $Na_2CO_3$ and concentrated to remove methanol. The aqueous phase was extracted with ethyl acetate and the combined organic extracts were washed with brine, dried over MgSO4, filtered, and concentrated to afford a colorless crude oil. Purification on a 12 g silica gel column eluted with 10-60% (90:9:1 DCM:MeOH:$NH_4OH$) in dichloromethane afforded 410 mg of compound 58-A, a roughly 85:12 mixture of (1'S,4'aR,8'aS)-5',5',8'a-trimethylspiro[1,3-dioxolane-2,6'-decalin]-1'-amine as the major isomer by $^1$H-NMR and (1'R,4'aR,8'aS)-5',5',8'a-trimethylspiro[1,3-dioxolane-2,6'-decalin]-1'-amine as the minor isomer.

Data for 58-A: LCMS (M+H)=254.

Preparation of Compound 58-B

Compound 58-A (370 mg) was dissolved in THF (10 mL) and treated with 5 mL of sat $NaHCO_3$. The reaction was cooled to 0° C. Allyl chloroformate (193.57 mg, 1.61 mmol, 171.30 uL) was added and the reaction was allowed to warm to RT slowly. After 2 h, the reaction was diluted with ethyl acetate and brine. The layers were separated and the organic phase was washed with brine, dried over $MgSO_4$, filtered, and concentrated. A crude white solid (420 mg) was obtained, compound 58-B.

Data for 58-B: LCMS (M+H)=338.

Preparation of Compound 58-C

Compound 58-B (420.00 mg, 1.24 mmol) was dissolved in 5 mL THF and treated with 1 mL of 1N HCl. After stirring overnight, the reaction was diluted with 20 mL brine and 60 mL EtOAc. The layers were separated. The aqueous layer was extracted with 20 mL EtOAc. The combined organic phases were washed with sat $NaHCO_3$ and brine, dried over $MgSO_4$, filtered, and concentrated to afford crude compound 58-C which was used directly in the next step.

Preparation of Compound 58-D

Crude compound 58-C (450.00 mg, 1.53 mmol) was dissolved in ethyl formate (11.36 g, 153.37 mmol, 12.35 mL) and treated with sodium methoxide (4.3 M, 1.43 mL). After 6 h, the reaction was quenched by addition of 1N HCL to a pH of ~3 and partitioned between ethyl acetate and brine. The organic phase was dried over $MgSO_4$, filtered, and concentrated to afford an orange oil, compound 58-D. The crude material (550 mg) taken up in absolute ethanol and concentrated back to dryness.

Preparation of Compound 58-E

Crude compound 58-D was dissolved in 10 mL ethanol and 2.5 mL water was treated with Hydroxylamine hydrochloride (300.00 mg, 4.32 mmol, 179.64 uL) overnight. The reaction was concentrated to remove ethanol. The crude material was dissolved in ethyl acetate and washed with sat $NaHCO_3$ and brine. The organic phase was dried over $MgSO_4$, filtered, and concentrated. Purification using 20% ethyl acetate in heptane on a 12 g silica gel column afforded compound 58-E. NMR shows ~85:15 ratio of diastereomers are still present. Data for 58-E: LCMS (M+H)=319.

Preparation of Compounds 58-F, 58-G and 58-H

To a compound 58-E (280.00 mg, 879.37 umol) (and 85:15 mixture of stereoisomers at the amine) in 10 mL of dichloromethane was added phenylsilane (285.47 mg, 2.64 mmol, 324.40 uL) and Pd(PPh$_3$)$_4$ (101.62 mg, 87.94 umol). After 1.5 h, the reaction was concentrated to remove volatiles to afford crude compound 58-F. The crude mixture was reconstituted in 5 mL of dichloromethane and treated with triethylamine (177.97 mg, 1.76 mmol, 243.79 uL) and Acetic anhydride (112.22 mg, 1.10 mmol, 103.91 uL). After 30 min, the reaction was diluted with ethyl acetate and 50% sat NaCl solution. The layers were separated. The organic phase was washed with brine, dried over MgSO$_4$, filtered and concentrated. Purification using 20-40% (3:1 ethyl acetate:ethanol) in heptane on a 12 g silica gel cartridge gave 180 mg of pure equatorial amide product of compound 58-G (180.00 mg, 651.30 umol, 74.06% yield) and 45 mg of compound 58-H as a 6:4 mixture of epimers (favoring the equatorial isomer) at the amine.

Data for 58-G: $^1$H NMR (400 MHz, CHLOROFORM-d) δ: 0.84 (s, 3H) 1.24 (s, 3H) 1.31-1.36 (m, 3H) 1.36-1.53 (m, 3H) 1.65-1.76 (m, 2H) 1.87-1.97 (m, 1H) 2.06 (s, 3H) 2.26-2.55 (m, 1H) 2.26-2.53 (m, 1H) 3.79-4.00 (m, 1H) 5.25-5.49 (m, 1H) 8.01 (s, 1H).
LCMS (M+H)=277.1.

Preparation of Compound 58-I

Compound 58-G (180.00 mg, 651.30 umol) was dissolved in 5 mL of methanol and treated with sodium methoxide (4.3 M, 605.86 uL). The reaction was allowed to stir overnight. The reaction was quenched by addition of 2.5 mL of 1N HCl and concentrated to remove methanol. The reaction was extracted first with dichloromethane and then with ethyl acetate. Note: insoluble matter present. The organic extracts were dried over mgSo4, filtered, and concentrated to afford ~130 mg of a yellow solid. Rinsed flask and filter with THF and combined with solid for a total of 150 mg of crude compound 58-I. Data for 58-I: LCMS (M+H)=277.1.

Preparation of Compound 58

Compound 58-I (150.00 mg, 542.75 umol) was slurried in 6 mL of benzene and treated with DDQ (123.20 mg, 542.75 umol). The mixture was heated to reflux. After 1.5 h, the reaction was cooled to Rt, filtered, and rinsed with benzene. The filtrate contained relatively little desired product compared to the solid. The solid was purified twice by column chromatography using 20-40% acetone in heptanes to afford 60 mg of compound 58 as a white solid.

Data for 58: $^1$H NMR (400 MHz, DMSO-d6) δ: 1.01 (s, 3H) 1.12 (d, J=10.79 Hz, 6H) 1.28-1.66 (m, 5H) 1.79 (br d, J=13.80 Hz, 1H) 1.86 (dd, J=11.92, 2.64 Hz, 1H) 1.93 (s, 3H) 3.32 (s, 1H) 3.64 (ddd, J=12.42, 8.66, 4.02 Hz, 1H) 7.99 (d, J=9.04 Hz, 1H). LCMS (M+H)=275.1. HPLC purity=99.7%.

Example 58. Synthesis of Compound 59

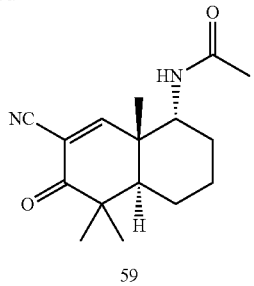

59

Preparation of Compound 59-A Compound 58-H (45.00 mg, 162.83 umol) was dissolved in 1 mL methanol and treated with sodium methoxide (4.3 M, 151.47 uL) for 4 days at RT. The reaction was quenched by addition of 0.65 mL of 1N HCl. The reaction was diluted with ethyl acetate and 50% saturated NaCl solution. Separated layers and extracted aq layer with ethyl acetate. The combined organic layers were washed with brine, dried over mgSo4, filtered, and concentrated to afford crude compound 59-A (45.00 mg, 162.83 umol, 100.00% yield).

Preparation of Compound 59

Compound 59-A was slurried in 3 mL of benzene and treated with DDQ (36.96 mg, 162.83 umol). The mixture was heated to reflux. After 1.5 h, cooled to Rt and concentrated. The entire reaction mixture was deposited on silica gel and purified twice using 20-40% acetone in heptane. On the second column, significant separation of the diastereomers was achieved. One additional chromatographic purification using 80-90% ethyl acetate in heptanes afforded purified compound 59. Data for Compound 59: $^1$H NMR (500 MHz, CHLOROFORM-d) δ: 1.03 (s, 3H) 1.14-1.21 (m, 3H) 1.23-1.28 (m, 3H) 1.28-1.38 (m, 1H) 1.40-1.52 (m, 2H) 1.63 (br d, J=13.43 Hz, 1H) 1.72 (dd, J=12.82, 2.44 Hz, 1H) 1.76-1.92 (m, 2H) 1.93-1.99 (m, 3H) 4.06-4.22 (m, 1H) 5.72 (br d, J=9.16 Hz, 1H) 7.62-7.77 (m, 1H). LCMS (M+H)=275.1. HPLC Purity=98.6%.

Example 59. Synthesis of Compound 60

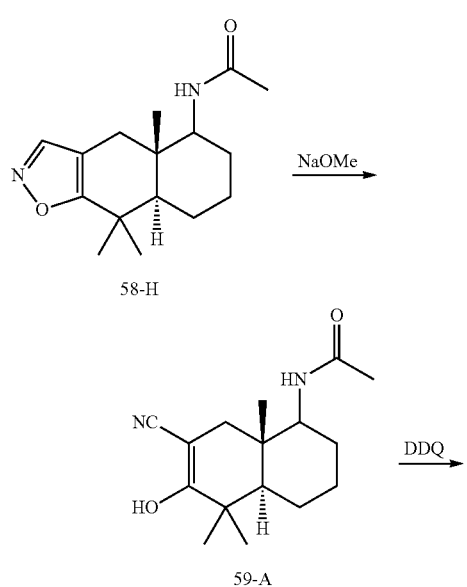

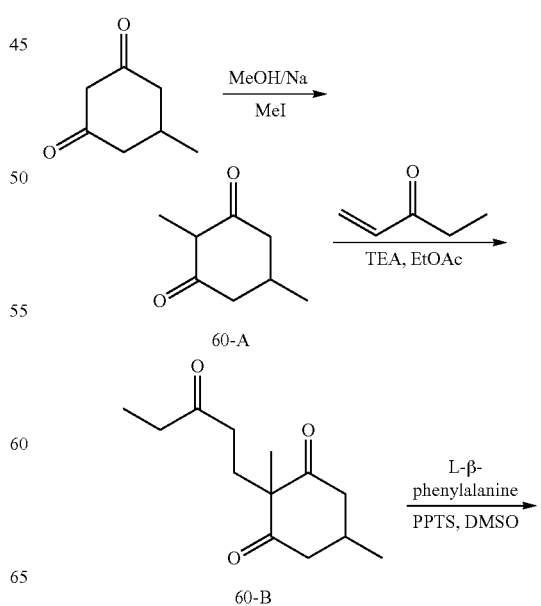

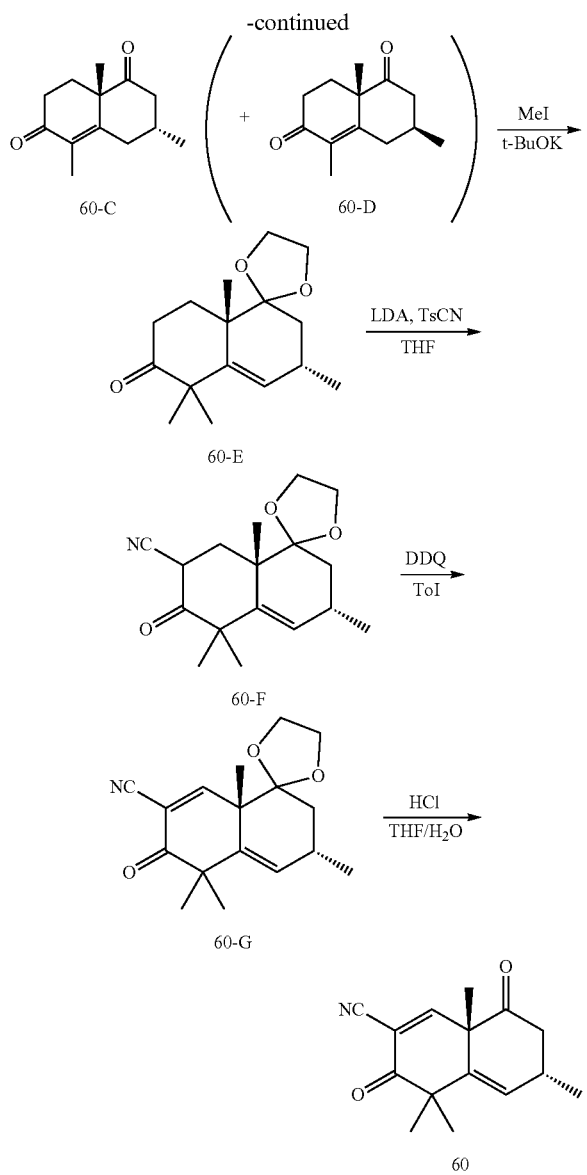

2.37-2.35 (m, 2H), 2.39-2.29 (m, 4H), 2.01 (m, 2H), 1.23-1.18 (m, 1H), 1.17 (s, 3H), 1.07 (d, J=6.8 Hz, 3H), 1.02-0.98 (m, 3H).

Preparation of Compounds 60-C and 60-D

A mixture of compound 60-B (16 g, 0.071 mol, 1.0 eq.), L-β-phenylalanine (3.47 g, 0.021 mol, 0.3 eq.) and PPTS (8.9 g, 0.0355 mol, 0.5 eq.) in DMSO (8 mL) was stirred at 50° C. for 48 hours. LCMS showed the starting material the desired compound was present. The mixture was poured into 30 mL of water, extracted with EtOAc (30 mL×3), the organic layer was dried over anhydrous $Na_2SO_4$, filtered and concentrated. The residue was purified by Prep-HPLC (Column: Gemini 150×25 5 um, Condition: water (0.05% ammonia hydroxide v/v)-ACN, Gradient: 10% to 48% ACN, FlowRate: 80 mL/min) to give about 2.3 g of compound 60-D and 3.3 g of compound 60-C as yellow oil (total yield: ~31%). Data for 60-C: LCMS: (M+H: 206.9); $^1$H-NMR: δ: 2.76-2.68 (m, 2H), 2.63-2.62 (m, 1H), 2.52-2.35 (m, 3H), 2.20-2.08 (m, 3H), 1.80 (s, 3H), 1.40 (s, 3H), 0.96 (d, J=6.8 Hz, 3H).

Preparation of Compound 60-E

To a solution of compound 60-C (0.75 g, 3 mmol, 1.0 eq.) in THF (10 mL) was added t-BuOK (1M in THF, 4.5 ml, 4.5 mmol, 1.5 eq.) dropwise at 0° C. The mixture was stirred at 12° C. for 1 h, then MeI (639 mg, 4.5 mmol, 1.5 eq.) in THF (5 mL) was added, and the mixture was stirred at 12° C. for 3 h. TLC (PE/EA=3/1) showed the reaction was complete. The reaction was quenched with $H_2O$ (30 mL) and extracted with EA (15 mL×3), the combined organic layers were dried over $Na_2SO_4$, filtered and the filtrate was concentrated to give the crude product which was purified by column chromatography (PE:EA=20:1 to 10:1) to give the product of compound 60-E (200 mg, 25% yield) as solid.

$^1$HNMR: (400 MHz, $CDCl_3$) δ: 5.43 (d, J=3.2 Hz, 1H), 4.13-3.84 (m, 4H), 2.67-2.51 (m, 1H), 2.50-2.35 (m, 2H), 2.20-2.19 (m, 1H), 2.01-2.00 (m, 1H), 1.68-1.66 (m, 1H), 1.46-1.43 (m, 1H), 1.24 (s, 6H), 1.14-1.02 (m, 6H).

Preparation of Compound 60-F

To a solution of compound 60-E (0.20 g, 0.76 mmol, 1.0 eq.) in THF (5 mL) was added LDA (2M in hexane, 0.76 mL, 1.52 mmol, 2.0 eq.) at −78° C., the mixture was stirred at this temperature for 1.5 h, then, TsCN (0.27 g, 1.52 mmol, 2.0 eq.) in THF (5 mL) was added, the mixture was stirred at 7° C. for 16 h. TLC (PE/EA=3/1) showed the reaction was complete. The mixture was quenched with sat. $NH_4Cl$ (5 mL) and extracted with EA (5 mL×3), the combined organic layer was dried over $Na_2SO_4$, filtered and the filtrate was concentrated to give the crude product, which was purified by column chromatography (PE:EA=15:1 to 5:1) to give the product of compound 60-F (50 mg, 23%) as solid.

Preparation of Compound 60-G

To a solution of compound 60-F (50 mg, 0.173 mmol, 1.0 eq.) in toluene (10 mL) was added DDQ (59 mg, 0.259 mmol, 2.0 eq.), the mixture was stirred at 50° C. for 3 h. TLC (PE:EA=3:1) showed most 60-F was remained. The mixture was heated to 110° C. for another 3 h. TLC (PE:EA=3:1) showed the reaction was complete. The mixture was concentrated in vacuum. The residue was purified by Pre-TLC (PE/EA=3/1) to give the product of compound 60-G (10 mg, 20%) as yellow solid.

$^1$HNMR: (400 MHz, $CDCl_3$) δ: 7.49 (s, 1H), 5.52 (d, J=3.2 Hz, 1H), 4.03-3.87 (m, 4H), 2.47-2.13 (m, 2H), 2.10-1.97 (m, 1H), 1.44 (s, 3H), 1.33 (s, 3H), 1.31 (s, 3H), 1.03 (d, J=7.6 Hz, 1H).

Preparation of Compound 60

To a mixture of compound 60-G (10 mg, 0.035 mmol, 1.0 eq.) in THF/$H_2O$ (0.5 mL/0.5 mL) was added aq.HCl (6N, Preparation of Compound 60-A MeI (67.53 g, 0.476 mol, 2.0 eq.) was added to 5-methyl-1,3 cyclohexanedione (30 g, 0.238 mol, 1.0 eq.) in 77 mL of NaOH (aq, 4 N, 0.71 mol, 1.3 eq.) at 17-23° C., then the mixture was stirred at 50-60° C. for 18 hours. TLC (PE/EA=1/2) showed the desired compound was detected. The mixture was stirred at 0° C. for 2 hours, filtered and the filter cake was collected and then dried in vacuum to give 13.8 g of compound 60-A (yield ~41.4%) as a white solid which was used.

Preparation of Compound 60-B

A mixture of compound 60-A (13.8 g, 98.6 mmol, 1.0 eq.), ethylvinylketone (19.7 mL, 197 mmol, 2.0 eq.) and $Et_3N$ (41.2 mL, 296 mmol, 3.0 eq.) in 150 mL of EtOAc was stirred at 60° C. for 2 hours. TLC (PE/EA=1/2) showed the starting material was consumed completely, the solvent was removed and the residue was purified by chromatography (PE/EA=20/1) on silica gel to give 16 g of compound 60-B (yield: 72.7%) as a colorless oil (purity ~85%). Data for 60-B: $^1$H-NMR: ($CDCl_3$, 400 MHz) δ: 2.63-2.62 (m, 2H), 1 mL), the mixture was stirred at 70° C. for 16 h. TLC (PE:EA=3:1) showed the reaction was complete. The mixture was concentrated in vacuum to give the product which was further purified by prep-HPLC (Mobile phase A: 0.225% FA-ACN, Mobile phase B: acetonitrile; Column: Agela ASB 150×25 mm×5 um, Detection wavelength: 220 nm) to give compound 60 (3.1 mg, 37% yield) as a light yellow solid.

HPLC: (Purity: 100%).
LCMS: (M+H: 244.2).
$^1$HNMR: (400 MHz, CDCl$_3$) δ: 7.82 (s, 1H), 5.87 (s, 1H), 2.91-2.71 (m, 2H), 2.10-1.96 (m, 1H), 1.56 (s, 3H), 1.38 (s, 3H), 1.37 (s, 3H), 1.13 (d, J=6.4 Hz, 3H).

Example 60. Synthesis of Compound 102: (4aR, 8aS)-4,4,8a-trimethyl-3-oxo-3,4,4a,5,6,7,8,8a-octahydronaphthalene-2-carbonitrile

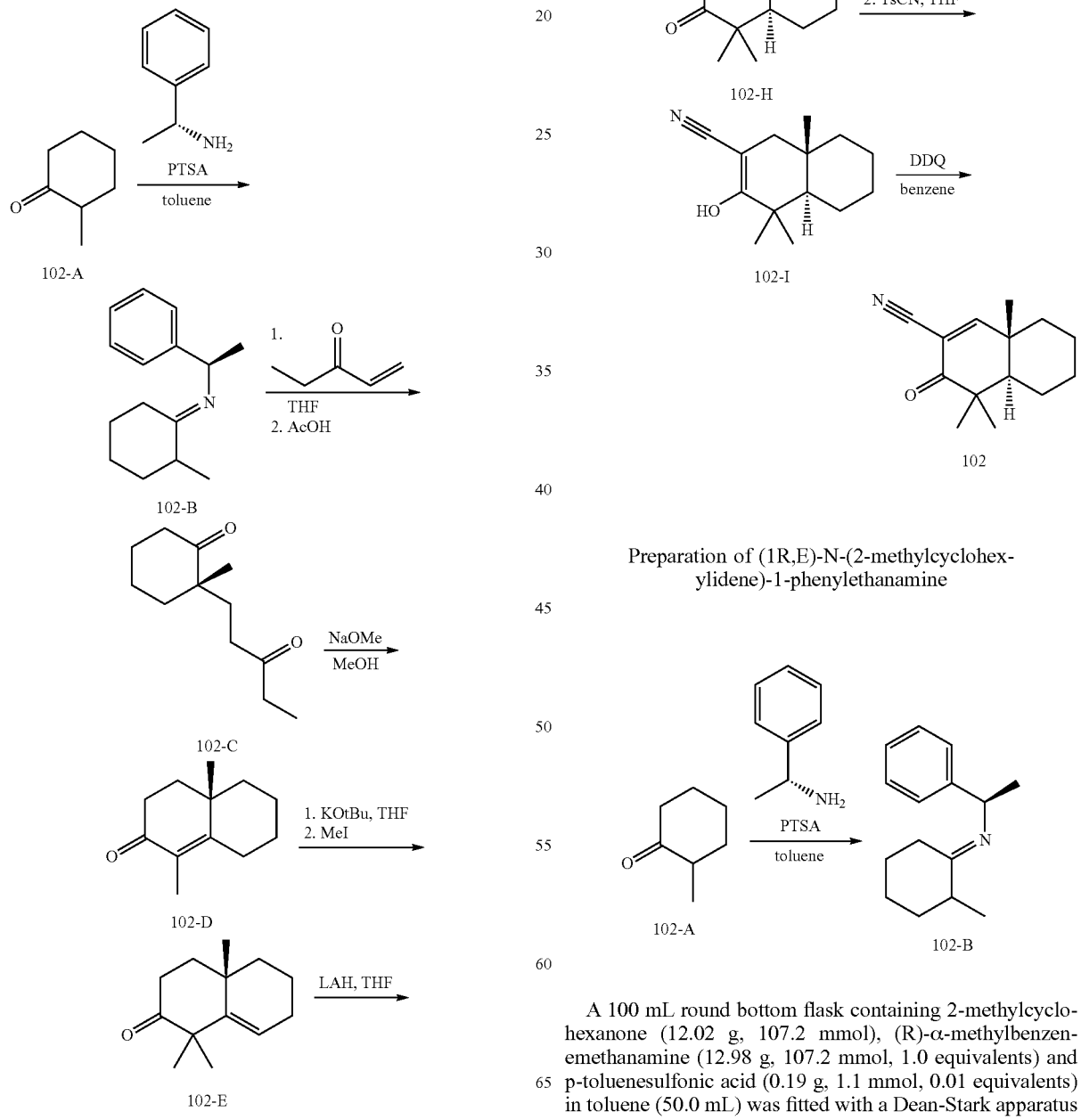

Preparation of (1R,E)-N-(2-methylcyclohexylidene)-1-phenylethanamine

A 100 mL round bottom flask containing 2-methylcyclohexanone (12.02 g, 107.2 mmol), (R)-α-methylbenzenemethanamine (12.98 g, 107.2 mmol, 1.0 equivalents) and p-toluenesulfonic acid (0.19 g, 1.1 mmol, 0.01 equivalents) in toluene (50.0 mL) was fitted with a Dean-Stark apparatus and heated to reflux for 18 h. Solvent was removed in vacuo to afford the crude product of (1R,E)-N-(2-methylcyclohexylidene)-1-phenylethanamine (24.78 g, 107.4% yield).

Preparation of (S)-2-methyl-2-(3-oxopentyl)cyclohexanone

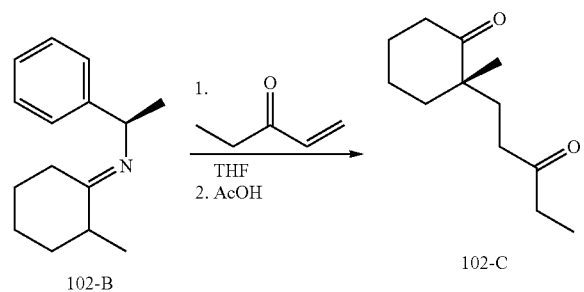

To a solution of (1R,E)-N-(2-methylcyclohexylidene)-1-phenylethanamine (12.61 g, 58.56 mmol) in tetrahydrofuran (23 mL) was added dropwise 1-penten-3-one (11.1 mL, 111 mmol, 1.9 equivalents) and the reaction mixture was stirred at room temperature, under nitrogen, for 7 days. 25 mL of a solution of 20% aqueous acetic acid was added and the mixture was stirred for 3 h. The solvents were removed under reduced pressure, and then 1N HCl was added. The mixture was then extracted with ether and organic phases were treated with brine, dried over sodium sulfate, filtered and concentrated in vacuo. Flash chromatography on silica gel (0-25% ethyl acetate in heptanes as eluent) gave the product of (S)-2-methyl-2-(3-oxopentyl)cyclohexanone (4.82 g, 41.9% yield). ESI-MS (M+H)+: 197.2.

Preparation of (S)-1,4a-dimethyl-4,4a,5,6,7,8-hexahydronaphthalen-2(3H)-one

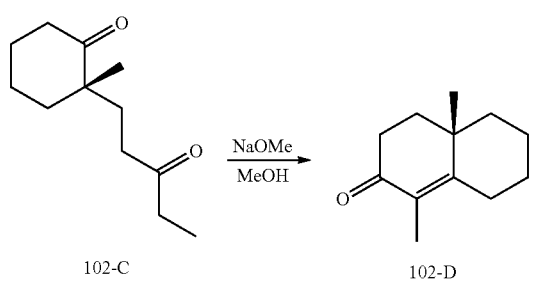

To a 500 mL round bottom flask was added (S)-2-methyl-2-(3-oxopentyl)cyclohexanone (7.50 g, 38.2 mmol) and methanol (250 mL). Sodium (3.8 g, 160 mmol, 4.2 equivalents) was dissolved in methanol (50 mL) at 0° C. and was added via cannula to the first solution. The reaction was heated at 60° C. for 3 h. Solvent was removed under vacuum, and then the residue was diluted with ethyl ether and washed with water. The aqueous layer was adjusted with 1N HCl to pH of 3 and extracted with ethyl ether. The combined organics were washed with brine, dried over sodium sulfate, filtered, and concentrated. The residue was purified on silica gel column using 0-20% ethyl acetate in heptanes as eluent to afford (S)-1,4a-dimethyl-4,4a,5,6,7,8-hexahydronaphthalen-2(3H)-one (5.78 g, 84.9% yield). ESI-MS (M+H)+: 179.1.

Preparation of (S)-1,1,4a-trimethyl-3,4,4a,5,6,7-hexahydronaphthalen-2(1H)-one

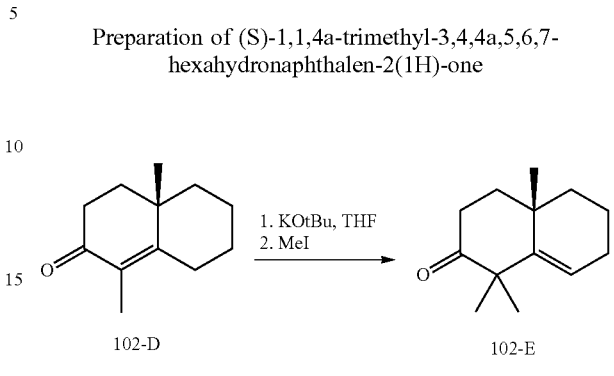

(S)-1,4a-dimethyl-4,4a,5,6,7,8-hexahydronaphthalen-2(3H)-one (4.00 g, 22.4 mmol) was azeotroped twice with anhydrous tetrahydrofuran then taken up in tetrahydrofuran (118 mL). After cooling in a water bath, potassium tert-butoxide (2.770 g, 24.68 mmol, 1.1 equivalents) was added. After 1 h at room temperature, methyl iodide (1536 uL, 24.68 mmol, 1.1 equivalents) was added. After 4 h, the reaction was concentrated and taken back up in ether/water. 1N HCl was added to adjust pH of aq. layer to 3. The organic phase was separated, washed with brine, dried over sodium sulfate, filtered, and concentrated. Purification by silica gel chromatography using 0-20% ethyl acetate in heptanes as eluent afforded (S)-1,1,4a-trimethyl-3,4,4a,5,6,7-hexahydronaphthalen-2(1H)-one (2.759 g, 63.9% yield). ESI-MS (M+H)+: 193.2.

Preparation of (2S,4aS)-1,1,4a-trimethyl-1,2,3,4,4a,5,6,7-octahydronaphthalen-2-ol

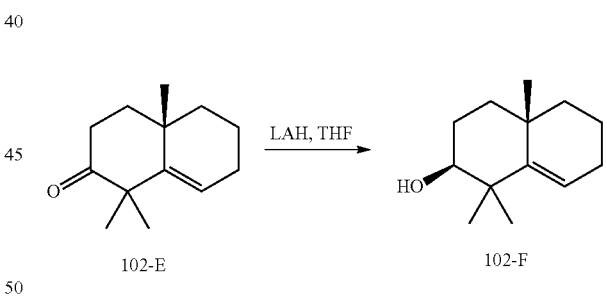

To a solution of (S)-1,1,4a-trimethyl-3,4,4a,5,6,7-hexahydronaphthalen-2(1H)-one (1.008 g, 5.242 mmol) in tetrahydrofuran (8.0 mL) at 0° C. was added 1.00 M of lithium tetrahydroaluminate in tetrahydrofuran (13 mL, 13 mmol, 2.5 equivalents) and the mixture was stirred at room temperature for 1 h. The reaction was cooled, and then was quenched by slow addition of sodium potassium tartrate solution. The organic solvent was removed by evaporation, and then the remaining aqueous mixture was extracted with ether. The organics were washed with saturated sodium chloride, dried over sodium sulfate, filtered and evaporated. The residue was purified by silica gel chromatography using 0-20% ethyl acetate in heptanes as eluent to give the product of (2S,4aS)-1,1,4a-trimethyl-1,2,3,4,4a,5,6,7-octahydronaphthalen-2-ol (1.03 g, 101.3% yield). ESI-MS (M+H)+: 195.2.

Preparation of (2S,4aS,8aR)-1,1,4a-trimethyldecahydronaphthalen-2-ol

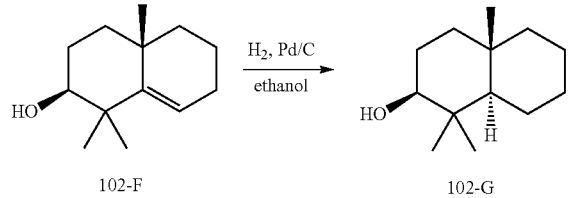

(2S,4aS)-1,1,4a-trimethyl-1,2,3,4,4a,5,6,7-octahydronaphthalen-2-ol (1.0316 g, 5.3090 mmol) was dissolved in ethanol (30 mL) under nitrogen. 10% palladium on carbon (50 mg) was added and the reaction was evacuated under vacuum and replaced with hydrogen (×5). The reaction was stirred under hydrogen balloon for 18 h. Fresh catalyst was added at this time and the reaction was hydrogenated as above for an additional 3 d. The reaction was filtered through Celite, then again through PTFE filter. Solvent was evaporated to give (2S,4aS,8aR)-1,1,4a-trimethyldecahydronaphthalen-2-ol (896.6 mg, 86.0% yield). 1H NMR (400 MHz, CHLOROFORM-d) δ: 3.20-3.28 (m, 1H), 1.82 (d, J=11.80 Hz, 1H), 1.64 (d, J=3.26 Hz, 2H), 1.36-1.49 (m, 4H), 1.00-1.35 (m, 6H), 0.97 (s, 3H), 0.92 (s, 3H), 0.85 (dd, J=2.64, 11.92 Hz, 1H), 0.76 (s, 3H).

Preparation of (4aS,8aR)-1,1,4a-trimethyloctahydronaphthalen-2(1H)-one

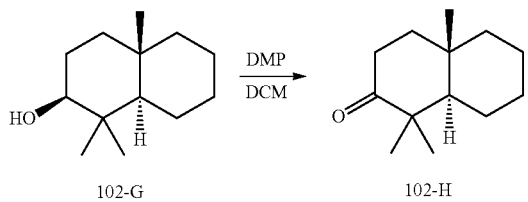

(2S,4aS,8aR)-1,1,4a-trimethyldecahydronaphthalen-2-ol (896.6 mg, 4.567 mmol) was dissolved in methylene chloride (22 mL) and Dess-Martin periodinane (2.324 g, 5.480 mmol, 1.2 equivalents) was added with stirring. After 2 h, the reaction was quenched with 10% sodium thiosulfate in saturated sodium bicarbonate. After stirring for 10 minutes, the reaction was extracted with methylene chloride, dried over magnesium sulfate, filtered, evaporated. The residue was taken up in heptanes, filtered and evaporated. The residue was purified by silica gel chromatography using 3% ethyl acetate in heptanes isocratic as eluent to give the product of (4aS,8aR)-1,1,4a-trimethyloctahydronaphthalen-2(1H)-one (806.9 mg, 90.9% yield). ESI-MS (M+H)+: 195.2.

Preparation of (4aR,8aS)-3-hydroxy-4,4,8a-trimethyl-1,4,4a,5,6,7,8,8a-octahydronaphthalene-2-carbonitrile

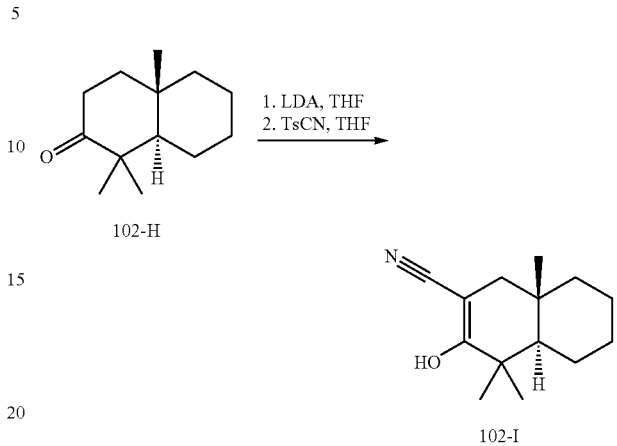

N,N-Diisopropylamine (456 uL, 3.26 mmol, 1.6 equivalents) in tetrahydrofuran (3.8 mL) at −78° C. was treated with 1.6 M of n-butyllithium in hexane (1.85 mL, 2.96 mmol, 1.4 equivalents). The solution was allowed to warm at 0° C. and stir for 30 min. LDA so prepared was cooled at −78° C. and treated with (4aS,8aR)-1,1,4a-trimethyloctahydronaphthalen-2(1H)-one (400.0 mg, 2.058 mmol) in tetrahydrofuran (7.7 mL). After 30 min, p-toluenesulfonyl cyanide (0.536 g, 2.96 mmol, 1.4 equivalents) in tetrahydrofuran (3.8 mL) was added. After stirring for 30 min, 1.00 M of Hydrogen chloride in water (3.1 mL, 3.1 mmol, 1.5 equivalents) was added and the reaction was warmed at 0° C. Volatiles were removed under vacuum, and then the residue was diluted with ethyl acetate and saturated sodium bicarbonate. Organics washed with saturated sodium chloride, dried over sodium sulfate, filtered and evaporated. Residue was purified by silica gel chromatography using 0-20% ethyl acetate in heptanes as eluent to give (4aR,8aS)-3-hydroxy-4,4,8a-trimethyl-1,4,4a,5,6,7,8,8a-octahydronaphthalene-2-carbonitrile (0.2155 g, 47.7%). 1H NMR (400 MHz, CHLOROFORM-d) δ: 3.95-4.01 (m, 1H), 1.79-2.17 (m, 2H), 1.21-1.72 (m, 9H), 0.92-1.21 (m, 9H).

Preparation of (4aR,8aS)-4,4,8a-trimethyl-3-oxo-3,4,4a,5,6,7,8,8a-octahydronaphthalene-2-carbonitrile [102]

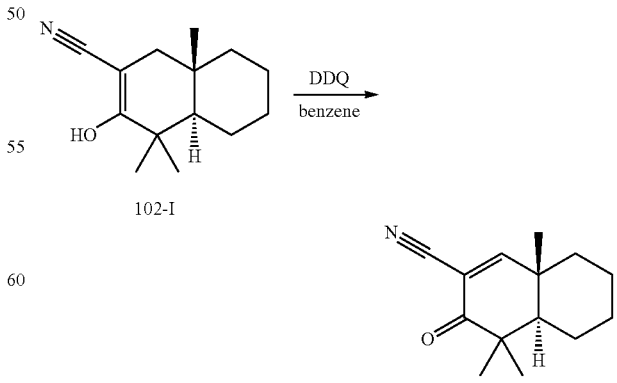

To a solution of (4aR,8aS)-3-hydroxy-4,4,8a-trimethyl-1,4,4a,5,6,7,8,8a-octahydronaphthalene-2-carbonitrile (215.5 mg, 0.9826 mmol) in benzene (22 mL) was added dichlorodicyanoquinone (267.6 mg, 1.179 mmol, 1.2 equivalents). The reaction was heated to reflux for 1 h, and then cooled to room temperature. The reaction mixture was filtered through Celite and rinsed with 10 mL benzene. Silica gel was added, then solvent was concentrated. The loaded silica gel was purified on silica gel column using 0-20% ethyl acetate in heptanes as eluent. The product was repurified using 7.5% ethyl acetate in heptanes (isocratic) as eluent to give (4aR,8aS)-4,4,8a-trimethyl-3-oxo-3,4,4a,5,6,7,8,8a-octahydronaphthalene-2-carbonitrile (112.4 mg, 52.6% yield). ESI-MS (M+H)+: 218.1. 1H NMR (400 MHz, DMSO-d6) δ: 7.91 (s, 1H), 1.71-1.83 (m, 2H), 1.50-1.62 (m, 4H), 1.20-1.49 (m, 3H), 1.18 (s, 3H), 1.10 (s, 3H), 0.98 (s, 3H). Trans ring fusion confirmed by 2D NMR.

Example 61. Synthesis of Compound 103: (4aR,8aS)-4,4,7,7,8a-pentamethyl-3-oxo-3,4,4a,5,6,7,8,8a-octahydronaphthalene-2-carbonitrile

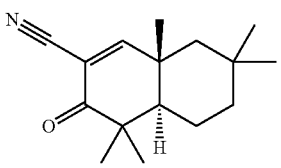

103

(4aR,8aS)-4,4,7,7,8a-pentamethyl-3-oxo-3,4,4a,5,6,7,8,8a-octahydronaphthalene-2-carbonitrile was synthesized as compound 102 but utilizing 2,4,4-trimethylcyclohexanone (103-A) in place of 102-A as the starting ketone.

ESI-MS (M+H)+: 246.1. 1H NMR (400 MHz, DMSO-d6) δ: 7.94 (s, 1H), 1.44-1.70 (m, 5H), 1.31 (d, J=13.30 Hz, 1H), 1.26 (s, 3H), 1.15-1.23 (m, 1H), 1.12 (s, 3H), 1.03 (s, 3H), 1.00 (s, 3H), 0.89 (s, 3H). Trans ring fusion confirmed by 2D NMR.

Preparation of 2,4,4-trimethylcyclohexanone

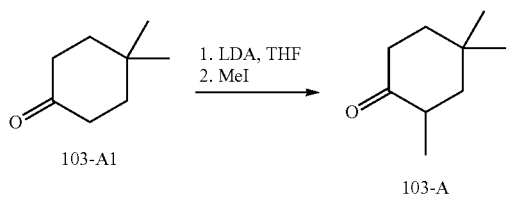

103-A1    103-A

To a solution of N,N-diisopropylamine (12.2 mL, 87.2 mmol, 1.1 equivalents) in tetrahydrofuran (100 mL) was slowly added 1.6 M of n-butyllithium in hexane (54.5 mL, 87.2 mmol, 1.1 equivalents) at 0° C. After stirring at 0° C. for 30 min the solution was cooled to −78° C. Cyclohexanone, 4,4-dimethyl- (10.0 g, 79.2 mmol) in tetrahydrofuran (16 mL) was added dropwise over 30 min and the resulting mixture was stirred for 30 min at −78° C. prior to the addition of methyl iodide (6.60 mL, 106 mmol, 1.3 equivalents). The cooling bath was removed and the solution was allowed to reach ambient temperature and then was stirred for 2 h. The reaction was quenched with saturated aqueous ammonium chloride and then the bulk of the organics were evaporated. The residue was diluted with saturated ammonium chloride, and then extracted with methylene chloride. The organics were washed with aqueous hydrochloric acid (0.1 M) and then with saturated aqueous sodium bicarbonate. The solution was then dried over magnesium sulfate, filtered and carefully evaporated to yield 2,4,4-trimethylcyclohexanone (13.12 g, 118% yield) which was used without further purification. 1H NMR (400 MHz, CHLOROFORM-d) δ 2.41-2.59 (m, 2H), 2.21-2.30 (m, 1H), 1.70-1.78 (m, 2H), 1.55-1.64 (m, 1H), 1.32-1.41 (m, 1H), 1.22 (s, 3H), 0.97-1.02 (m, 6H).

Example 62. Cellular Assay

The assay was performed by DiscoverX Corporation, 42501 Albrae Street, Suite 100, Fremont, Calif. 94538. The PathHunter® Nuclear Translocation assay detects translocation of a target protein to, or from, the nucleus. In this system, ProLink™ (PK), a small enzyme fragment, is fused to the protein of interest and EA is localized in the nucleus. Activation of the signaling pathway induces the target protein to either transit into the nucleus, thus forcing complementation of the PK and EA fragments, or out of the nucleus, hindering complementation of the fragments.

$EC_{50}$ determinations were performed in duplicate at 10 concentrations with 3-fold serial dilutions at a 30 μM top concentration or an otherwise specified top concentration.

Cell Handling:

PathHunter Pathway cell lines were expanded from freezer stocks according to standard procedures. 5000 cells were seeded in Cell Plating Reagent 0 (containing 1% FBS) to a total volume of 20 uL into white walled, 384-well microplates and incubated for the overnight prior to testing.

Agonist Format:

For Agonist determination, cells were incubated with sample to induce response. Sample stocks were serially diluted in DMSO to generate 100× sample. Intermediate dilution of sample stocks was performed to generate 5× sample in assay buffer (Cell Plating Reagent 0 containing 1% FBS). 5 μL of 5× sample was added to cells and incubated at room temperature for 6 hours. Vehicle concentration was 1%.

Signal Detection:

Assay signal was generated through a single addition of 25 μL (100% v/v) of PathHunter Flash Detection reagent, followed by a one hour incubation at room temperature. Microplates were read following signal generation with a PerkinElmer Envision™ instrument for chemiluminescent signal detection.

Data Analysis:

Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX RLU control ligand−mean RLU of vehicle control). For EC50 determination, data was normalized to the maximal and minimal response observed in the presence of the control ligand and vehicle respectively. CDDO methyl ester was used as a control compound.

The compounds described herein were tested for in the above nuclear translocation assay. The results are provided below in Table 2, wherein the compound number corresponds to the numbers set forth in the examples above, a "+" represents an $EC_{50}$ of greater than 10 μM, a "++" represents an $EC_{50}$ of less than or equal to 10 μM, a "+++" represents an EC$_{50}$ of less than or equal to 1 µM and a "++++" represents an EC$_{50}$ of less than or equal to 0.1 µM.

TABLE 2

| COMPOUNDS | EC$_{50}$ (NRF2 TRANS-LOCATION) |
|---|---|
| C, 24 and 60 | ++++ (<0.1 µM) |
| D, 2, 7, 8, 9, 10, 11, 14, 15, 16, 18, 19, 21, 25, 26, 28, 31, 33, 39, 42, 45, 47, 102 and 103 | +++ (<1 µM) |
| A, B, 1-I, 3, 4, 5-B, 5, 6, 12, 13, 20, 22-F, 22, 23, 27, 29, 30, 32, 34, 35, 36, 37, 38, 40, 41, 43, 44, 46, 48, 49, 50, 51, 52, 53, 54, 55, 56, 57 and 58 | ++ (<10 µM) |
| 1-J, 17 and 59 | + (>10 µM) |

Example 63. Testing Nrf2 Activator Compounds in Cultured Human Astrocytes

Cells

Human astrocytes from ScienCell (cat #1820) were grown in astrocyte medium per supplier's instructions. Cells cultured for no more than two passages were plated in 96-well plates at 40,000 cells per well for gene transcription experiments and 20,000 cells per well for glutathione and cytoprotection assays.

Gene Expression

Primary cultures of human spinal cord astrocytes were treated with compound for 20 hours. The cells were then rinsed in PBS, lysed, and processed for RNA using Ambion Taqman™ Cells-to-CT kit. The resulting cDNA was stored at −20° C. until analysis by real-time polymerase chain reaction (RT-PCR). The cDNA mixture from Cells-to-CT was diluted 5× before loading into PCR. This yields results similar to using 6 ng of purified cDNA. RT-PCR was performed on Life Technologies QuantStudio platform using OpenArray technique according to manufacturer's protocol using the following Taqman primers:

| Target | Taq man assay | |
|---|---|---|
| ACTB | Hs01060665_g1 | actin, beta [Homo sapiens (human)] |
| ADAMTS18 | Hs01047394_m1 | ADAM Metallopeptidase With Thrombospondin Type 1 Motif, 18 |
| GAPDH | Hs02758991_g1 | glyceraldehyde-3-phosphate dehydrogenase [Homo sapiens (human)] |
| GCLC | Hs00155249_m1 | glutamate-cysteine ligase, catalytic subunit |
| GCLM | Hs00157694_m1 | glutamate-cysteine ligase, modifier subunit |
| HbG | Hs00361131_g1 | hemoglobin, gamma A [Homo sapiens(human)] |
| HMOX1 | Hs01110250_m1 | heme oxygenase 1 [Homo sapiens (human)] |
| NQO1 | Hs02512143_s1 | NAD(P)H dehydrogenase, quinone 1 |
| OSGIN1 | Hs00203539_m1 | oxidative stress induced growth inhibitor 1 |
| PANX2 | Hs00364526_g1 | Pannexin 2 |
| PINK1 | Hs00260868_m1 | PTEN Induced Putative Kinase 1 |
| PLP1 | Hs00166914_m1 | Proteolipid Protein 1 |

-continued

| Target | Taq man assay | |
|---|---|---|
| PRDX1 | Hs00602020_mH | Peroxiredoxin 6 |
| SLC7A11 | Hs00921934_m1 | Solute Carrier Family 7 (AAA Transporter Light Chain, Xc-System), Member 11 |
| SRXN1 | Hs00607800_m1 | sulfiredoxin 1 |
| TBP | Hs00427620_m1 | TATA box binding protein [Homo sapiens (human)] |
| TXNRD1 | Hs00917067_m1 | thioredoxin reductase 1 |
| UBC | Hs01871556_s1 | ubiquitin C [Homo sapiens (human)] |

The comparative CT method was used to calculate fold changes using ThermoFisher Cloud software for PCR analysis. Samples were compared to vehicle control.

As shown in FIGS. 1A to 1D, Compound 24 induces transcription of Nrf2 target genes, including GCLC, HMOX1, OSGIN1 and NQO1.

Glutathione Assay

Intracellular glutathione was measured after a 20-hr exposure to test compounds by a two-step process. First, cells were lysed and luciferin quantitatively generated from substrate, catalyzed by glutathione-S-transferase in the presence of analyte glutathione. Then luciferin was assayed using stabilized luciferase to produce a luminescent signal proportional to the concentration of glutathione (Promega GSH-Glo, cat #V6912).

Figure 2:
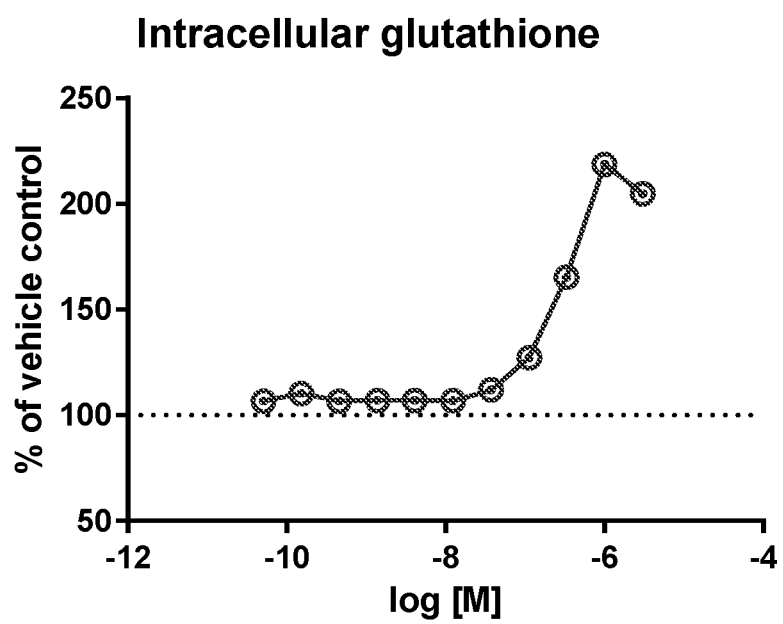
FIG. 2 shows levels of intracellular glutathione Compound 47-Ent1 in human astrocytes treated with increasing concentrations of Compound 24 for 20 hours. The x-axis represents log (molar concentrations of compound 24).

As shown in FIG. 2, Compound 24 increases intracellular glutathione.

Cytoprotection

Astrocytes were treated for 20 hrs as above, then the medium was removed and replaced with serum- and supplement-free growth medium with and without 25 µM sodium arsenite. After 22 hrs., cells were washed with PBS, fixed with 4% paraformaldehyde/4% sucrose in PBS, stained with 4′,6-Diamidino-2-phenylindole dihydrochloride (DAPI) and counted by quantitative fluorescence microscopy.

Figure 3:
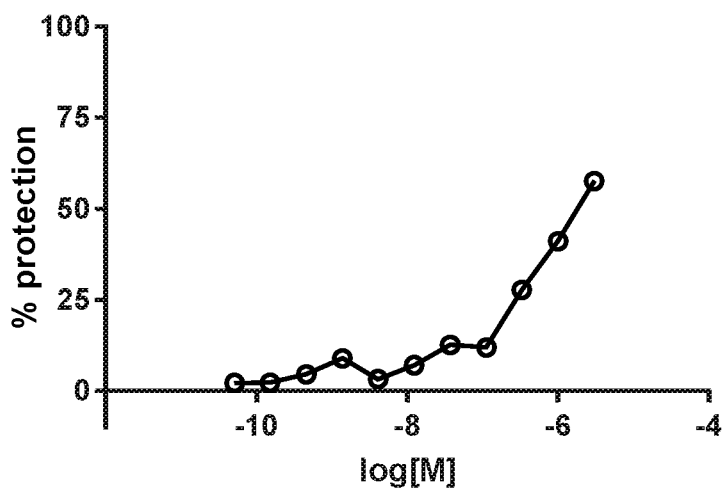
FIG. 3 shows levels of protection of astrocytes by increasing concentrations of Compound 24 from oxidative stress-induced cell death caused by 25 µM sodium arsenite. The compound was added to human astrocytes 20 hrs prior to addition of arsenite and the astrocytes were further incubated for 22 hours after addition of arsenite. The x-axis represents log (molar concentrations of compound 24). This figure shows mean and standard deviation of triplicate determination in one experiment.

As shown in FIG. 3, Compound 24 protects cells from oxidative stress-induced cell death caused by 25 µM sodium arsenite.

What is claimed is:

1. A compound represented by Formula III, IV, V, VI or VII:

(III)

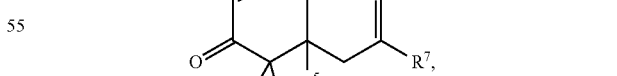

(IV)

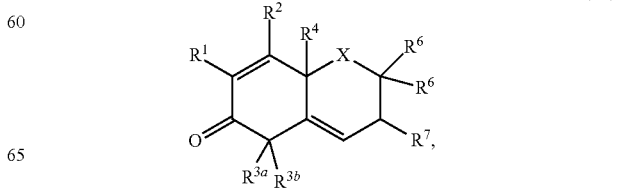

-continued

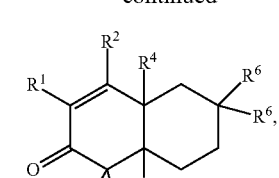
(V)

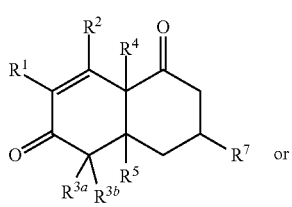
(VI)

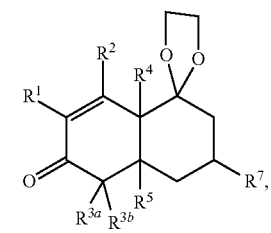
(VII)

or a pharmaceutically acceptable salt thereof, wherein
$R^1$ is —CN;

$R^2$ is H, halo, —$NO_2$, —CN, —$N_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{2a}$, —C(S)$R^{2a}$, —C(O)O$R^{2a}$, —C(S)S$R^{2a}$, —C(O)S$R^{2a}$, —C(S)O$R^{2a}$, —SC(O)$R^{2a}$, —OC(S)$R^{2a}$, —SC(S)$R^{2a}$, —C(O)N($R^{2a}$)$_2$, —O$R^{2a}$, —S$R^{2a}$, —N($R^{2a}$)$_2$, —N($R^{2a}$)O$R^{2a}$, —N($R^{2a}$)S(O)$_2R^{2a}$, —N($R^{2a}$)C(O)$R^{2a}$, —N($R^{2a}$)N($R^{2a}$)$_2$, —N($R^{2a}$)C(O)O$R^{2a}$, —N($R^{2a}$)C(O)N($R^{2a}$)$_2$, —S(O)$_2R^{2a}$, —S(O)$R^{2a}$, —S(O)N($R^{2a}$)$_2$, —S(O)$_2$N($R^{2a}$)$_2$, —$N^+$($R^{2a}$)$_3$, —$S^+$($R^{2a}$)$_2$ or —Si($R^{2a}$)$_3$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more $R^{25}$;

$R^{3a}$ is H, $C_{1-12}$ alkyl, $C_{2-12}$ alkenyl, $C_{2-12}$ alkynyl, a 3 to 12-membered carbocyclyl, a 3 to 12-membered heterocyclyl, —C(O)$R^{30a}$, —C(O)O$R^{30a}$, —C(O)N($R^{30a}$)$_2$, —O$R^{30a}$, —N($R^{30a}$)$_2$, —N($R^{30a}$)O$R^{30a}$, —N($R^{30a}$)S(O)$_2R^{30a}$, —N($R^{30a}$)C(O)$R^{30a}$, —N($R^{30a}$)N($R^{30a}$)$_2$, —N($R^{30a}$)C(O)O$R^{30a}$, —N($R^{30a}$)C(O)N($R^{30a}$)$_2$, —S(O)$R^{30a}$, —S(O)N($R^{30a}$)$_2$ or —S(O)$_2$N($R^{30a}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{35}$; and $R^{3b}$ is $C_{1-12}$alkyl, $C_{2-12}$alkenyl, $C_{2-12}$alkynyl, a 3 to 12-membered carbocyclyl, a 3 to 12-membered heterocyclyl, —C(O)$R^{30b}$, —C(O)O$R^{30b}$, —C(O)N($R^{30b}$)$_2$, —O$R^{30b}$, —N($R^{30b}$)$_2$, —N($R^{30b}$)O$R^{30b}$, —N($R^{30b}$)S(O)$_2R^{30b}$, —N($R^{30b}$)C(O)$R^{30b}$, —N($R^{30b}$)N($R^{30b}$)$_2$, —N($R^{30b}$)C(O)O$R^{30b}$, —N($R^{30b}$)C(O)N($R^{30b}$)$_2$, —S(O)$R^{30b}$, —S(O)N($R^{30b}$)$_2$ or —S(O)$_2$N($R^{30b}$)$_2$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{35}$; or $R^{3a}$ and $R^{3b}$, taken together, are $C_{2-12}$ alkylene, $C_{2-12}$ alkenylene or $C_{2-12}$ alkynylene, wherein the $C_{2-12}$ alkylene, $C_{2-12}$ alkenylene and $C_{2-12}$ alkynylene are each optionally substituted with one or more $R^{35}$;

$R^4$ is H, halo, —$NO_2$, —CN, —$N_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{4a}$, —C(S)$R^{4a}$, —C(O)O$R^{4a}$, —C(S)S$R^{4a}$, —C(O)S$R^{4a}$, —C(S)O$R^{4a}$, —SC(O)$R^{4a}$, —OC(S)$R^{4a}$, —SC(S)$R^{4a}$, —C(O)N($R^{4a}$)$_2$, —O$R^{4a}$, —S$R^{4a}$, —N($R^{4a}$)$_2$, —N($R^{4a}$)O$R^{4a}$, —N($R^{4a}$)S(O)$_2R^{4a}$, —N($R^{4a}$)C(O)$R^{4a}$, —N($R^{4a}$)N($R^{4a}$)$_2$, —N($R^{4a}$)C(O)O$R^{4a}$, —N($R^{4a}$)C(O)N($R^{4a}$)$_2$, —S(O)$_2R^{4a}$, —S(O)$R^{4a}$, —S(O)N($R^{4a}$)$_2$, —S(O)$_2$N($R^{4a}$)$_2$, —$N^+$($R^{4a}$)$_3$, —$S^+$($R^{4a}$)$_2$ or —Si($R^{4a}$)$_3$, wherein the $C_{1-12}$alkyl, $C_{2-12}$alkenyl, $C_{2-12}$alkynyl, 3 to 12-membered carbocyclyl and 3 to 12-membered heterocyclyl are each optionally substituted with one or more $R^{45}$;

$R^5$ is H, halo, —$NO_2$, —CN, —$N_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{5a}$, —C(S)$R^{5a}$, —C(O)O$R^{5a}$, —C(S)S$R^{5a}$, —C(O)S$R^{5a}$, —C(S)O$R^{5a}$, —SC(O)$R^{5a}$, —OC(S)$R^{5a}$, —SC(S)$R^{5a}$, —C(O)N($R^{5a}$)$_2$, —O$R^{5a}$, —S$R^{5a}$, —N($R^{5a}$)$_2$, —N($R^{5a}$)O$R^{5a}$, —N($R^{5a}$)S(O)$_2R^{5a}$, —N($R^{5a}$)C(O)$R^{5a}$, —N($R^{5a}$)N($R^{5a}$)$_2$, —N($R^{5a}$)C(O)O$R^{5a}$, —N($R^{5a}$)C(O)N($R^{5a}$)$_2$, —S(O)$_2R^{5a}$, —S(O)$R^{5a}$, —S(O)N($R^{5a}$)$_2$, —S(O)$_2$N($R^{5a}$)$_2$, —$N^+$($R^{5a}$)$_3$, —$S^+$($R^{5a}$)$_2$ or —Si($R^{5a}$)$_3$, wherein the $C_{1-12}$alkyl, $C_{2-12}$alkenyl, $C_{2-12}$alkynyl, 3 to 12-membered carbocyclyl, and 3 to 12-membered heterocyclyl are each optionally substituted with one or more $R^{55}$;

$R^6$, in each occurrence, is independently H, halo, —$NO_2$, —CN, —$N_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{6a}$, —C(S)$R^{6a}$, —C(O)O$R^{6a}$, —C(S)S$R^{6a}$, —C(O)S$R^{6a}$, —C(S)O$R^{6a}$, —SC(O)$R^{6a}$, —OC(S)$R^{6a}$, —SC(S)$R^{6a}$, —C(O)N($R^{6a}$)$_2$, —O$R^{6a}$, —S$R^{6a}$, —N($R^{6a}$)$_2$, —N($R^{6a}$)O$R^{6a}$, —N($R^{6a}$) S(O)$_2R^{6a}$, —N($R^{6a}$)C(O)$R^{6a}$, —N($R^{6a}$)N($R^{6a}$)$_2$, —N($R^{6a}$)C(O)O$R^{6a}$, —N($R^{6a}$)C(O)N($R^{6a}$)$_2$, —S(O)$_2R^{6a}$, —S(O)$R^{6a}$, —S(O)N($R^{6a}$)$_2$, —S(O)$_2$N ($R^{6a}$)$_2$, —$N^+$($R^{6a}$)$_3$, —$S^+$($R^{6a}$)$_2$ or —Si($R^{6a}$)$_3$; or the two $R^6$ groups, taken together, are oxo, $C_{1-12}$ alkylidene, =$NR^{6a}$ or

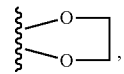

wherein the $C_{1-12}$alkyl, $C_{2-12}$alkenyl, $C_{2-12}$alkynyl, 3 to 12-membered carbocyclyl, 3 to 12-membered heterocyclyl, $C_{1-12}$alkylidene, and

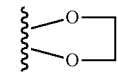

are each optionally substituted with one or more $R^{65}$;

$R^7$, in each occurrence, is independently H, halo, —$NO_2$, —CN, —$N_3$, $C_{1-12}$alkyl, $C_{2-12}$alkenyl, $C_{2-12}$alkynyl, a 3 to 12-membered carbocyclyl, a 3 to 12-membered heterocyclyl, —C(O)$R^{7a}$, —C(S)$R^{7a}$, —C(O)O$R^{7a}$, —C(S)S$R^{7a}$, —C(O)S$R^{7a}$, —C(S)O$R^{7a}$, —SC(O)$R^{7a}$, —OC(S)$R^{7a}$, —SC(S)$R^{7a}$, —C(O)N($R^{7a}$)$_2$, —O$R^{7a}$, —SR$^{7a}$, —N(R$^{7a}$)$_2$, —N(R$^{7a}$)OR$^{7a}$, —N(R$^{7a}$)S(O)$_2$R$^{7a}$, —N(R$^{7a}$)C(O)R$^{7a}$, —N(R$^{7a}$)N(R$^{7a}$)$_2$, —N(R$^{7a}$)C(O)OR$^{7a}$, —N(R$^{7a}$)C(O)N(R$^{7a}$)$_2$, —S(O)$_2$R$^{7a}$, —S(O)R$^{7a}$, —S(O)N(R$^{7a}$)$_2$, —S(O)$_2$N(R$^{7a}$)$_2$, —N$^+$(R$^{7a}$)$_3$, —S$^+$(R$^{7a}$)$_2$ or —Si(R$^{7a}$)$_3$; or the two R$^7$ groups, taken together, are oxo, C$_{1-12}$ alkylidene or =NR$^{7a}$, wherein the C$_{1-12}$alkyl, C$_{2-12}$alkenyl, C$_{2-12}$alkynyl, 3 to 12-membered carbocyclyl, 3 to 12-membered heterocyclyl, and C$_{1-12}$alkylidene are each optionally substituted with one or more R$^{75}$;

X is —C(R$^9$)$_2$—, —C(O)— or

R$^9$, in each occurrence, is independently H, halo, —NO$_2$, —CN, —N$_3$, C$_{1-12}$alkyl, C$_{2-12}$alkenyl, C$_2$-12alkynyl, a 3 to 12-membered carbocyclyl, a 3 to 12-membered heterocyclyl, —C(O)R$^{9a}$, —C(S)R$^{9a}$, —C(O)OR$^{9a}$, —C(S)SR$^{9a}$, —C(O)SR$^{9a}$, —C(S)OR$^{9a}$, —SC(O)R$^{9a}$, —OC(S)R$^{9a}$, —SC(S)R$^{9a}$, —C(O)N(R$^{9a}$)$_2$, —OR$^{9a}$, —SR$^{9a}$, —N(R$^{9a}$)$_2$, —N(R$^{9a}$)OR$^{9a}$, —N(R$^{9a}$)S(O)$_2$R$^{9a}$, —N(R$^{9a}$)C(O)R$^{9a}$, —N(R$^{9a}$)N(R$^{9a}$)$_2$, —N(R$^{9a}$)C(O)OR$^{9a}$, —N(R$^{9a}$)C(O)N(R$^{9a}$)$_2$, —S(O)$_2$R$^{9a}$, —S(O)R$^{9a}$, —S(O)N(R$^{9a}$)$_2$, —S(O)$_2$N(R$^{9a}$)$_2$, —N$^+$(R$^{9a}$)$_3$, —S$^+$(R$^{9a}$)$_2$ or —Si(R$^{9a}$)$_3$; or the two R$^9$ groups, taken together, are oxo, C$_{1-12}$ alkylidene or =NR$^{9a}$, wherein the C$_{1-12}$alkyl, C$_{2-12}$alkenyl, C$_{2-12}$alkynyl, 3 to 12-membered carbocyclyl, 3 to 12-membered heterocyclyl, and C$_{1-12}$alkylidene are each optionally substituted with one or more R$^{95}$;

R$^{2a}$, R$^{30a}$, R$^{30b}$, R$^{4a}$, R$^{5a}$, R$^{6a}$, R$^{7a}$, and R$^{9a}$, in each occurrence, are independently H, C$_{1-12}$alkyl, C$_{2-12}$alkenyl, C$_{2-12}$alkynyl, C$_{1-12}$alkoxy, C$_{1-12}$acyl, —Si(R$^{16}$)$_3$, a 3 to 12-membered carbocyclyl or a 3 to 12-membered heterocyclyl, wherein the C$_{1-12}$alkyl, C$_{2-12}$alkenyl, C$_{2-12}$alkynyl, C$_{1-12}$alkoxy, C$_{1-12}$acyl, 3 to 12-membered carbocyclyl, and 3 to 12-membered heterocyclyl are each optionally substituted with one or more R$^{17}$;

R$^{16}$, in each occurrence, is independently H, C$_{1-12}$alkyl, C$_{2-12}$alkenyl, C$_{2-12}$alkynyl, a 3 to 12-membered carbocyclyl or a 3 to 12-membered heterocyclyl, wherein the C$_{1-12}$alkyl, C$_{2-12}$alkenyl, C$_{2-12}$alkynyl, 3 to 12-membered carbocyclyl, and 3 to 12-membered heterocyclyl are each optionally substituted with one or more R$^{18}$;

R$^{25}$, R$^{35}$, R$^{45}$, R$^{55}$, R$^{65}$, R$^{75}$, and R$^{95}$, in each occurrence, are independently halo, —OH, —CN, C$_{1-12}$alkyl, C$_{2-12}$alkenyl, C$_{2-12}$alkynyl, C$_{1-12}$alkoxy, a 3 to 12-membered carbocyclyl or a 3 to 12-membered heterocyclyl, wherein the C$_{1-12}$alkyl, C$_{2-12}$alkenyl, C$_{2-12}$alkynyl, C$_{1-12}$alkoxy, 3 to 12-membered carbocyclyl, and 3 to 12-membered heterocyclyl are each optionally substituted with one or more R$^{19}$; and R$^{17}$, R$^{18}$, and R$^{19}$, in each occurrence, are independently halo, —OH, —CN, C$_{1-12}$alkyl, C$_{2-12}$alkenyl, C$_{2-12}$alkynyl, C$_{1-12}$alkoxy, a 3 to 12-membered carbocyclyl or a 3 to 12-membered heterocyclyl, wherein the C$_{1-12}$alkyl, C$_{2-12}$alkenyl, C$_{2-12}$alkynyl, C$_{1-12}$alkoxy, 3 to 12-membered carbocyclyl and 3 to 12-membered heterocyclyl are each optionally substituted with one or more groups independently selected from halo, —OH, and C$_{1-4}$alkoxy.

2. The compound of claim 1, wherein the compound is represented by Formula IIIA, IIIB, IIIC, IIID, IVA or IVB:

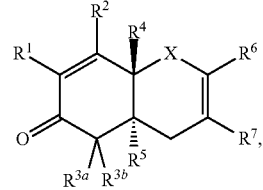
(IIIA)

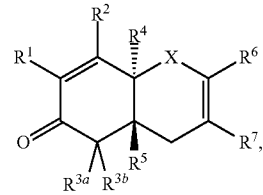
(IIIB)

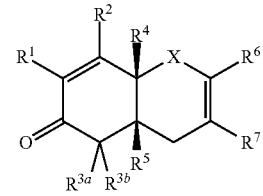
(IIIC)

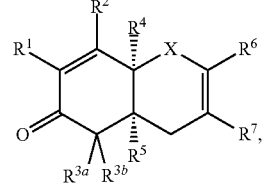
(IIID)

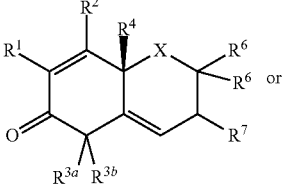
(IVA)

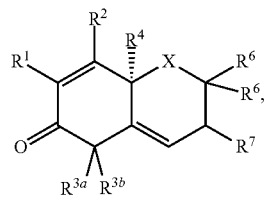
(IVB)

or a pharmaceutically acceptable salt thereof.

3. The compound of claim 1, or a pharmaceutically acceptable salt thereof, wherein X is —C(R$^9$)$_2$—, —C(O)—, or

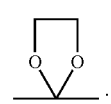

wherein

R$^9$, in each occurrence, is independently H, halo, —CN, —OR$^{9a}$, C$_{1-12}$alkyl, C$_{2-12}$alkenyl or C$_2$-12alkynyl, wherein the C$_{1-12}$alkyl, C$_{2-12}$alkenyl, and C$_{2-12}$alkynyl are each optionally substituted with one to eight R$^{95}$;

$R^{9a}$ is H, $C_{1-12}$alkyl, $C_{2-12}$alkenyl or $C_{2-12}$alkynyl, wherein the $C_{1-12}$alkyl, $C_{2-12}$alkenyl, and $C_{2-12}$alkynyl are each optionally substituted with one to six $R^{17}$;

$R^{95}$, in each occurrence, is independently halo, —OH, —CN, $C_{1-12}$alkyl, $C_{2-12}$alkenyl, $C_{2-12}$alkynyl or $C_{1-12}$alkoxy, wherein the $C_{1-12}$alkyl, $C_{2-12}$alkenyl, $C_{2-12}$alkynyl, and $C_{1-12}$alkoxy are each optionally substituted with one to six groups independently selected from halo, —OH, and $C_{1-4}$alkoxy; and $R^{17}$, in each occurrence, as an optional substituent of $R^{9a}$, is independently halo, —CN, —OH, $C_{1-6}$alkyl or $C_{1-6}$alkoxy, wherein the $C_{1-6}$alkyl and $C_{1-6}$alkoxy are optionally substituted with one to six halo.

4. The compound of claim 3, wherein the compound is represented by one of Formula VIII, XI and X:

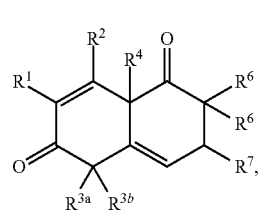
(VIII)

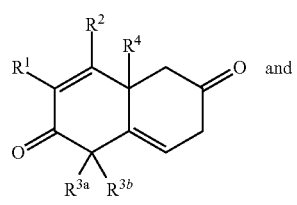
(IX) and

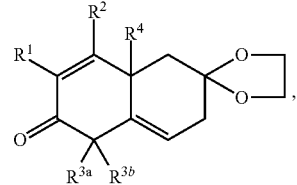
(X)

or a pharmaceutically acceptable salt thereof.

5. The compound of claim 1, wherein the compound is represented by one of Formula VA, VB, VC, VD, VIA, VIB, VIC, VID, VIIA, VIIB, VIIC, VIID VIIIA, VIIIB, IXA, IXB, XA and XB:

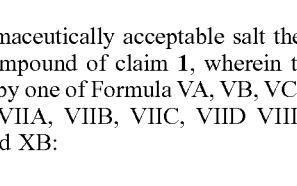
(VA)

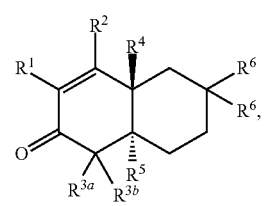
(VB)

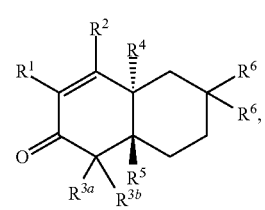

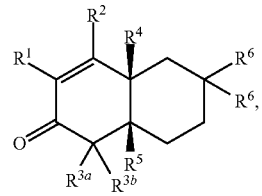
(VC)

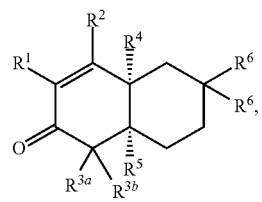
(VD)

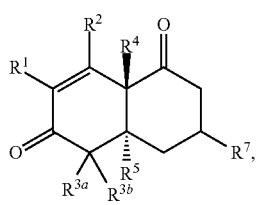
(VIA)

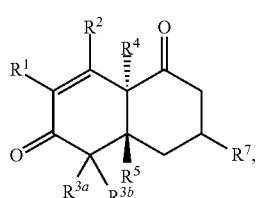
(VIB)

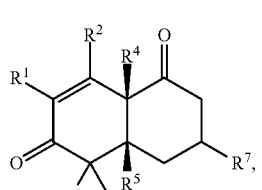
(VIC)

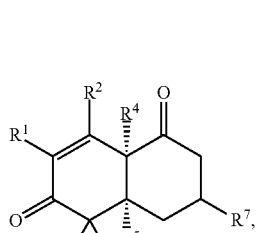
(VID)

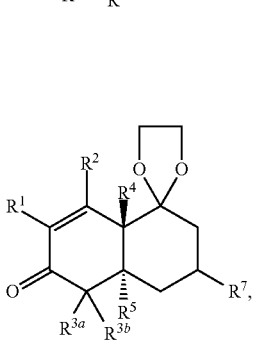
(VIIA)

-continued (VIIB)

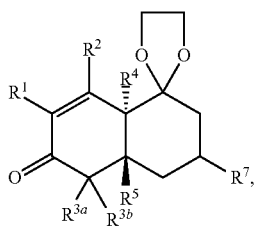

(VIIC)

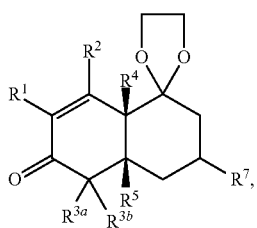

(VIID)

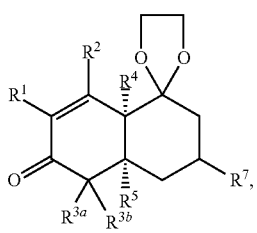

(VIIIA)

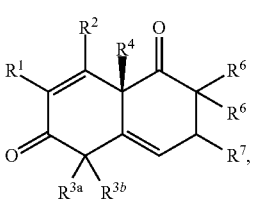

(VIIIB)

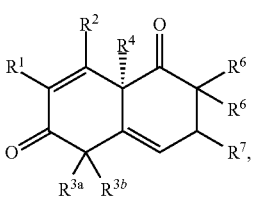

(IXA)

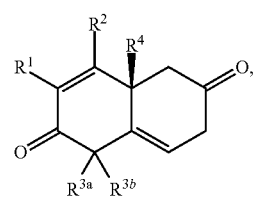

(IXB)

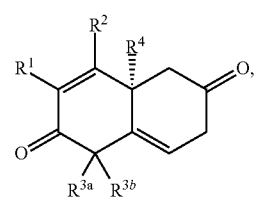

-continued (XA)

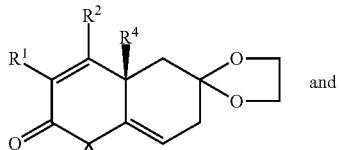

and (XB)

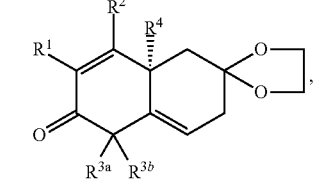

or a pharmaceutically acceptable salt thereof.

6. The compound of claim 1, or a pharmaceutically acceptable salt thereof, wherein $R^6$, in each occurrence, is independently H, halo, —CN, —OR$^{6a}$, —N(R$^{6a}$)$_2$, —N(R$^{6a}$)S(O)$_2$R$^{6a}$, —N(R$^{6a}$)C(O)R$^{6a}$, C$_{1-12}$alkyl, C$_{2-12}$alkenyl, C$_{2-12}$alkynyl, a 3 to 12-membered carbocyclyl or a 3 to 12-membered heterocyclyl; or the two R$^6$ groups, taken together, are oxo, C$_{1-12}$ alkylidene or

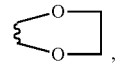

wherein the C$_1$-12alkyl, C$_{2-12}$alkenyl, C$_{2-12}$alkynyl, a 3 to 12-membered carbocyclyl, a 3 to 12-membered heterocyclyl, C$_{1-12}$ alkylidene, and

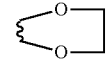

are each optionally substituted with one to eight R$^{65}$;

R$^{6a}$, in each occurrence, is independently H, C$_{1-12}$alkyl, C$_{2-12}$alkenyl, C$_{2-12}$alkynyl or a 3 to 12-membered carbocyclyl, wherein the C$_{1-12}$alkyl, C$_{2-12}$alkenyl, C$_{2-12}$alkynyl, C$_{1-12}$acyl, and 3 to 12-membered carbocyclyl are each optionally substituted with one to six R$^{17}$;

R$^7$, in each occurrence, is independently H, halo, —CN, —OR$^{7a}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{75}$;

R$^{7a}$, in each occurrence, is independently H, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to six R$^{17}$;

R$^{65}$, in each occurrence, is independently halo, —OH, —CN, C$_{1-12}$alkyl, C$_{2-12}$alkenyl, C$_{2-12}$alkynyl, C$_{1-12}$alkoxy or a 3 to 12-membered carbocyclyl, wherein the C$_{1-12}$alkyl, C$_{2-12}$alkenyl, C$_{2-12}$alkynyl, C$_{1-12}$alkoxy, and 3 to 12-membered carbocyclyl are each optionally substituted with one to six groups independently selected from halo, —OH, and C$_{1-6}$alkoxy;

R$^{75}$, in each occurrence, is independently halo, —OH, —CN, C$_{1-12}$alkyl, C$_{2-12}$alkenyl, C$_{2-12}$alkynyl or C$_{1-12}$alkoxy, wherein the C$_{1-12}$alkyl, C$_{2-12}$alkenyl, C$_{2-12}$alkynyl, and C$_{1-12}$alkoxy are each optionally substituted with one to six groups independently selected from halo, —OH, and C$_{1-4}$alkoxy; and R$^{17}$, in each occurrence, as an optional substituent of R$^{6a}$ or R$^{7a}$, is independently halo, —CN, —OH, C$_{1-12}$alkyl, C$_{1-6}$alkoxy or a 3 to 12-membered carbocyclyl, wherein the C$_{1-6}$alkyl, C$_{1-6}$alkoxy, and 3 to 12-membered carbocyclyl are each optionally substituted with one to six halo.

7. The compound of claim 1, or a pharmaceutically acceptable salt thereof, wherein R$^2$ is H, halo, —CN, —OR$^{2a}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{25}$;

R$^{2a}$ is selected from H, C$_{1-12}$alkyl, C$_{2-12}$alkenyl, and C$_{2-12}$alkynyl, wherein the C$_{1-12}$alkyl, C$_{2-12}$alkenyl, and C$_{2-12}$alkynyl are each optionally substituted with one to six R$^{17}$;

R$^{25}$, in each occurrence, is independently selected from halo, —OH, —CN, C$_{1-12}$alkyl, C$_{2-12}$alkenyl, C$_{2-12}$alkynyl, and C$_{1-12}$alkoxy, wherein the C$_{1-12}$alkyl, C$_{2-12}$alkenyl, C$_{2-12}$alkynyl, and C$_{1-12}$alkoxy are each optionally substituted with one to six groups independently selected from halo, —OH, and C$_{1-4}$alkoxy; and R$^{17}$, in each occurrence, as an optional substituent of R$^{2a}$, is independently selected from halo, —CN, —OH, C$_{1-6}$alkyl, and C$_{1-6}$alkoxy, wherein the C$_{1-6}$alkyl and C$_{1-6}$alkoxy are each optionally substituted with one to six halo.

8. The compound of claim 1, or a pharmaceutically acceptable salt thereof, wherein R$^{3a}$ is H, halo, —CN, —OR$^{30a}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{35}$;

R$^{3b}$ is halo, —CN, —OR$^{30b}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{35}$;

R$^{30a}$ and R$^{30b}$ are each independently selected from H, C$_{1-12}$alkyl, C$_{2-12}$alkenyl, and C$_{2-12}$alkynyl, wherein the C$_{1-12}$alkyl, C$_{2-12}$alkenyl, and C$_{2-12}$alkynyl are each optionally substituted with one to six R$^{17}$;

R$^{35}$, in each occurrence, is independently selected from halo, —OH, —CN, C$_{1-12}$alkyl, C$_{2-12}$alkenyl, C$_{2-12}$alkynyl, and C$_{1-12}$alkoxy, wherein the C$_{1-12}$alkyl, C$_{2-12}$alkenyl, C$_{2-12}$alkynyl, and C$_{1-12}$alkoxy are each optionally substituted with one to six groups independently selected from halo, —OH, and C$_{1-4}$alkoxy; and R$^{17}$, in each occurrence, as an optional substituent of R$^{30a}$ or R$^{30b}$, is independently selected from halo, —CN, —OH, C$_{1-6}$alkyl, and C$_{1-6}$alkoxy, wherein the C$_{1-6}$alkyl and C$_{1-6}$alkoxy are each optionally substituted with one to six halo.

9. The compound of claim 1, or a pharmaceutically acceptable salt thereof, wherein R$^4$ is H, halo, —CN, —OR$^{4a}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{45}$;

R$^{4a}$ is selected from H, C$_{1-12}$alkyl, C$_{2-12}$alkenyl, and C$_{2-12}$alkynyl, wherein the C$_{1-12}$alkyl, C$_{2-12}$alkenyl, and C$_{2-12}$alkynyl are each optionally substituted with one to six R$^{17}$;

R$^{45}$, in each occurrence, is independently selected from halo, —OH, —CN, C$_{1-12}$alkyl, C$_{2-12}$alkenyl, C$_{2-12}$alkynyl, and C$_{1-12}$alkoxy, wherein the C$_{1-12}$alkyl, C$_{2-12}$alkenyl, C$_{2-12}$alkynyl, and C$_{1-12}$alkoxy are each optionally substituted with one to six groups independently selected from halo, —OH, and C$_{1-4}$alkoxy; and R$^{17}$, in each occurrence, as an optional substituent of R$^{4a}$, is independently selected from halo, —CN, —OH, C$_{1-6}$alkyl, and C$_{1-6}$alkoxy, wherein the C$_{1-6}$alkyl and C$_{1-6}$alkoxy are each optionally substituted with one to six halo.

10. The compound of claim 1, or a pharmaceutically acceptable salt thereof, wherein R$^5$ is H, halo, —CN, —OR$^{5a}$, C$_{1-12}$alkyl, C$_{2-12}$alkenyl or C$_{2-12}$alkynyl, wherein the C$_{1-12}$alkyl, C$_{2-12}$alkenyl, and C$_{2-12}$alkynyl are each optionally substituted with one to eight R$^{55}$;

R$^{5a}$ is selected from H, C$_{1-12}$alkyl, C$_{2-12}$alkenyl, and C$_{2-12}$alkynyl, wherein the C$_{1-12}$alkyl, C$_{2-12}$alkenyl, and C$_{2-12}$alkynyl are each optionally substituted with one to six R$^{17}$;

R$^{55}$, in each occurrence, is independently selected from halo, —OH, —CN, C$_{1-12}$alkyl, C$_{2-12}$alkenyl, C$_{2-12}$alkynyl, and C$_{1-12}$alkoxy, wherein the C$_{1-12}$alkyl, C$_{2-12}$alkenyl, C$_{2-12}$alkynyl, and C$_{1-12}$alkoxy are each optionally substituted with one to eight groups independently selected from halo, —OH, and C$_{1-4}$alkoxy; and R$^{17}$, in each occurrence, as an optional substituent of R$^{5a}$, is independently selected from halo, —CN, —OH, C$_{1-6}$alkyl, and C$_{1-6}$alkoxy, wherein the C$_{1-6}$alkyl and C$_{1-6}$alkoxy are each optionally substituted with one to six halo.

11. A compound selected from the group consisting of:
(4'aR,8'aS)-4',4',8'a-trimethyl-3'-oxo-spiro[1,3-dioxolane-2,7'-4a,5,6,8-tetrahydronaphthalene]-2'-carbonitrile,
(4aR,8aS)-4,4,8a-trimethyl-3,7-dioxo-4a,5,6,8-tetrahydronaphthalene-2-carbonitrile,
(4aS,8aS)-4,4,8a-trimethyl-3,8-dioxo-4a,5,6,7-tetrahydronaphthalene-2-carbonitrile,
(4aR,8aS)-4,4,8a-trimethyl-3-oxo-5,6,7,8-tetrahydro-4aH-naphthalene-2-carbonitrile,
(4aR,8aS)-4,4,7,7,8a-pentamethyl-3-oxo-4a,5,6,8-tetrahydronaphthalene-2-carbonitrile,
(4aS,7S,8aS)-7-hydroxy-4,4,8a-trimethyl-3-oxo-5,6,7,8-tetrahydro-4aH-naphthalene-2-carbonitrile,
(4aS,7S,8aS)-7-methoxy-4,4,8a-trimethyl-3-oxo-5,6,7,8-tetrahydro-4aH-naphthalene-2-carbonitrile,
(4aS,8aS)-7,7-difluoro-4,4,8a-trimethyl-3-oxo-4a,5,6,8-tetrahydronaphthalene-2-carbonitrile,
(4aS,7R,8aS)-7-hydroxy-4,4,8a-trimethyl-3-oxo-5,6,7,8-tetrahydro-4aH-naphthalene-2-carbonitrile,
(S)-5,5,8a-trimethyl-6-oxo-3,5,6,8a-tetrahydro-1H-spiro[naphthalene-2,2'-[1,3]dioxolane]-7-carbonitrile,
(4aR,8aS)-4,4,8a-trimethyl-7-methylene-3-oxo-4a,5,6,8-tetrahydronaphthalene-2-carbonitrile,
(8aS)-4,4,8a-trimethyl-3,7-dioxo-6,8-dihydronaphthalene-2-carbonitrile,
(4aS,6S,8aS)-4,4,6,8a-tetramethyl-3,8-dioxo-4a,5,6,7-tetrahydronaphthalene-2-carbonitrile,
(4aS,6S,8aS)-6-ethyl-4,4,8a-trimethyl-3,8-dioxo-4a,5,6,7-tetrahydronaphthalene-2-carbonitrile,
(4aS,7S,8aS)-7-hydroxy-4,4,7,8a-tetramethyl-3-oxo-4a,5,6,8-tetrahydronaphthalene-2-carbonitrile,
(4aS,6R,8aS)-4,4,6,8a-tetramethyl-3,8-dioxo-4a,5,6,7-tetrahydronaphthalene-2-carbonitrile, (4aS,8aS)-4,4,7,8a-tetramethyl-3-oxo-5,8-dihydro-4aH-naphthalene-2-carbonitrile,
(4aS,7S,8aS)-7-hydroxy-4,4,8a-trimethyl-3-oxo-7-(trifluoromethyl)-4a,5,6,8-tetrahydronaphthalene-2-carbonitrile,
(4aS,7R,8aS)-7-benzyl-4,4,8a-trimethyl-3-oxo-5,6,7,8-tetrahydro-4aH-naphthalene-2-carbonitrile,
(4aS,7R,8aS)-7-methoxy-4,4,8a-trimethyl-3-oxo-5,6,7,8-tetrahydro-4aH-naphthalene-2-carbonitrile, (4aR,7E,8aS)-7-benzylidene-4,4,8a-trimethyl-3-oxo-4a,8-dihydronaphthalene-2-carbonitrile,
(6R,8aS)-6-ethyl-4,4,8a-trimethyl-3,8-dioxo-4a,5,6,7-tetrahydronaphthalene-2-carbonitrile,
(4aS,7R,8aS)-7-fluoro-4,4,8a-trimethyl-3-oxo-5,6,7,8-tetrahydro-4aH-naphthalene-2-carbonitrile,
(4aS,8aS)-4,4,8a-trimethyl-3-oxo-5,8-dihydro-4aH-naphthalene-2-carbonitrile,
(4aS,7R,8aS)-7-benzyl-7-hydroxy-4,4,8a-trimethyl-3-oxo-4a,5,6,8-tetrahydronaphthalene-2-carbonitrile,
(4aS,7S,8aS)-7-methoxy-4,4,7,8a-tetramethyl-3-oxo-4a,5,6,8-tetrahydronaphthalene-2-carbonitrile,
(4aS,8aS)-7-benzyl-4,4,8a-trimethyl-3-oxo-5,8-dihydro-4aH-naphthalene-2-carbonitrile,
(4aS,7R,8aS)-7-benzyl-7-methoxy-4,4,8a-trimethyl-3-oxo-4a,5,6,8-tetrahydronaphthalene-2-carbonitrile,
N-[(2S,4aS,8aS)-7-cyano-5,5,8a-trimethyl-6-oxo-2,3,4,4a-tetrahydro-1H-naphthalen-2-yl]acetamide,
(4aR,7E,8aS)-7-benzylidene-4,4,8a-trimethyl-3-oxo-4a,5,6,8-tetrahydronaphthalene-2-carbonitrile,
(4aS,7S,8aS)-7-hydroxy-4,4,8a-trimethyl-3-oxo-7-phenyl-4a,5,6,8-tetrahydronaphthalene-2-carbonitrile,
(4aS,8aS)-4,4,8a-trimethyl-3-oxo-7-phenyl-5,8-dihydro-4aH-naphthalene-2-carbonitrile,
(4aS,7R,8aS)-7-hydroxy-4,4,8a-trimethyl-3-oxo-7-(3-pyridyl)-4a,5,6,8-tetrahydronaphthalene-2-carbonitrile hydrochloride,
(4aS,7S,8aS)-4,4,8a-trimethyl-3-oxo-7-phenyl-5,6,7,8-tetrahydro-4aH-naphthalene-2-carbonitrile,
(4aS,7S,8aS)-4,4,8a-trimethyl-7-(methylamino)-3-oxo-5,6,7,8-tetrahydro-4aH-naphthalene-2-carbonitrile hydrochloride,
(4aS,7S,8aS)-4,4,8a-trimethyl-7-morpholino-3-oxo-5,6,7,8-tetrahydro-4aH-naphthalene-2-carbonitrile,
(4aS,7S,8aS)-7-(benzylamino)-4,4,8a-trimethyl-3-oxo-5,6,7,8-tetrahydro-4aH-naphthalene-2-carbonitrile,
(6S,8aS)-4,4,6,8a-tetramethyl-3,8-dioxo-6,7-dihydronaphthalene-2-carbonitrile,
(4aS,8aS)-4,4,8a-trimethyl-3-oxo-7-(3-pyridyl)-5,8-dihydro-4aH-naphthalene-2-carbonitrile hydrochloride,
(4aS,7S,8aS)-4,4,8a-trimethyl-3-oxo-7-pyrrolidin-1-yl-5,6,7,8-tetrahydro-4aH-naphthalene-2-carbonitrile,
(4aR,7S,8aS)-7-(3,4-dihydro-1H-isoquinolin-2-yl)-4,4,8a-trimethyl-3-oxo-5,6,7,8-tetrahydro-4aH-naphthalene-2-carbonitrile,
(4aS,7S,8aS)-7-amino-4,4,8a-trimethyl-3-oxo-5,6,7,8-tetrahydro-4aH-naphthalene-2-carbonitrile hydrochloride,
N-[(2S,4aS,8aS)-7-cyano-5,5,8a-trimethyl-6-oxo-2,3,4,4a-tetrahydro-1H-naphthalen-2-yl]benzamide,
N-[(2S,4aS,8aS)-7-cyano-5,5,8a-trimethyl-6-oxo-2,3,4,4a-tetrahydro-1H-naphthalen-2-yl]cyclohexanecarboxamide,
N-[(2S,4aS,8aS)-7-cyano-5,5,8a-trimethyl-6-oxo-2,3,4,4a-tetrahydro-1H-naphthalen-2-yl]benzenesulfonamide,
(4aS,7S,8aS)-7-[benzyl(methyl)amino]-4,4,8a-trimethyl-3-oxo-5,6,7,8-tetrahydro-4aH-naphthalene-2-carbonitrile,
(4aS,7S,8aS)-7-(dimethylamino)-4,4,8a-trimethyl-3-oxo-5,6,7,8-tetrahydro-4aH-naphthalene-2-carbonitrile hydrochloride,
(4aR,8aR)-4,4,8a-trimethyl-3,7-dioxo-4a,5,6,8-tetrahydronaphthalene-2-carbonitrile,
(4aR,7S,8aR)-7-hydroxy-4,4,8a-trimethyl-3-oxo-7-phenyl-4a,5,6,8-tetrahydronaphthalene-2-carbonitrile,
(4aR,7R,8aR)-7-hydroxy-4,4,7,8a-tetramethyl-3-oxo-4a,5,6,8-tetrahydronaphthalene-2-carbonitrile,
(4aR,8aR)-7,7-difluoro-4,4,8a-trimethyl-3-oxo-4a,5,6,8-tetrahydronaphthalene-2-carbonitrile,
(4aR,7R,8aR)-7-benzyl-7-hydroxy-4,4,8a-trimethyl-3-oxo-4a,5,6,8-tetrahydronaphthalene-2-carbonitrile,
(4aR,8aR)-4,4,7,8a-tetramethyl-3-oxo-5,8-dihydro-4aH-naphthalene-2-carbonitrile,
(4aR,7R,8aR)-7-methoxy-4,4,7,8a-tetramethyl-3-oxo-4a,5,6,8-tetrahydronaphthalene-2-carbonitrile,
(4aR,8aR)-4,4,8a-trimethyl-3-oxo-7-phenyl-5,8-dihydro-4aH-naphthalene-2-carbonitrile,
(4aR,8aR)-4,4,8a-trimethyl-7-methylene-3-oxo-4a,5,6,8-tetrahydronaphthalene-2-carbonitrile,
(4aR,8aR)-4,4,8a-trimethyl-3-oxo-5,8-dihydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]-N-methyl-benzamide,
(4aS,7R,8aR)-4,4,8a-trimethyl-7-[(3-methyloxetan-3-yl)amino]-3-oxo-5,6,7,8-tetrahydro-4aH-naphthalene-2-carbonitrile,
(4aR,7R,8aR)-7-hydroxy-4,4,8a-trimethyl-3-oxo-5,6,7,8-tetrahydro-4aH-naphthalene-2-carbonitrile,
(4aR,7S,8aR)-7-hydroxy-4,4,8a-trimethyl-3-oxo-5,6,7,8-tetrahydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]acetamide,
(4aS,7R,8aR)-4,4,8a-trimethyl-3-oxo-7-(2,2,2-trifluoroethylamino)-5,6,7,8-tetrahydro-4aH-naphthalene-2-carbonitrile,
N-[(2R,4aS,8aR)-7-cyano-5,5,8a-trimethyl-6-oxo-2,3,4,4a-tetrahydro-1H-naphthalen-2-yl]-N-methyl-acetamide,
N-[(2R,4aS,8aR)-7-cyano-5,5,8a-trimethyl-6-oxo-2,3,4,4a-tetrahydro-1H-naphthalen-2-yl]benzamide,
(4aR,7S,8aR)-7-methoxy-4,4,8a-trimethyl-3-oxo-5,6,7,8-tetrahydro-4aH-naphthalene-2-carbonitrile,
N-[(1R,4aS,8aS)-7-cyano-5,5,8a-trimethyl-6-oxo-2,3,4,4a-tetrahydro-1H-naphthalen-1-yl]acetamide,
N-[(1S,4aS,8aS)-7-cyano-5,5,8a-trimethyl-6-oxo-2,3,4,4a-tetrahydro-1H-naphthalen-1-yl]acetamide, and
(4aR,8aS)-4,4,8a-trimethyl-3,8-dioxo-4a,5,6,7-tetrahydronaphthalene-2-carbonitrile, or a pharmaceutically acceptable salt thereof.

12. A pharmaceutical composition comprising at least one compound of claim 1, or a pharmaceutically acceptable salt thereof, and at least one pharmaceutically acceptable excipient.

13. A method of activating Nrf2 in a subject in need thereof, comprising administering to the subject an effective amount of at least one compound according to claim 1, or a pharmaceutically acceptable salt thereof, thereby activating Nrf2 in the subject.

14. The compound of claim 1, wherein the compound is represented by one of Formulae III, IV, VI and VII:

(III)

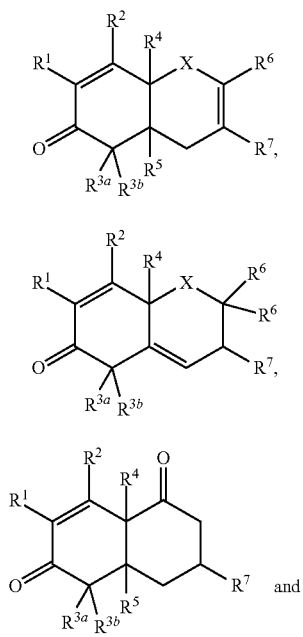

(IV)

(VI)

and (VII)

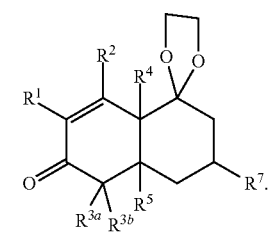

15. The compound of claim 1, wherein the compound is represented by one of Formula V:

(V)

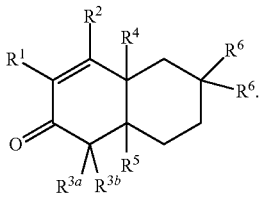

16. The compound of claim 15, wherein $R^6$, in each occurrence, is independently halo, $-NO_2$, $-CN$, $-N_3$, $C_{1-12}$alkyl, $C_{2-12}$alkenyl, $C_{2-12}$alkynyl, a 3 to 12-membered carbocyclyl, a 3 to 12-membered heterocyclyl, $-C(O)R^{6a}$, $-C(S)R^{6a}$, $-C(O)OR^{6a}$, $-C(S)SR^{6a}$, $-C(O)SR^{6a}$, $-C(S)OR^{6a}$, $-SC(O)R^{6a}$, $-OC(S)R^{6a}$, $-SC(S)R^{6a}$, $-C(O)N(R^{6a})_2$, $-OR^{6a}$, $-SR^{6a}$, $-N(R^{6a})_2$, $-N(R^{6a})OR^{6a}$, $-N(R^{6a})S(O)_2R^{6a}$, $-N(R^{6a})C(O)R^{6a}$, $-N(R^{6a})N(R^{6a})_2$, $-N(R^{6a})C(O)OR^{6a}$, $-N(R^{6a})C(O)N(R^{6a})_2$, $-S(O)_2R^{6a}$, $-S(O)R^{6a}$, $-S(O)N(R^{6a})_2$, $-S(O)_2N(R^{6a})_2$, $-N^+(R^{6a})_3$, $-S^+(R^{6a})_2$ or $-Si(R^{6a})_3$; or the two $R^6$ groups, taken together, are oxo, $C_{1-12}$ alkylidene, $=NR^{6a}$ or

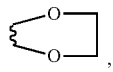

wherein the $C_{1-12}$alkyl, $C_{2-12}$alkenyl, $C_{2-12}$alkynyl, 3 to 12-membered carbocyclyl, 3 to 12-membered heterocyclyl, $C_{1-12}$alkylidene, and

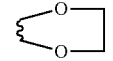

are each optionally substituted with one or more $R^{65}$.

* * * * *